(12) United States Patent
Rogers et al.

(10) Patent No.: US 11,766,280 B1
(45) Date of Patent: Sep. 26, 2023

(54) INTERSPINOUS IMPLANT INSERTION INSTRUMENT WITH WING ACTUATION TOOL

(71) Applicant: Spinal Simplicity, LLC, Overland Park, KS (US)

(72) Inventors: Adam Rogers, Overland Park, KS (US); Douglas Snell, Portland, ME (US); Annaria Barnds, Roeland Park, KS (US); Adam Frock, Lenexa, KS (US); Jeffrey David Lee, Prairie Village, KS (US); Jeff Slover, Lee's Summit, MO (US)

(73) Assignee: Spinal Simplicity, LLC, Overland Park, KS (US)

(*) Notice: Subject to any disclaimer, the term of this patent is extended or adjusted under 35 U.S.C. 154(b) by 0 days.

(21) Appl. No.: 17/944,107

(22) Filed: Sep. 13, 2022

Related U.S. Application Data

(63) Continuation of application No. 17/716,822, filed on Apr. 8, 2022, now abandoned.

(51) Int. Cl.
*A61B 17/70* (2006.01)
*A61F 2/46* (2006.01)
*A61B 17/00* (2006.01)

(52) U.S. Cl.
CPC ...... *A61B 17/7068* (2013.01); *A61B 17/7065* (2013.01); *A61B 17/7082* (2013.01); *A61F 2/4611* (2013.01); *A61B 2017/00862* (2013.01); *A61F 2002/4615* (2013.01); *A61F 2002/4627* (2013.01); *A61F 2002/4635* (2013.01)

(58) Field of Classification Search
CPC . A61B 17/70; A61B 17/7062; A61B 17/7065; A61B 17/7067–7068; A61B 17/88; A61B 17/8841
See application file for complete search history.

(56) References Cited

U.S. PATENT DOCUMENTS

| | | | | |
|---|---|---|---|---|
| 2006/0149278 A1* | 7/2006 | Abdou | ......... | A61F 2/4611 606/90 |
| 2008/0243250 A1* | 10/2008 | Seifert | ......... | A61B 90/39 623/17.16 |
| 2009/0054988 A1* | 2/2009 | Hess | ......... | A61B 17/025 623/17.11 |
| 2009/0198245 A1* | 8/2009 | Phan | ......... | A61F 2/4455 606/99 |

(Continued)

OTHER PUBLICATIONS

PCT Patent Application PCT/US2023/017788 International Search Report and Written Opinion of the International Searching Authority dated Jul. 21, 2023.

*Primary Examiner* — Eduardo C Robert
*Assistant Examiner* — Michelle C Eckman
(74) *Attorney, Agent, or Firm* — Erise IP, P.A.

(57) ABSTRACT

An insertion instrument for inserting an implant includes an elongated main body having a proximal handle and a distal portion that selectively couples to the implant. A wing actuation tool is slidably engaged in a central passage of the elongated main body to fix the implant to the elongated main body. The wing actuation tool temporarily attaches to the implant allowing for deployment and retraction of wings of the implant during surgery. Longitudinal translation of the wing actuation tool deploys an actuation plunger of the implant.

20 Claims, 33 Drawing Sheets

(56) References Cited

U.S. PATENT DOCUMENTS

| | | | |
|---|---|---|---|
| 2009/0292316 A1* | 11/2009 | Hess | A61B 17/7065 606/279 |
| 2010/0106191 A1* | 4/2010 | Yue | A61B 17/7065 606/279 |
| 2010/0234889 A1* | 9/2010 | Hess | A61B 17/00234 606/279 |
| 2012/0059480 A1 | 3/2012 | Schell et al. | |
| 2013/0331890 A1* | 12/2013 | Calvosa | A61B 17/7071 606/249 |
| 2014/0194930 A1* | 7/2014 | Hess | A61B 17/7065 606/249 |
| 2014/0358186 A1* | 12/2014 | Frock | A61B 17/7062 606/86 A |
| 2017/0296238 A1* | 10/2017 | Snell | A61B 17/7082 |
| 2018/0161175 A1 | 6/2018 | Frasier et al. | |

\* cited by examiner

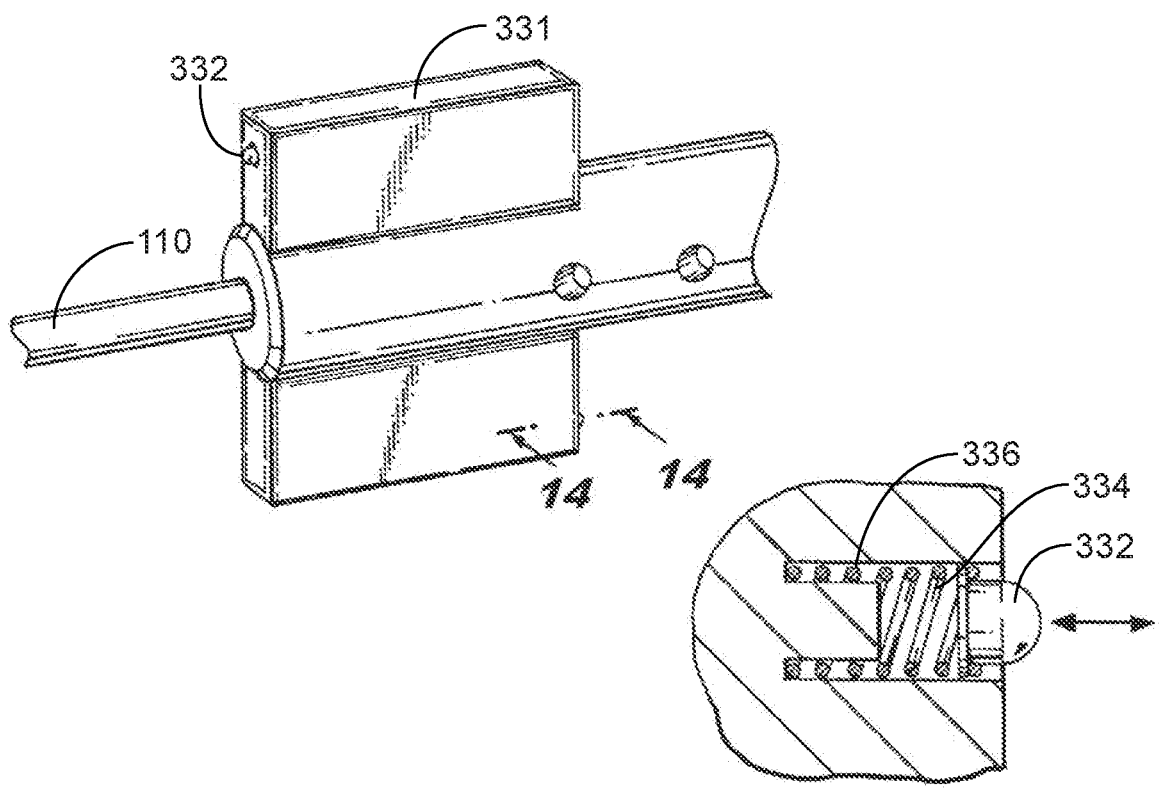
*Fig. 13*
*Fig. 14*
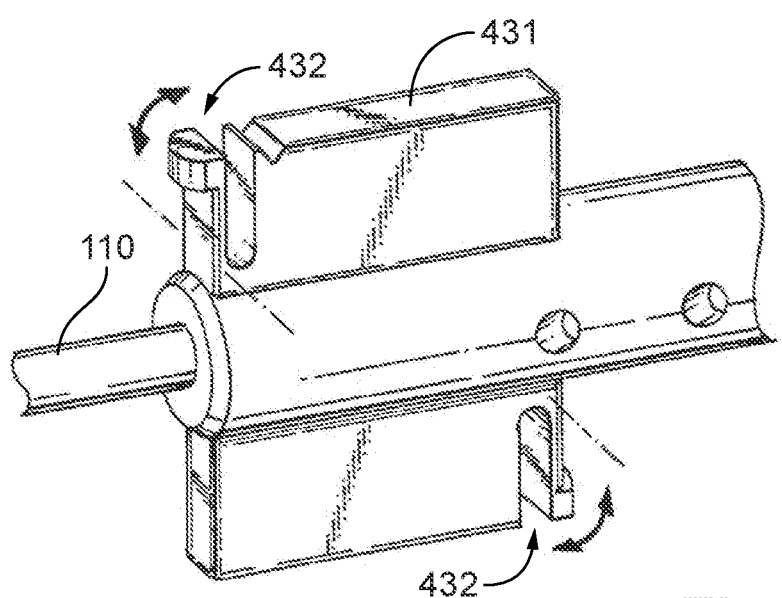
*Fig. 15*

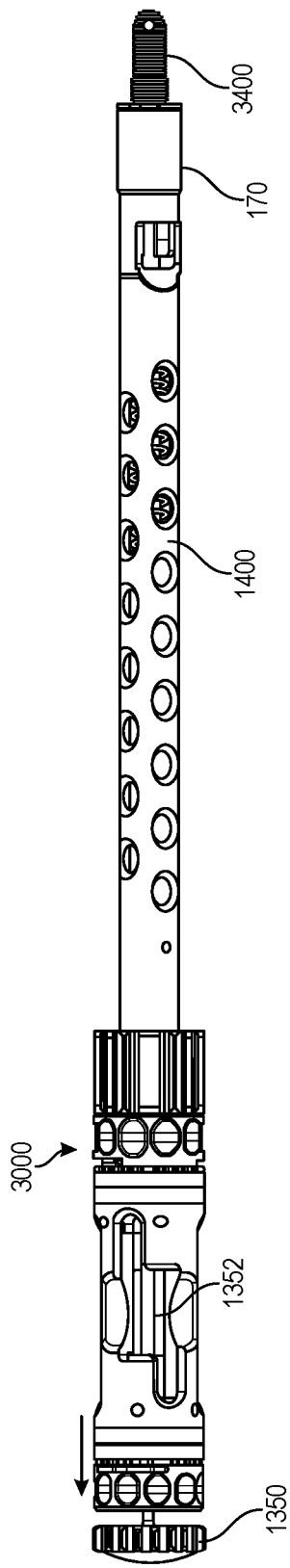
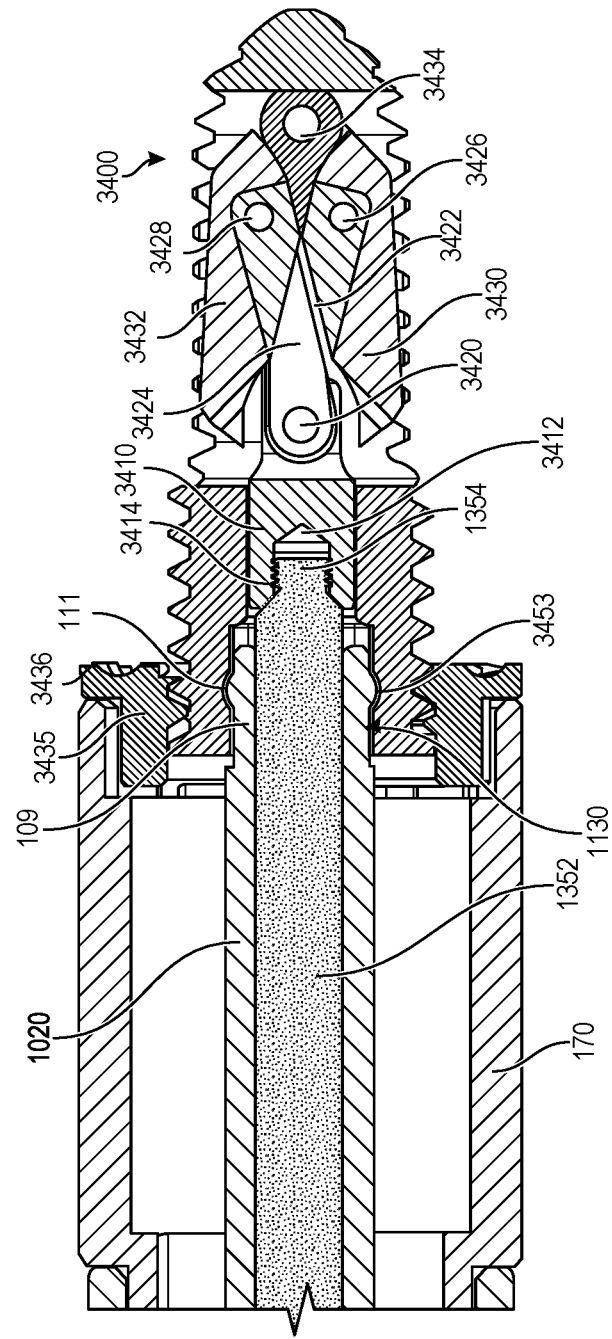
FIG. 53
FIG. 54

INTERSPINOUS IMPLANT INSERTION INSTRUMENT WITH WING ACTUATION TOOL

CROSS-REFERENCE TO RELATED APPLICATIONS

This Application is a continuation of U.S. patent application Ser. No. 17/716,822 filed Apr. 8, 2022, which is incorporated herein by reference in its entirety.

BACKGROUND OF THE INVENTION

1. Field of the Invention

The subject technology is directed to instruments for inserting spinal implants, and more particularly, to an insertion instrument that is easily assembled and disassembled for required cleaning while being able to effectively deploy an interspinous process implant for spinal stabilization, for percutaneous placement in a target interspinous process space, wherein the implant can also serve as a fusion cage spacer to treat lumbar spinal stenosis.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. Some surgical procedures for treating spinal stenosis are decompressive laminectomy and interspinous process decompression (IPD). A well-known implant used for performing IPD surgery is the X-STOP® device, which is described in U.S. Pat. No. 6,419,676, the disclosure of which is herein incorporated by reference in its entirety. Another interspinous process implant placed in a minimally invasive surgical procedure is disclosed in U.S. Pat. No. 9,545,267, which is also incorporated herein by reference in its entirety.

Examples of particularly useful interspinous process implant and fusion devices are disclosed in commonly assigned U.S. Pat. Nos. 9,861,399, 8,945,184; 9,314,276, 9,907,581, and 9,757,164, U.S. Patent Application Publication No. 2022/0054279, and U.S. Patent Application Publication No. 2022/0054280, and U.S. application Ser. No. 17/677,677, the disclosures of which are all incorporated herein by reference in their entirety.

One aspect of effective insertion of these implants is to provide a low profile instrument for deploying the implant. Often, the insertion instrument has several moving parts. Because of the cost of the insertion instruments, the instruments are re-used many times. For such insertion instruments to be re-used, the insertion instruments must be properly and fully cleaned without damage or loss of the components.

SUMMARY OF THE INVENTION

An insertion instrument for inserting an implant includes an elongated main body having a proximal handle and a distal portion that selectively couples to the implant. A plunger is slidably engaged in a central passage of the elongated main body configured to fix the implant to the elongated main body by selectively filling the central passage within the distal portion. A hex nut driver is concentrically located about the plunger and elongated main body to deploy an actuation plunger of the implant. The proximal handle portion of the main body includes a staggered path therethrough for accepting a tab of the plunger therein. Advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant.

The insertion instrument includes a plunger knob rotatably coupled to the plunger wherein rotation of the knob translates the plunger tab within the staggered path. The staggered path is a cut-out in the proximal handle that includes two parallel linear paths with a perpendicular transition wall there between. Rotation of a plunger knob translates the plunger tab proximally and distally and wherein rotation of the handle transitions the plunger tab along the transition wall and between the two linear paths.

The insertion instrument further includes a knob of the hex nut driver which can be rotatably coupled to a distal threaded portion of the handle through a distal end cap wherein the knob of the hex nut is configured to deploy the implant. The insertion instrument may further include a plunger knob rotatably coupled to a proximal threaded portion of the handle through a proximal end cap wherein the plunger knob is configured to translate the plunger tab within the staggered path.

In an embodiment, the plunger tab, a plunger knob, and a knob of the hex nut driver include a black PVD (physical vapor deposition) coating configured to indicate portions of the insertion instrument that change position during operation.

The insertion instrument may still further include a proximal end cap between a plunger knob and a proximal portion of the handle and a distal end cap between a distal portion of the handle and a knob of the hex nut driver. The proximal end cap can include at least one flexible tooth corresponding to a plurality of ratchet teeth of the handle. The at least one flexible tooth and plurality of ratchet teeth configured to auto-lock the plunger and plunger knob to the handle and prevent premature loosening. The distal end cap can include at least one flexible tooth corresponding to a plurality of ratchet teeth of the handle. The at least one flexible tooth and plurality of ratchet teeth are configured to auto-lock the hex nut driver and the handle together and prevent premature loosening.

The distal portion of the main body can include at least two flexible arms configured to friction fit the implant to the insertion instrument. A tip of the distal portion of the main body can match an inner diameter of the implant thereby configured to control mounting, torquing and retention of the implant with the main body.

In the unlocked position, the plunger tab is in the proximal most position of the staggered path. In the locked position, the plunger tab is positioned adjacent a transition wall of the staggered path. In the deployed position, the plunger tab is in the distal most position of the staggered path.

In one embodiment, the plunger tab is positioned at a proximal portion of the plunger and is generally rectangular, with the plunger extending through a central portion thereof. In another embodiment, the plunger tab includes at least two ball nose springs disposed on opposing faces of the plunger tab. In yet another embodiment, the plunger tab includes flexible tabs disposed on opposing faces of the plunger tab.

An insertion device for a spinal implant, wherein the spinal implant includes an elongated body to function as a spacer placed in a target interspinous process space between two adjacent spinous processes. The body defines an interior and a proximal internal recess for access to the interior, the proximal internal recess forming a transverse groove. A distal anchor that is at least partially threaded and has opposing radially deployable blades is mounted for rotation about a pin transversely mounted in the interior. A proximal anchor including a spike cap is mounted to slide along the body and a drive nut mounted for longitudinal movement along the body between a first position spaced apart from the distal anchor and a second position relatively closer to the distal anchor to thereby compress the two adjacent spinous processes between the spike cap and the distal anchor. An actuation plunger is slidably inside the interior for moving the blades from a stowed position to an implant deployed position.

The insertion device includes an elongated main body having a distal locking portion for coupling to the implant and a proximal handle portion. The main body defining a central passage and the distal locking portion having at least one flexible arm to flex radially inward. A plunger is slidably coupled in the central passage for movement between an unlocked position for mounting the implant on the distal locking portion, a locked position for locking the implant on the distal locking portion, and an insertion instrument deployed position for deploying the actuation plunger to move the blades from the stowed position to the deployed position. A hex nut driver rotatably mounted on the main body having a socket end for engaging the drive nut to, in turn, move the hex nut. The proximal handle portion of the main body includes a staggered path therethrough for accepting a tab of the plunger therein configured to control the advancement and retraction of the plunger within the central passage of the main body.

In the unlocked position, when the implant is mounted on the insertion instrument, the plunger tab is in the proximal most position of the staggered path and the flexible arms are in the transverse groove. In the locked position, the plunger tab is positioned adjacent a transition wall of the staggered path, the flexible arms are in the transverse groove and the plunger extends through the central passage to be concentric with the flexible arms. In the deployed position, the plunger tab is in the distal most position of the staggered path, the plunger extends out of the central passage to move the actuation plunger of the implant.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those skilled in the art to which the subject invention relates will readily understand how to make and use the insertion instrument of the subject technology without undue experimentation, embodiments thereof will be described in detail herein below with reference to the following figures.

FIG. 13 is a perspective view of an alternate embodiment of a plunger tab, showing a spring-loaded detent.

FIG. 14 is a cross-section view taken along line 14-14 of FIG. 13, showing an internal spring.

FIG. 15 is a perspective view of another alternate embodiment of a plunger tab, showing integrated flexible legs.

FIG. 53 is a side view of the insertion instrument of FIG. 43 attached to the implant of FIG. 51 in a retracted configuration.

FIG. 54 is a cross sectional view of the insertion instrument attached to the implant of FIG. 51 in the retracted configuration.

DETAILED DESCRIPTION

Figure 1:
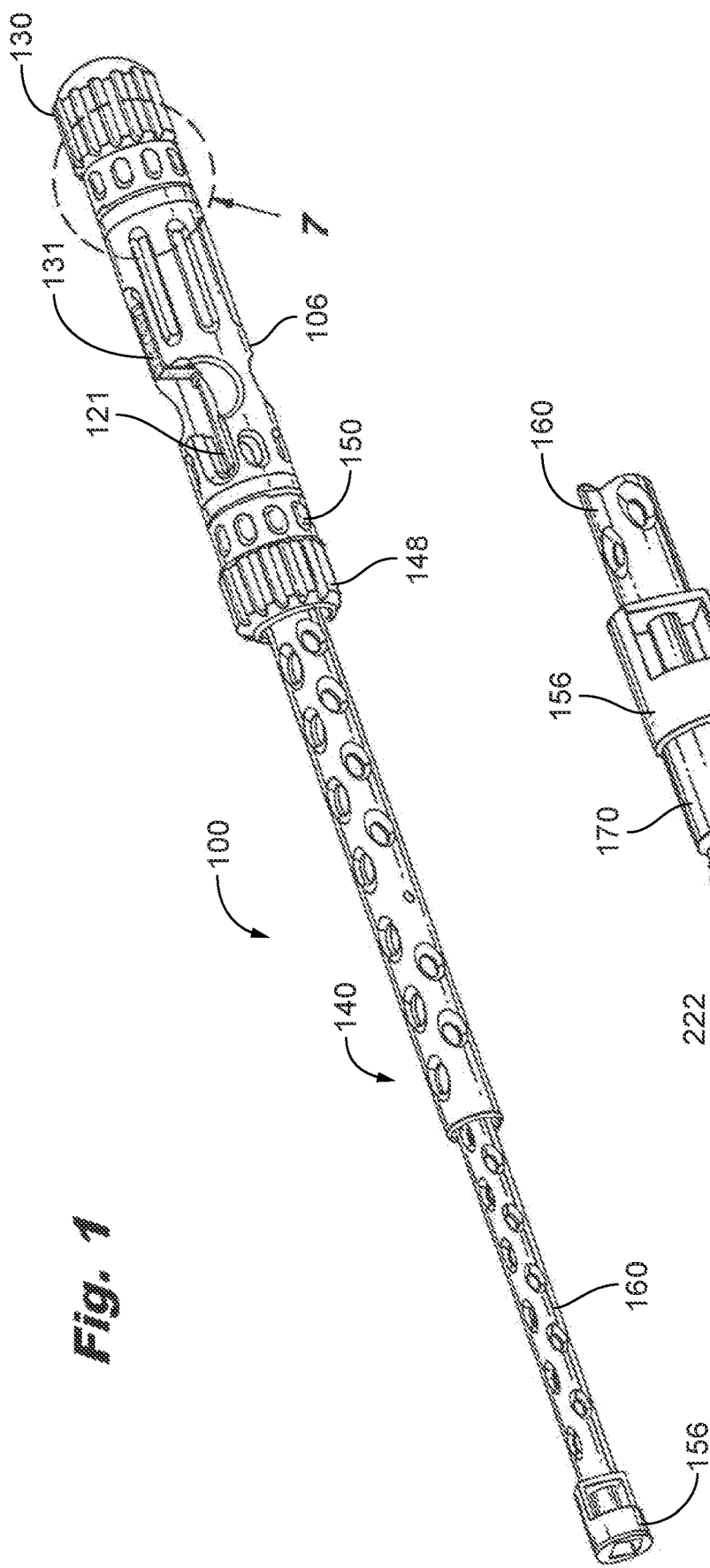
FIG. 1 is a perspective view of an insertion instrument in accordance with a first exemplary embodiment of the subject technology.

The present disclosure overcomes many of the prior art problems associated with instruments for inserting spinal implants and other devices such as cage spacers and the like. The advantages and other features of the instruments and methods disclosed herein will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed systems or methods. The shapes and sizes of components are also exemplary and unless otherwise specified, can be altered without materially affecting or limiting the disclosed technology.

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Insertion Instrument

Referring now to FIG. 1, a perspective view of an assembled insertion instrument 100 for inserting an implant in accordance with the subject technology is shown. The insertion instrument 100 is particularly useful for inserting interspinous process implants and fusion cage spacers in accordance with those shown in U.S. PG Pub. No. 2010/0234889 (the '889 application).

Figure 2:
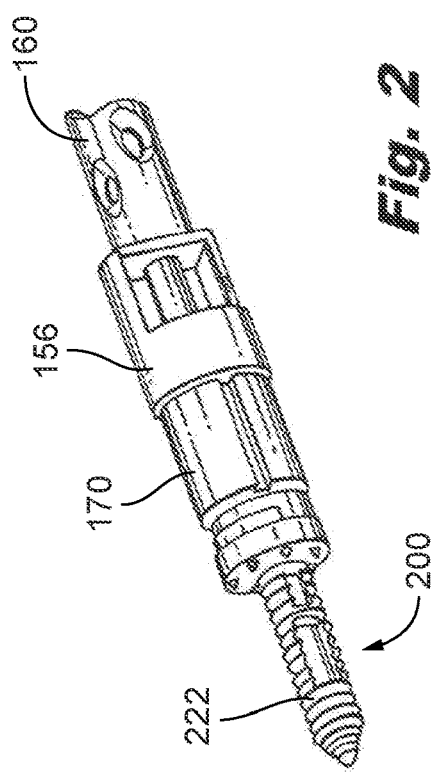
FIG. 2 is a perspective view of a distal portion of the insertion instrument of FIG. 1 with an implant in accordance with a first exemplary embodiment of the subject technology.
Figure 3:
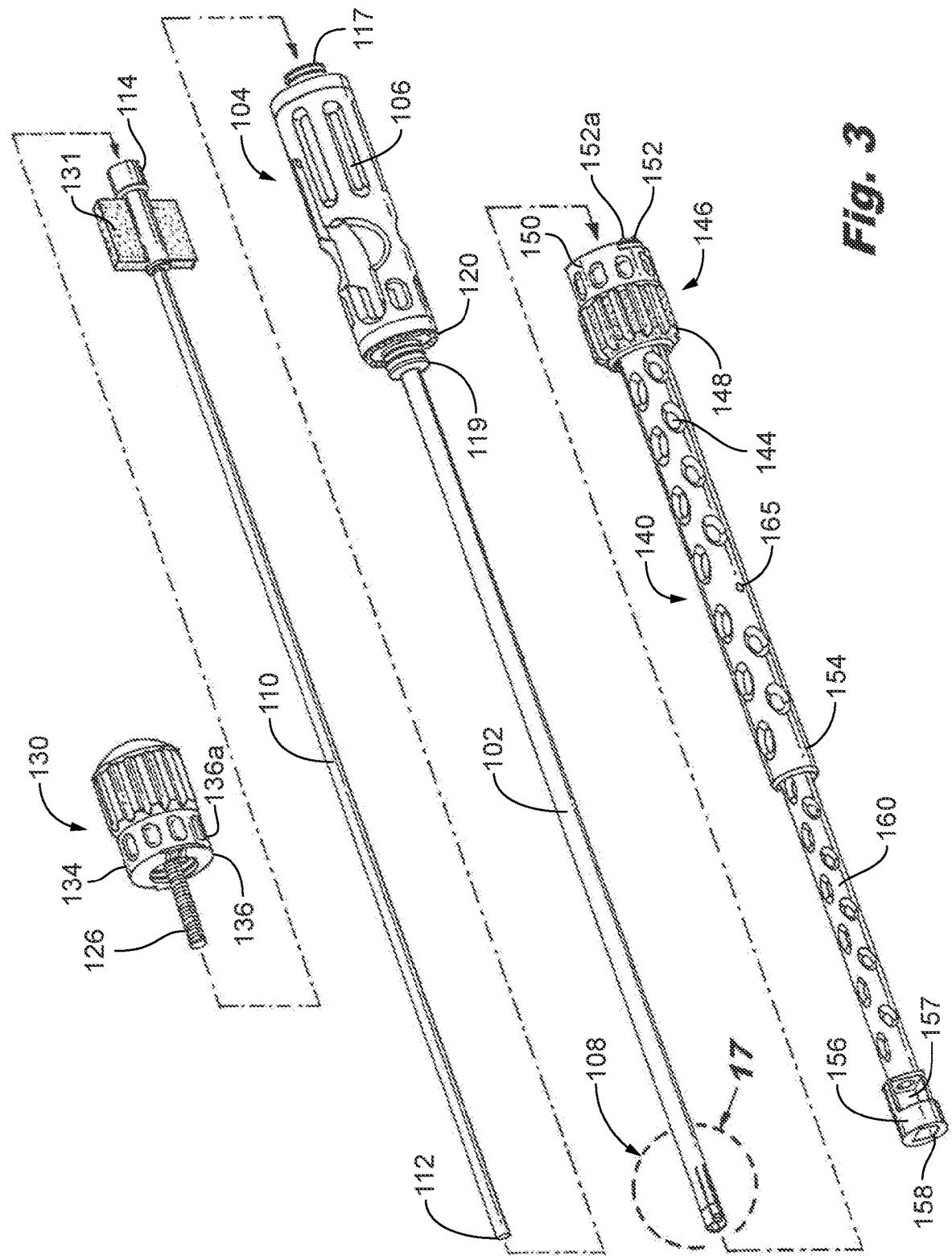
FIG. 3 is an exploded view of the insertion instrument of FIG. 1, illustrating the components thereof.

Referring additionally to FIG. 2, a perspective view of a distal portion of the insertion instrument 100 mounted with an implant 200 in accordance with the '889 application is shown. The insertion instrument includes four sub-assemblies that work together to lock and deploy an implant into an interspinous space. As best seen in FIG. 3, the four sub-assemblies include: an elongated main body 102 with a handle 106 at a proximal portion, a plunger knob 130, a plunger 110 which couples to the plunger knob 130 and handle 106, and a hex nut driver 140 concentrically about the plunger 110.

After use, the insertion instrument 100 can be disassembled easily to allow for full and proper cleaning, then reassembled to be used again. Preferably, the components of the insertion instrument 100 are fabricated from medical grade stainless steel, alloys, and/or polymers (e.g., RULON, PEEK) or another like durable material to allow for repeated use, cleaning and reuse.

Figure 17:
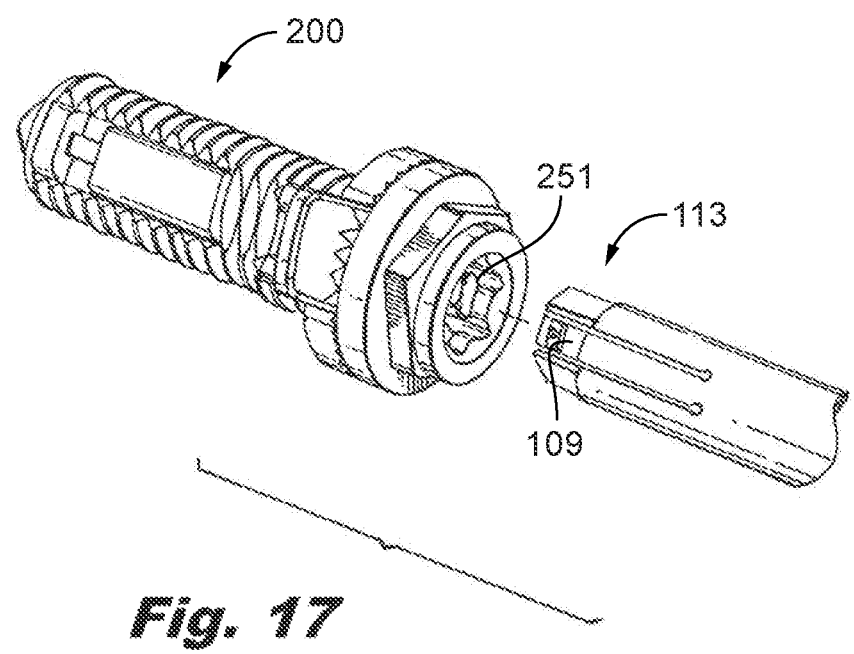
FIG. 17 is a perspective view of an implant and a distal portion of the main body, showing a hex-shaped shaft and football-shaped detents.

With continued reference to FIG. 3, the elongated main body 102 defines a central passage 104 and a distal portion 108 that selectively couples to the implant 200. The distal portion 108 includes flexible arms 109 (shown in FIG. 17) that allow compression of the tip 113. The tip 113 is roughly hexagonal shaped but with flexible arms 109. The tip 113 may include a generally "football shaped" protrusion, which aids in the mounting, torquing, and retention of an implant.

The handle 106 of the elongated main body 102 includes a proximal threaded feature 117 and a distal threaded feature 119 on a respective proximal face and distal face. The proximal threaded feature 117 couples the handle 106 to the plunger knob 130 and the distal threaded feature 119 couples the handle 106 to a knob 148 of the hex nut driver 140.

The plunger 110 slides into the central passage 104 of the elongated main body 102. The plunger 110 has a distal pushing end 112 for engaging the implant 200 and a locking cap 114. The locking cap 114 rotatably couples the plunger 110 to the plunger knob 130 and has a relatively thicker radius than the distal pushing end 112. Abutting the locking cap 114 is a plunger tab 131 extending outwardly. The plunger tab 131 is substantially rectangular with the plunger 110 extending through a central portion thereof.

The handle 106 includes a staggered path 121 (best seen in FIG. 9) for accepting the plunger tab 131 therein. More specifically, the staggered path 121 is a cut-out in the handle 106 that includes two parallel linear paths 123, 125 with a perpendicular transition wall 127 therebetween. As will be discussed in further detail throughout the disclosure, rotational movement of the plunger knob 130 moves the plunger tab 131 proximally and distally within the staggered path 121 allowing the plunger 110 to act as its own advancement and retraction mechanism.

Figure 16:
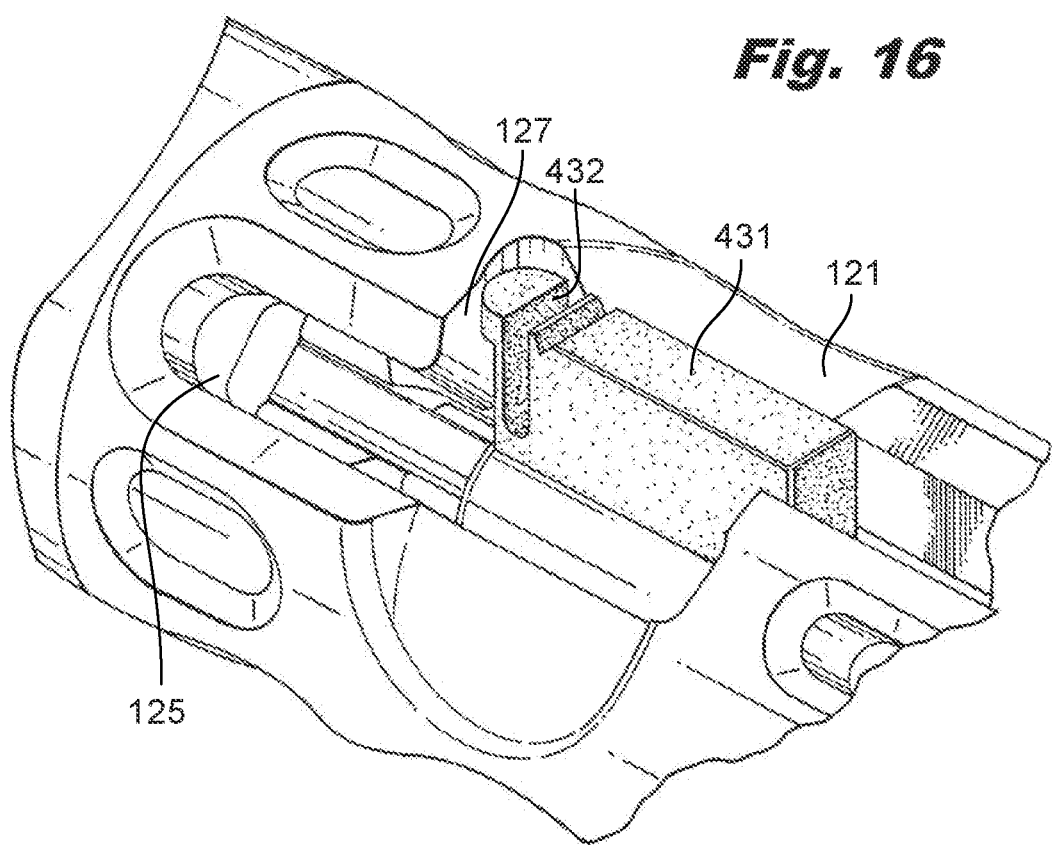
FIG. 16 is a perspective view of the plunger tab of FIG. 15, showing tabs secured with the transition wall.

FIGS. 13-16 illustrate additional embodiments of the plunger tab. In FIGS. 13 and 14, the plunger tab 331 includes a ball nose spring 332 and 334 on a proximal face and a distal face. The spring is positioned within a recess 336. FIGS. 15 and 16, integrated flexible tabs 432 are included in plunger tab 431. The flexible tabs 432 are also positioned along a proximal and distal face of the plunger tab 431. The ball nose spring 332 and the flexible tabs 432 engage the staggered path 121 and prevent accidental rotation of the plunger 110.

The hex nut driver 140 defines an axial passage 144 for receiving the distal portion 108 of the elongated main body 102. The hex nut driver 140 has a proximal portion 146 that includes a relatively larger radius knob 148 with end cap 150. A tubular intermediate portion 154 extends from the knob 148 and slidingly receives a drive shaft 160. The drive shaft 160 terminates in a socket end 156. The socket end 156 is also tubular but forms a square opening 158 for coupling to the implant 200. The socket end 156 also forms a transverse square locking passage 157.

Figure 4:
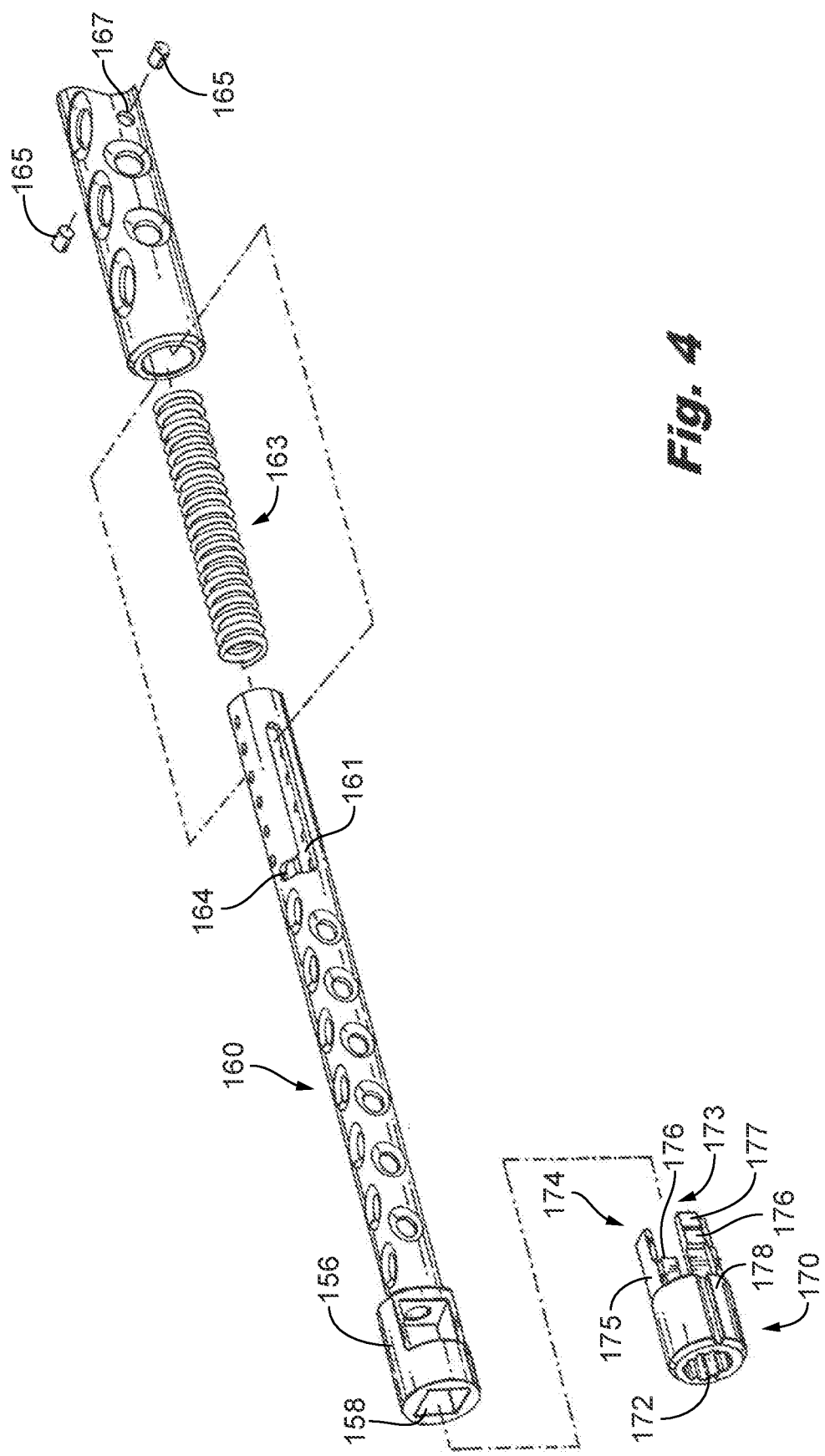
FIG. 4 is an exploded view of a hex nut driver and adapter for coupling to the implant.

The drive shaft 160 can be locked in a retracted position within the intermediate portion 154. Referring now to FIG. 4, an exploded view of the hex nut driver 140 is shown. The hex nut driver 140 has a spring 163 mounted within the intermediate portion 154 for biasing the drive shaft 160 distally. In order to lock the drive shaft 160 in a retracted position, the bias of the spring 163 must be overcome. To accomplish this locking, the drive shaft 160 forms two opposing complimentary slots 161 (only one slot 161 can be seen) and pins 165 mounted in opposing pinholes 167 on the intermediate portion 154. When assembled, the pins 165 ride in the respective slots 161 so that upon fully pushing the drive shaft 160 in the intermediate portion 154, a small rotation of the drive shaft 160 will set the pins 165 in a radial portion 164 of the slots 161 and retain the hex nut driver 140 in this compressed position.

An adapter 170 attaches to the square opening 158 of the hex nut driver 140 to provide a hex socket 172 for coupling to the implant 200. The hex socket 172 can vary in size to accommodate different size implants 200. The adapter 170 has a central axial passage 173 to slide over the tip 113 of the elongated main body 102. The adapter 170 has a standard male square open proximal end 174 to couple to the square opening 158. The proximal end 174 has two opposing rigid legs 175 intermediate two opposing flexible legs 176. Each of the flexible legs 176 has a locking tab 177 so that as the proximal end 174 is pushed into the square opening 158 of the hex nut driver 140, the legs 176 deflect to allow easy insertion, then the locking tabs 177 couple to the transverse locking passage 157 to securely retain the adapter 170 on the drive shaft 160. To remove the adapter 170, the locking tabs 177 are simply depressed while retracting the adapter 170. The adapter 170 also has opposing outer axial alignment ridges 178.

The Implant

The implant 200 may take a variety of different configurations and sizes. Preferably, the implant is useful for treatment of spondylolisthesis, central and foraminal lumbar stenosis, degenerative disc disease and the like. Beneficially, the implant 200 is percutaneously placed, provides stabilization of the spine, can be used with bone graft material to promote fusion, requires less than a 2.6 cm incision, and can be inserted with local or general anesthesia. As such, the recovery time is relatively quicker, and the hospital stay is relatively shorter. The implant 200 is shown and described with partial features shown and described for the sake of brevity. Further details can be found in the '889 application and in U.S. Patent Application Publication 2014/0358186 both of which are incorporated by reference herein in their entirety.

Figure 18:
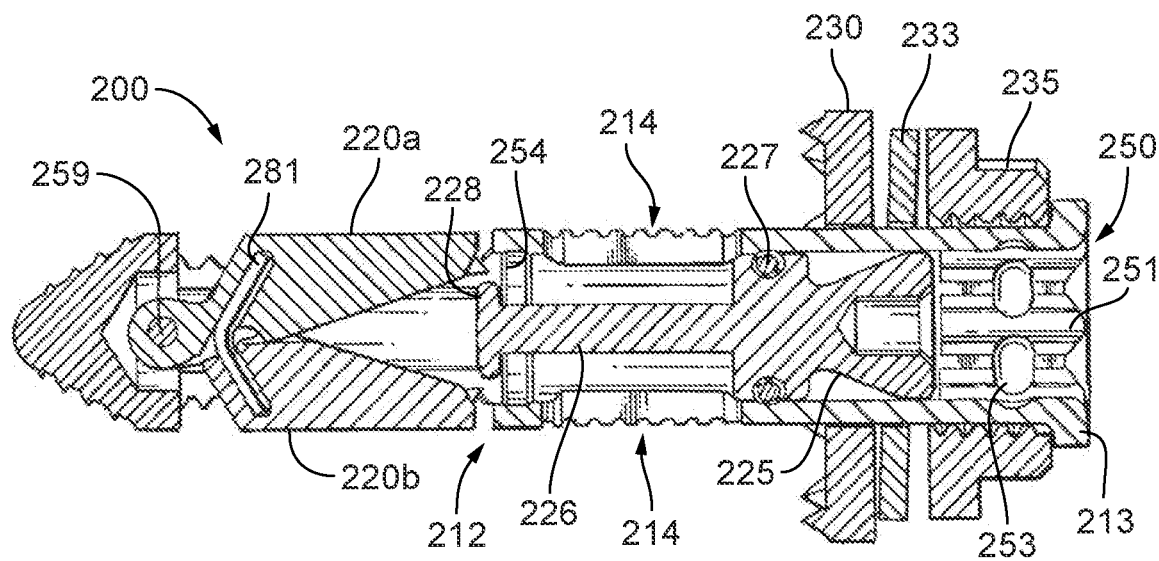
FIG. 18 is a cross-sectional view of the implant, showing the distal anchor elements are in a stowed position.
Figure 19:
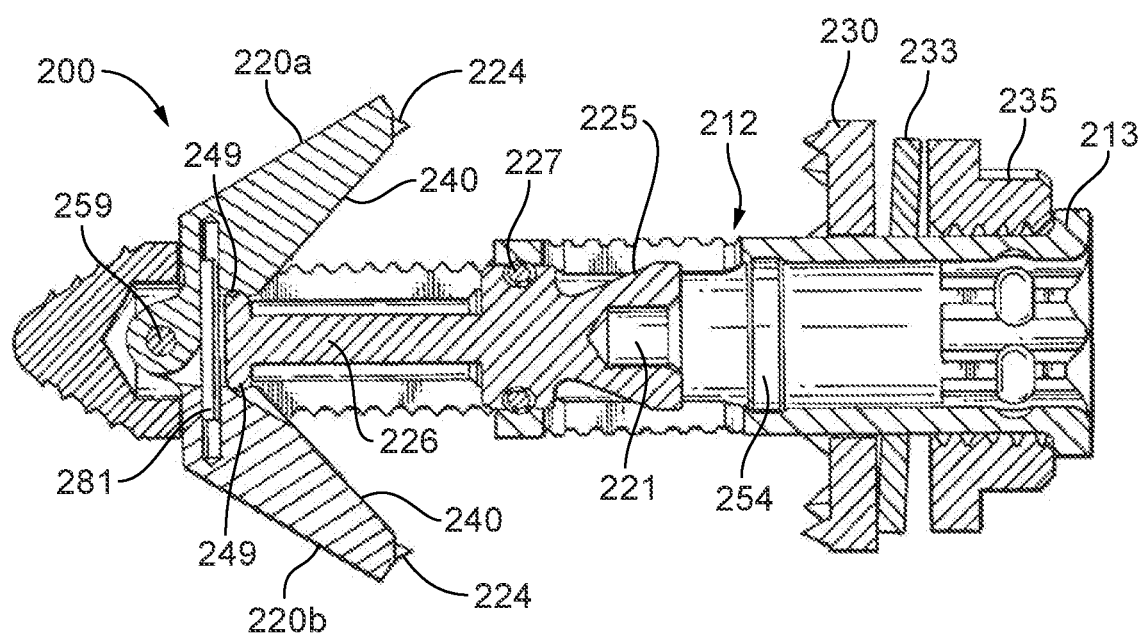
FIG. 19 is a cross-sectional view of the implant, showing the distal anchor elements in a deployed position.

FIGS. 18 and 19 illustrate in detail the interspinous process implant 200 for use with insertion instrument 100. The implant 200 includes a body 212, providing overall structure to the implant 200. The body 212, as illustrated, is provided with threads 222 (shown in FIG. 1) for facilitating insertion of the implant 200 into a target interspinous process space 382 (FIGS. 20-21) as will be described in more detail below, as well as for providing additional engagement with the anatomy of the patient in the target interspinous process space 382. Further, the threads 222 permit rotational engagement between the body 212 and a hex nut 235, provided to securely engage the implant 200 with interspinous processes 381a, 381b adjacent the target interspinous process space 382, which will be described in more detail below. Alternatively, the implant 200 can be provided without threads thereon, or with threads provided only on a portion thereof for one of the foregoing functions. That is, if desired, threads 222 can be provided only on the proximal end of the body 212, for engaging the hex nut 235 and not on the distal portion, or vice versa.

The implant 200 includes a distal anchor portion, which is configured as two opposed deployable blades 220 (220a, 220b). The blades 220 are provided with a common pivot, defined by a pin 259 passing therethrough, as well as through the body 212. Use of a common pivot advantageously minimizes the space required for housing all elements within the body 212 in their stowed state, although variations from this precise configuration are possible. For example, two separate pivots can be provided for each blade 220a, 220b, still in keeping with the invention. The blades 220, as illustrated, are provided with proximally directed spikes 224 for engaging the relevant adjacent bony anatomy, such as the spinous processes 381a, 381b. The blades 220 can alternatively be provided without such spikes 224.

In the illustrated embodiment, an implant plunger 226 is provided and includes a head portion 228 shaped and configured to act as a cam and cooperate with inner cam surfaces 240 formed on each of the blades 220a, 220b, as described above. As the head portion 228 moves distally, cam surfaces 240 of the blades 220a, 220b follow the outer surface of the head portion 228, and urge the blades 220a, 220b radially outwardly. In addition, the implant plunger 226 can include, as described above, a proximal head 225 having a proximal internal recess 221, and an angled distal surface to facilitate distally-directed urging and proximal-directed urging, respectively, applied from the proximal direction.

Preferably, the implant plunger 226 also includes a resilient catch 227. The catch 227 is configured to interface between the implant plunger 226 and internal surface features of the body 212, such as annular grooves or recesses 254. As described, the resilient catch 227 permits axial movement of the implant plunger 226, and in conjunction with the above-described internal surface features of the body 212, defined positions at which the implant plunger 226 is held, inhibiting unintentional movement therefrom. The catch 227 can be formed of any suitable material or configuration, such as from a resilient material, such as an elastomer, or as a resilient structure, such as a toroidal metallic coil, or a combination of these, for example. The catch 227 can be, in accordance with the invention, a canted coil, such as a Bal Latch™, available from Bal Seal Engineering, Inc. of Foothill Ranch, Calif., USA.

When deployed, as shown in FIG. 19, the blades 220 function in concert with the spike cap 230, which is axially moveable along the length of the implant 200. The hex nut 235 includes threads on its inner surface that engage the threads 222 provided on the outer surface of the body 212. Accordingly, rotational movement of the hex nut 235 yields axial movement thereof. When that axial movement is in the distal direction, the hex nut 235 urges the spike cap 230 distally until the spike cap 230 abuts the bony structures (e.g., spinous processes 381a, 381b) surrounding the target interspinous process space 382. If provided, protrusions or spikes 234 on the proximal anchor portion facilitate engagement with the bone and thus stabilization of the entire vertebrae-implant construct.

With continued reference to the cross-sectional views of FIGS. 18 and 19, the blades 220 can be provided with an internal spring element 281, spanning between respective recess in each of the blades 220a, 220b. The spring element 281 can be provided straight to maintain the blades 220a, 220b deployed (open) normally, or alternatively, bent, to maintain the blades 220a, 220b stowed (contracted) normally. In accordance with one aspect, the spring element 281 is provided bent, and urges the blades 220a, 220b inwardly, toward the stowed position, prior to and during implantation. Thus, in connection with the implant plunger 226, the spring element 281 serves to maintain a position of the blades 220. As illustrated, when the implant plunger 226 is fully extended, a head portion 228 thereof engages a corresponding detent 249 in the blades 220a, 220b. The engagement of the detent 249 by the head portion 228 further ensures secure deployment of the blades 220a, 220b.

The spring element 281 can alternatively be provided as normally straight, urging the blades 220a, 220b outwardly toward the deployed position, prior to, during and following implantation. During implantation, however, the spring element 281 permits inward rotation of the blades 220a, 220b, temporarily bending the spring element 281 in the process. Thus, during implantation the spring element 281 serves to maintain a position of the blades 220a, 220b against externally applied forces. Once placed in the target interspinous process space 382, the implant plunger 226 can be urged distally in order to lock the blades 220a, 220b in the deployed position. Engagement of the detent 249 by the head portion 228 of the implant plunger 226 further ensures maintenance of that position.

The body 212 of the implant 200 includes at its proximal end, an expanded-diameter portion 213, defining a proximal-most limit for traveling of the hex nut 235, spike cap 230 and a lock washer 233. Also in the proximal end portion, formed within the proximal internal recess 250, is a shaped socket 251 for engagement with the insertion instrument 100. As illustrated, the socket 251 is substantially hexagonal, with flat portions defined at regular angular intervals. Practicable departures from the precise configuration illustrated are possible. The shaped socket 251 facilitates mutual rotational engagement between the implant 200 and the insertion instrument 100.

Also provided in connection with the socket 251, are transverse grooves 253, which, in conjunction with the tip 113 of the elongated main body 102 and distal pushing end 112 of the plunger 110 mount and lock the implant 200 to the insertion instrument 100. The mounting and/or locking elements on the insertion instrument can also be, for example, a resiliently and optionally lockable protrusion extending laterally (i.e., radially) from the insertion instrument. The lockable protrusion may be, for example, a lockable spring-loaded spherical element, for example.

The implant 200 can be provided with one or more apertures 214 to permit packing of the implant, such as in the proximal internal recess 250 thereof, with osteogenesis-promoting substances to facilitate bone ingrowth and/or fusion, such as demineralized bone.

Assembly of the Insertion Instrument

Referring now to FIGS. 3-8, the insertion instrument is designed for ease of assembly. The distal portion 108 of the elongated main body 102 is inserted into the axial passage 144 of the hex nut driver 140. The knob 148 of the hex nut driver 140 is rotated to couple the distal threaded feature 119 of the handle 106 with the end cap 150 of the hex nut driver 140.

Figure 5:
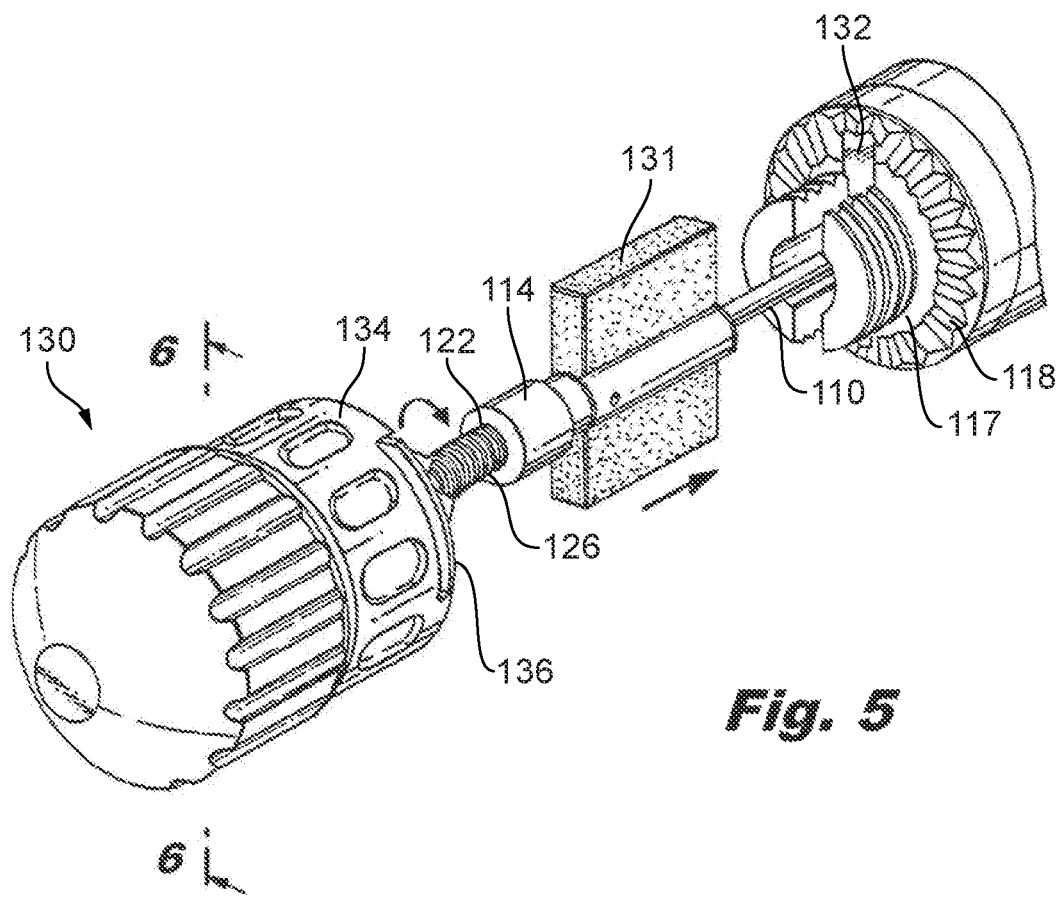
FIG. 5 is an exploded view of a plunger knob and plunger of the insertion instrument of FIG. 1, illustrating the components thereof.
Figure 6:
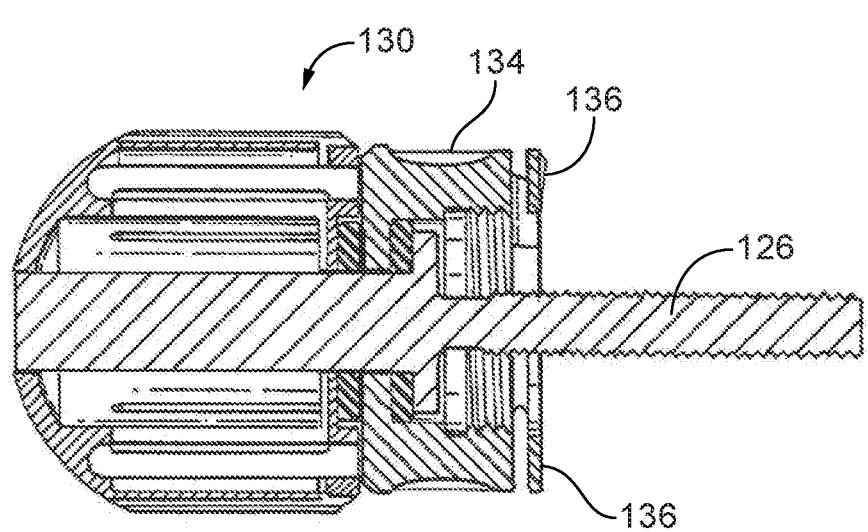
FIG. 6 is a side sectional view of the plunger knob of FIG. 5.

As best shown in FIG. 5, the plunger knob 130 is next coupled to the locking cap 114 of the plunger 110. The plunger knob 130 includes a threaded core 126 that is rotated into a recess 122 of the locking cap 114. The plunger 110 can next be inserted into the elongated main body 102. The handle 106 includes an opening 132 for slidably engaging the plunger tab 131 therein. As the plunger 110 and plunger tab 131 are slid within the handle 106, the end cap 134 of plunger knob 130 abuts the proximal face of the handle 106. The plunger knob 130 is rotated to threadably engage the proximal threaded feature 117 of the handle 106 and secure the plunger 110 and plunger knob 130 to the handle 106.

Figure 7:
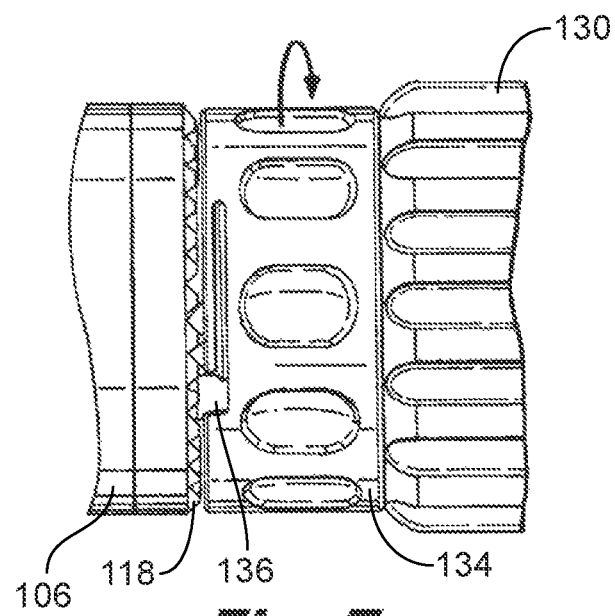
FIG. 7 is a side elevation view of the plunger knob and end cap, showing an auto-lock feature in closed position.
Figure 8:
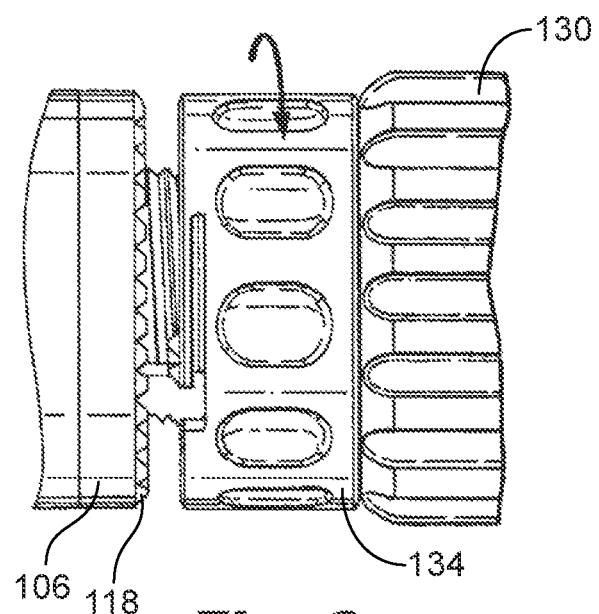
FIG. 8 is a side elevation view of the plunger knob and end cap, showing an auto-lock feature in an open position.

With reference to FIGS. 7 and 8, the insertion instrument 100 includes an auto-lock feature which enables a secure surgical instrument assembly while also allowing for disassembly without the use of additional tools. Each of the proximal face and distal face of the handle 106 include a plurality of ratchet teeth 118, 120, respectively. The plunger knob 130 and the knob 148 of the hex nut driver 140 each include an end cap 134, 150 welded thereto, respectively, that includes a flexible tab 136, 152 with at least two teeth 152a (shown best on end cap 150). As the plunger knob 130 and corresponding end cap 134 are threaded clockwise to the handle 106, the teeth 136a of the flexible tabs 136 engage with the ratchet teeth 118 of the proximal face and lock the handle 106 with the plunger knob 130. Similarly, as the hex nut driver 140 and corresponding end cap 150 are threaded clockwise to the handle 106, the teeth 152a of the end cap 150 engage with the ratchet teeth 120 of the distal face and lock the handle 106 and the hex nut driver 140. As shown in FIG. 8, counterclockwise motion loosens the teeth 136a, 152a of each of the flexible tabs 136, 152 on the respective end caps 134, 150 and thereby allows for disassembly.

Figure 9:
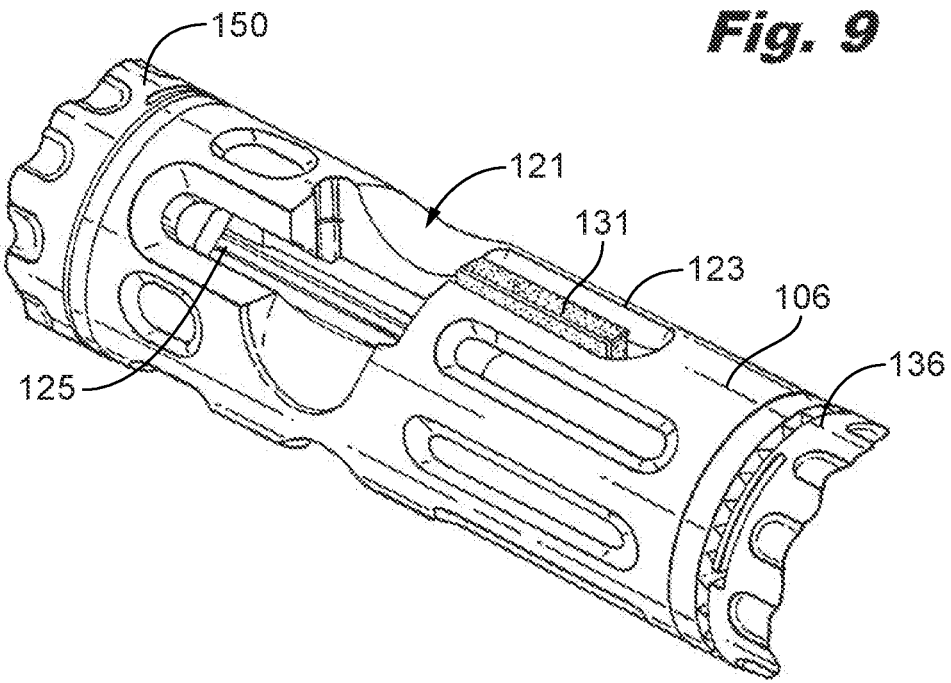
FIG. 9 is a perspective view of a handle of the insertion instrument of FIG. 1 with the plunger tab in a proximal position.

At this point, with the plunger 110 and plunger knob 130 secured to the handle 106, the plunger tab 131 is in the proximal position within the staggered path 121 (as shown in FIG. 9). The insertion instrument 100 is now in the "unlocked" position. "Unlocked" refers to the implant 200 not being secured to the insertion instrument 100 even if the implant 200 is mounted on the tip 113. The implant 200 is locked to the insertion instrument 100 by deploying the plunger 110 as described below.

Locking the Implant to the Insertion Instrument

To lock the implant 200 to the insertion instrument 100 the plunger 110 should be fully retracted into the unlocked position. This can be easily viewed by the plunger tab 131 being in the proximal most location within the staggered path 121 of the handle 106.

During use, three components of the insertion instrument are used to translate the plunger 110 and deploy the implant 200: the plunger knob 130, the plunger tab 131 and the knob 148 of the hex nut driver 140. Each of these components may include a coating with PVD. The black PVD coating provides anti-galling coating as well as a usability indicator to the user as to which instrument components are manipulated during the surgical technique.

To lock the implant, the distal portion 108 of the elongated main body 102 is uncovered by sliding the drive shaft 160 into the intermediate portion 154 of the hex nut driver 140. The drive shaft 160 is initially prevented from rotation because the pins 165 are riding in the slots 161 (best seen in FIG. 4). However, once the pins 165 bottom out in the slots 161, the user can hold the knob 148 and rotate the drive shaft 160 so the pins 165 come to rest in the radial portion 164 of the slots 161. As a result, the drive shaft 160 is retained in the intermediate portion 154 and will stay retracted even when released by the user.

A matching adapter 170 is slid over the distal portion 108 of the elongated main body 102 so that the legs 175, 176 can be inserted into the square opening 158. Preferably, the locking tabs 177 provide an audible click when the legs 176 deflect outward into the transverse locking passage 157 to confirm positive engagement for the user.

After positioning the adapter 170 on the drive shaft 160, the implant 200 can be partially engaged to the tip 113 by a snap friction fit. The tip 113 is slightly compressed, by virtue of the flexible arms 109, and passed into the proximal internal recess 250 of the implant 200 with the blades 220a, 220b of the implant 200 aligned with the flexible arms 109. The tip 113 stops within the recess 250 when the flexible arms 109 fit within the transverse groove 253. At this point, the implant 200 is coupled to the insertion instrument 100 but not yet "locked."

Figure 10:
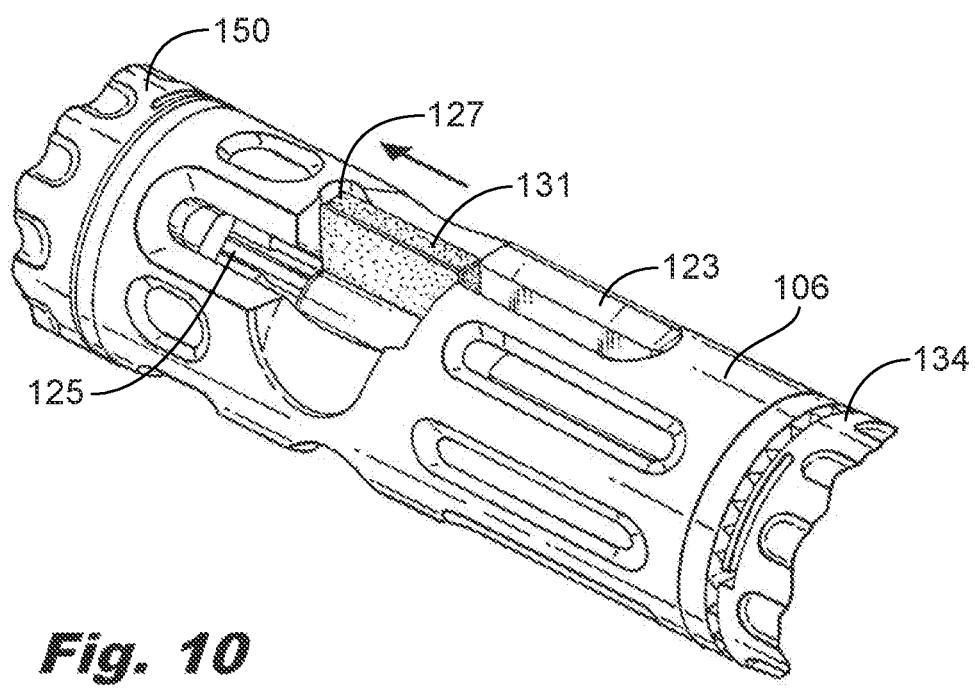
FIG. 10 is a perspective view of the handle of the insertion instrument of FIG. 1 with the plunger tab adjacent a transition wall.
Figure 11:
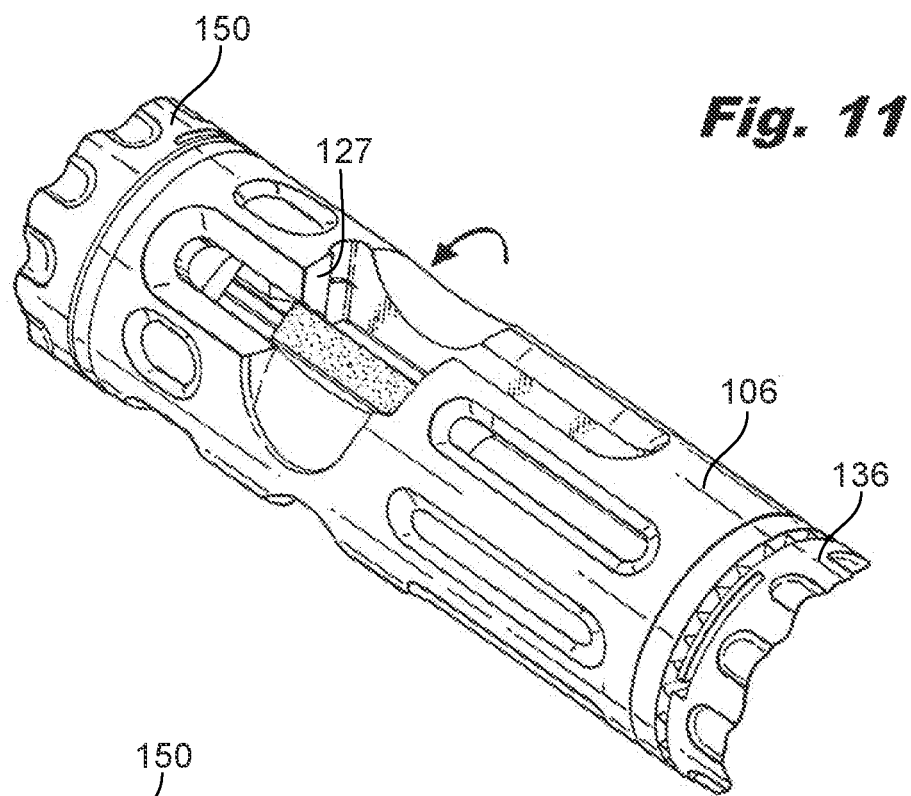
FIG. 11 is a perspective view of the handle of the insertion instrument of FIG. 1 with the plunger tab rotated.

To lock the implant 200 to the insertion instrument 100, the plunger 110 is moved from the unlocked position to the locked position. To move the plunger 110 distally, the plunger knob 130 is rotated clockwise (looking from the proximal end) until the plunger tab 131 rests adjacent the transition wall 127, as shown in FIGS. 9 and 10. The distal pushing end 112 of the plunger 110 is approximately flush with the tip 113 of the elongated main body 102. Thus, the flexible arms 109 of the elongated main body 102 can no longer flex out of the transverse groove 253. Consequently, the implant 200 is tightly coupled and locked to the tip 113 so that inadvertent removal does not occur. The insertion instrument 100 is now ready to have the socket end 156 of the hex nut driver 140 engaged to the hex nut 235 of the implant 200.

To engage the hex nut driver 140 to the hex nut 235 of the implant 200, the handle 106 is held to prevent rotation while the drive shaft 160 is rotated to bring the pins 165 out of the radial portion 164 of the slots 161. The spring 163 will bias the drive shaft 160 outward so care should be taken to slowly extend the drive shaft 160 to have the hex socket 172 properly engage the hex nut 235 of the implant 200 (best seen in FIG. 22). In order to have the hex socket 172 properly engage the hex nut 235, a slight manual rotation or jiggle of the drive shaft 160 may be required. The implant 200 is now locked to the insertion instrument 100 to be ready for spinal implantation. The force provided by the spring 163 is optimized to insure proper, reliable engagement between the adapter 170 and hex nut 235 while not providing excessive force to interfere with the operation of the insertion instrument 100 or deployment of the implant 200.

Deployment of the Implant in the Interspinous Space

FIGS. 20-23 illustrate various stages during insertion and placement of the implant 200 into a target interspinous process space 382. Additional details are set forth in U.S. patent application Ser. No. 12/011,905, filed Jan. 30, 2008 (U.S. Pub. No. 2009/0054988), which is incorporated herein by reference in its entirety.

Figure 20:
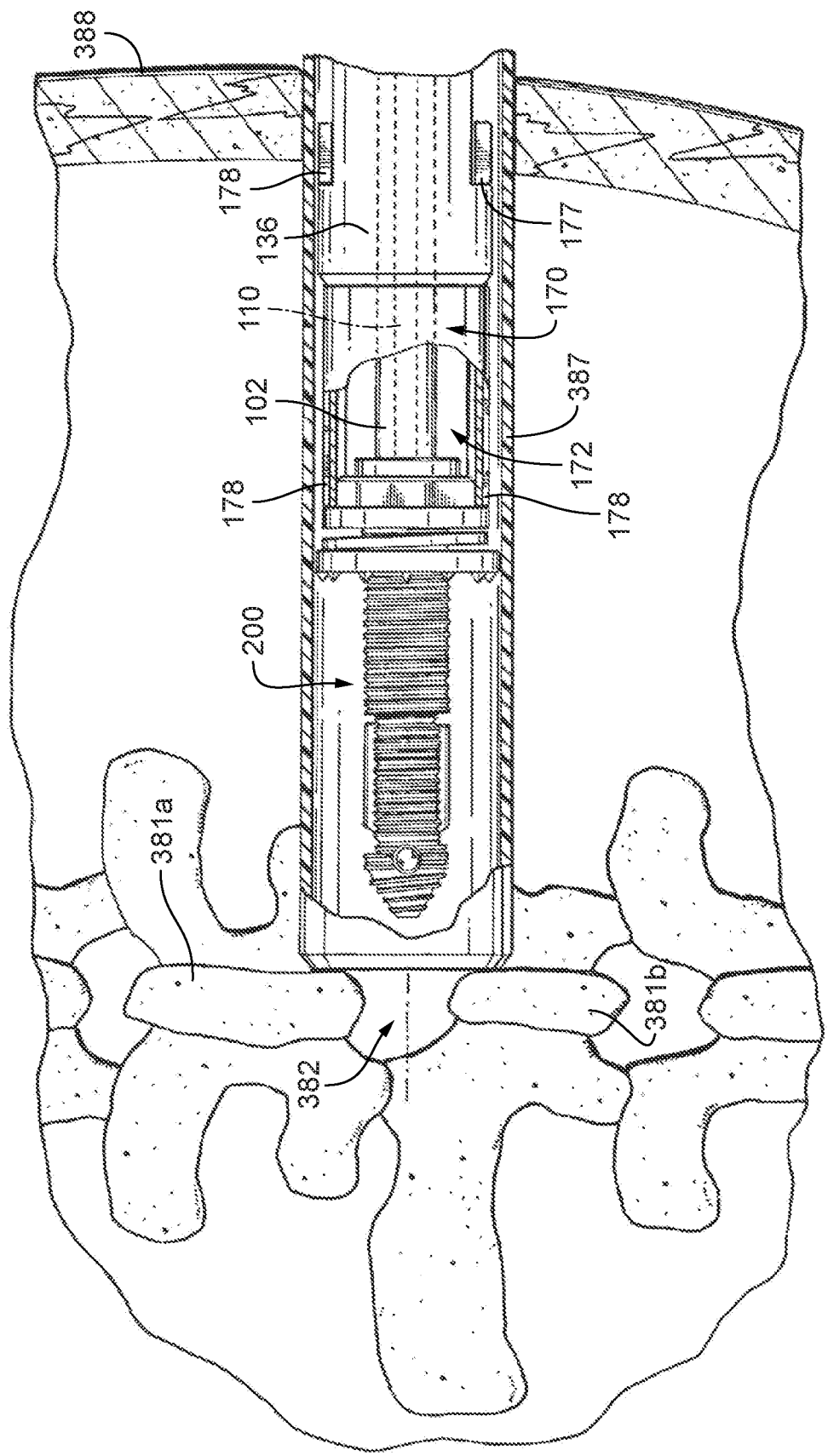
FIG. 20 is a dorsal view of an implant within an introducer tube during lateral insertion thereof.

FIG. 20 is a dorsal (rear) view of the implant 200, still held by the insertion instrument 100, within a lumen of an introducer tube 387, during lateral insertion thereof. For direct lateral insertion of the implant 200 into the target interspinous process space 382 an incision is formed in the skin 388 of a patient, and ultimately an introducer tube 387 is advanced through the tissue to the target interspinous process space 382, through which the implant 200 is advanced, connected to the insertion instrument 100.

The implant 200 is axially rotated by way of the insertion instrument 100, thus threading the implant 200 into the target interspinous process space 382, distracting the adjacent spinous processes 381a, 381b, and advancing the implant 200, generally centered with respect to the spinous processes 381a, 381b.

Figure 21:
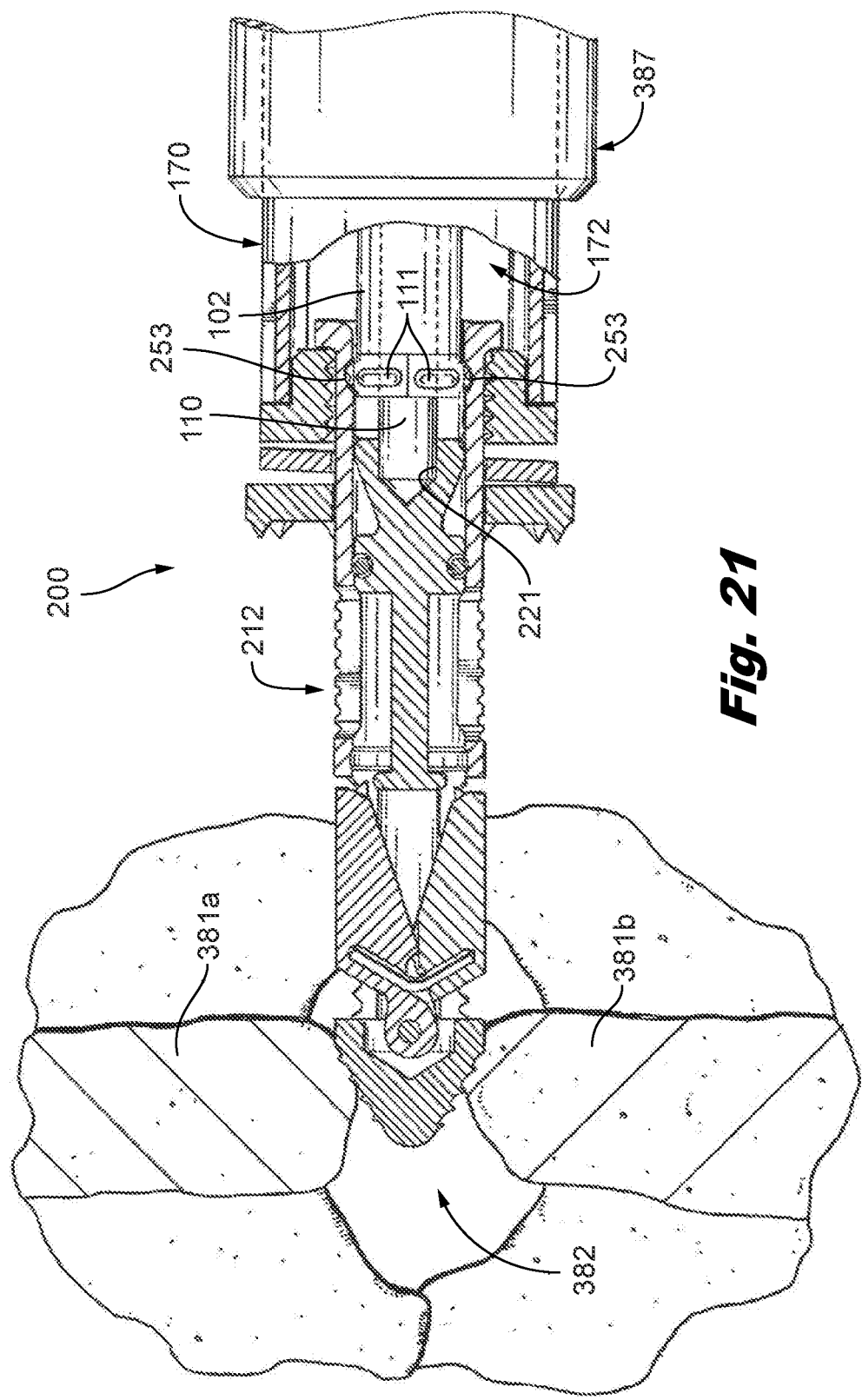
FIG. 21 is a dorsal view illustrating the implant being screwed into a target interspinous process space.

To rotate the implant 200, the handle 106 of the elongated main body 102 is rotated in a tightening or clockwise direction to self-thread the implant 200 through the interspinous space 382 as shown in FIG. 21. During the rotation of the implant 200, the implant 200 distracts the interspinous space. Relative rotation and axial translation between the implant 200 and the insertion instrument 100 is inhibited because the implant 200 is locked onto the tip 113 by the distal pushing end 112 of the plunger 110. Distraction can also be performed in advance by a separate instrument, with insertion of the implant 200 following, and maintaining such distraction.

Figure 22:
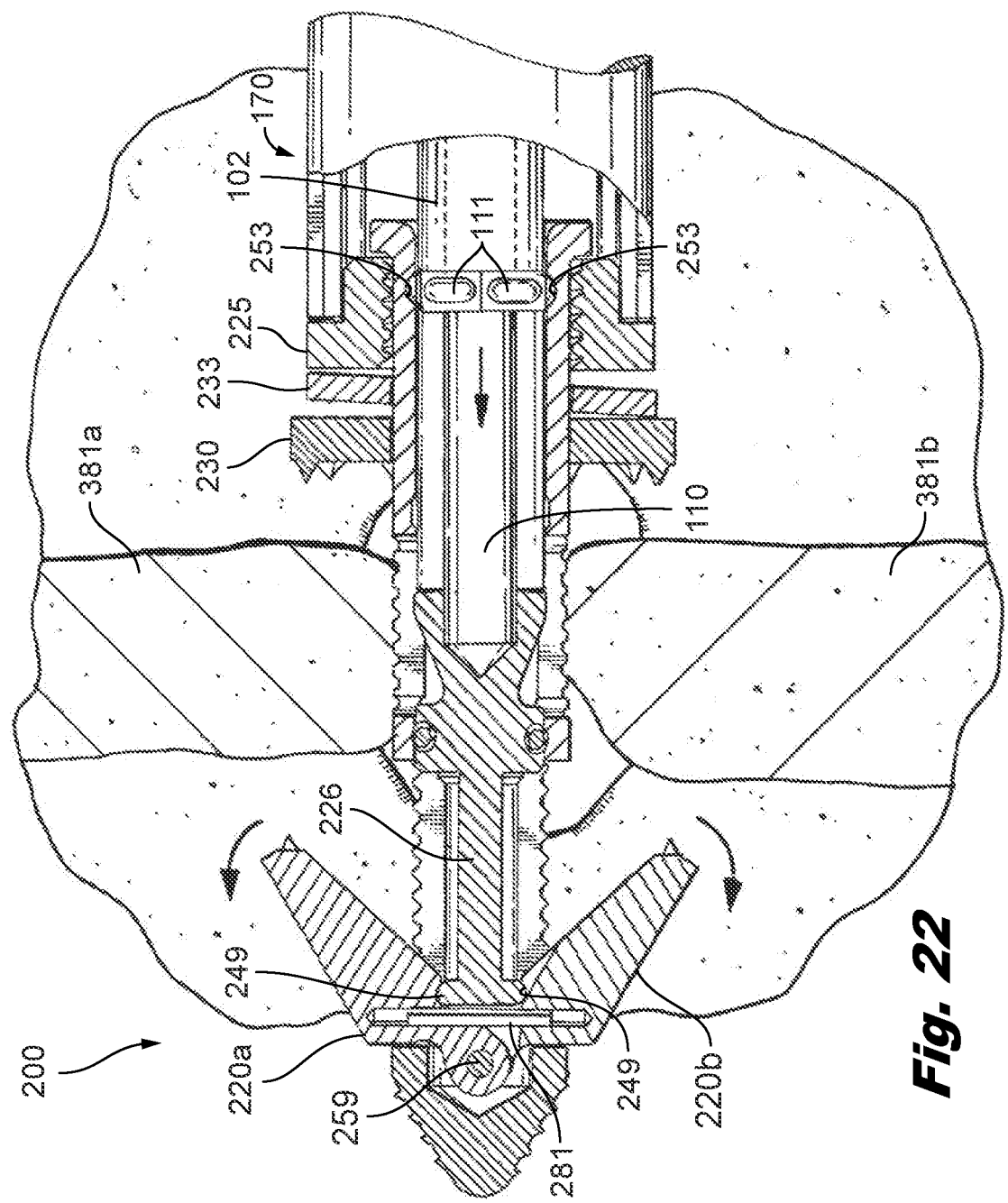
FIG. 22 is a cross-sectional view illustrating the deployment of the blades of the implant.

When anchoring blades 220a, 220b have passed through the interspinous space 382 as shown in FIG. 22, the anchoring blades 220a, 220b can be deployed.

To deploy the implant 200, the plunger tab 131 is rotated by the user from the first path 123 to the second path 125 along the transition wall 127 (best shown in FIGS. 9-12). After the plunger tab 131 is fully positioned within the second path 125, the plunger knob 130 is again rotated clockwise to continue distal movement of the plunger tab 131.

Figure 12:
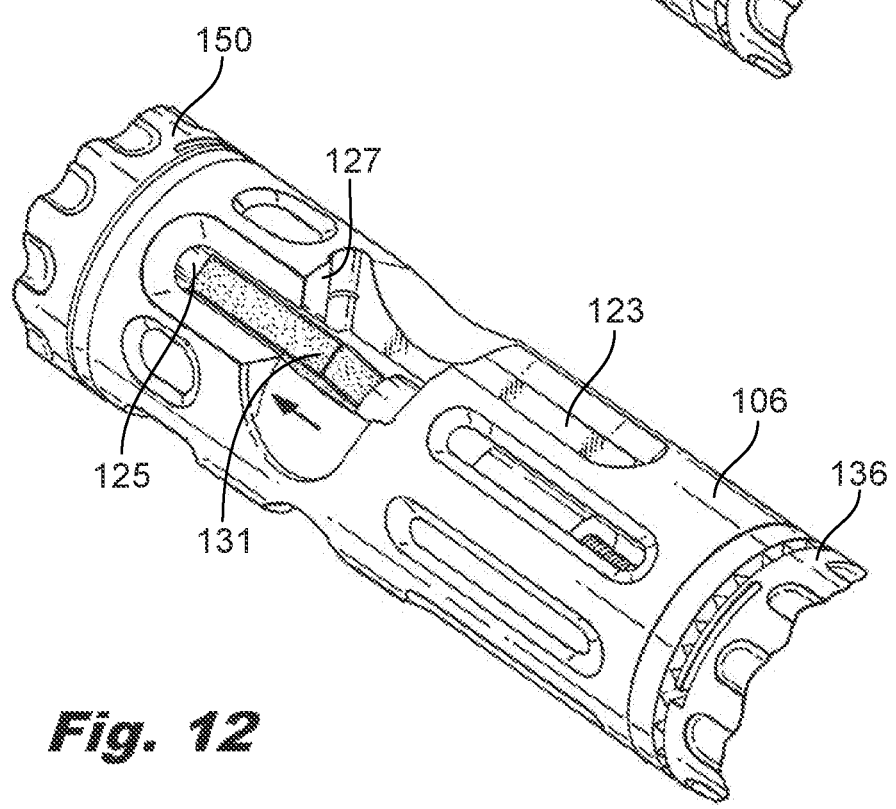
FIG. 12 is a perspective view of the handle of the insertion instrument of FIG. 1 with the plunger tab in a distal position.

As the plunger 110 continues to move distally, the distal pushing end 112 enters in the recess 221 of the implant plunger 226. As the plunger 110 continues to move distally, the distal pushing end 112 applies pressure and moves the implant plunger 226 distally to deploy the blades 220a, 220b. Once the plunger tab 131 is positioned in the distal most position of the staggered path 121 (as shown in FIG. 12), the implant is 'deployed'. The physician can also verify proper deployment of the blades 220a, 220b by fluoroscopy. Once the blades 220a, 220b are deployed, the implant 200 can be set in final position.

Figure 23:
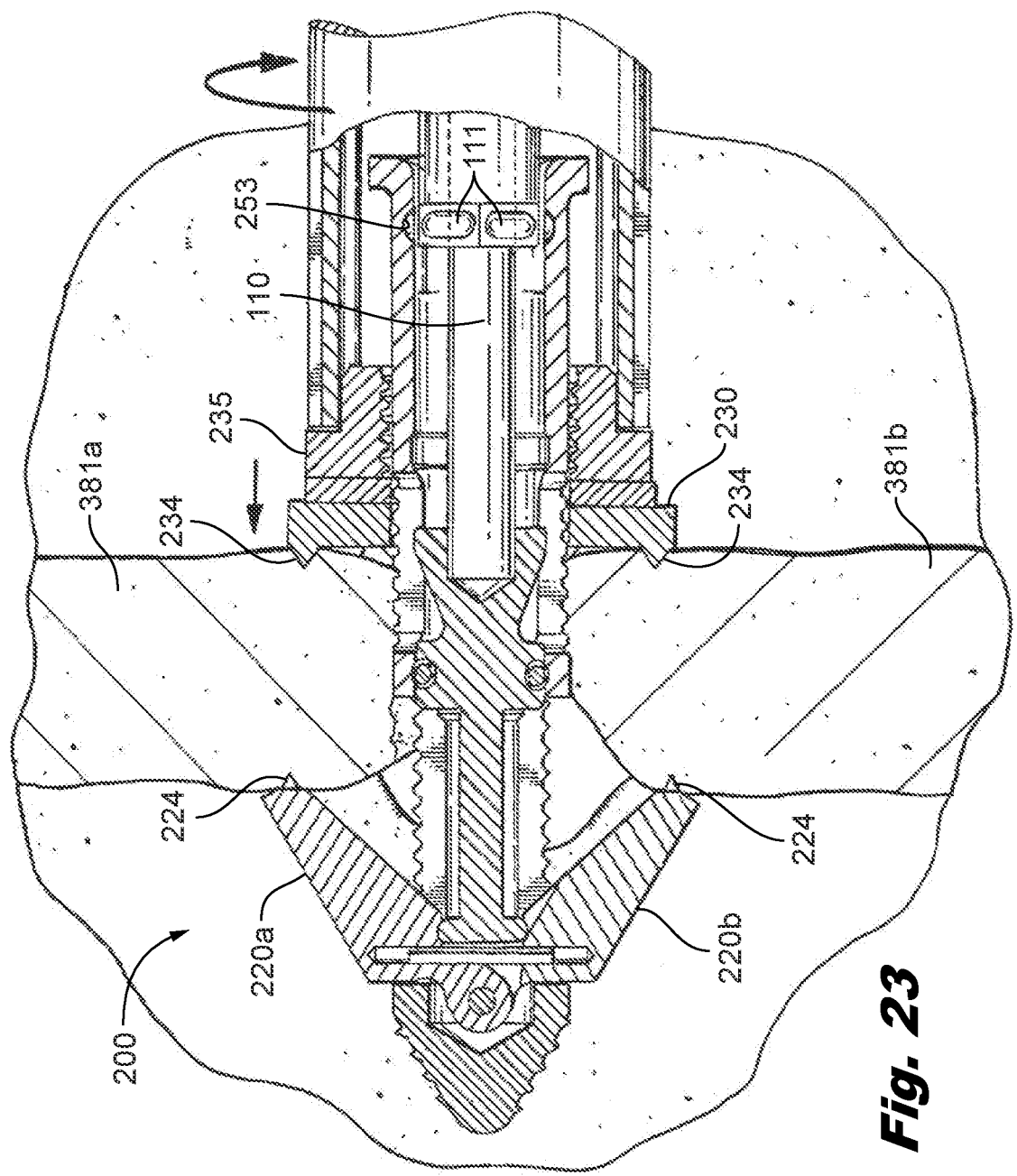
FIG. 23 is a cross-sectional view illustrating the hex nut driver securing the implant to the spinous process.

Referring now to FIG. 23, the hex nut 235 of the implant 200 is shown being driven by the hex nut driver 140 to engage the spikes 224, 234 to the spinous processes 381a, 381b. The hex nut driver 140 rotates the hex nut 235 to move the spike cap 230 distally. Because the spike cap 230 is keyed to the implant 200 to prevent rotation, as the hex nut 235 turns, the spike cap 230 slides distally.

To rotationally drive the hex nut 235, the knob 148 of the hex nut driver 140 is rotated clockwise relative to the elongated main body 102. In some embodiments, the handle 106 is held tightly while knob 148 is rotated to prevent movement of the elongated main body 102. Turning the knob 148 turns the adapter 170 and thereby the hex nut 235. Once the spike cap 230 engages the spinous processes 381a, 381b, the blades 220a, 220b are drawn proximally into engagement with the bone 381a, 381b. A flat portion of the implant 200 is not threaded so that the implant 200 slides proximally, and allows the spike cap 230 to translate linearly along the body 212 without rotation. While the hex nut driver 140 is used to tighten the hex nut 235, the surgeon can feel the spike cap 230 become fully seated or full seating is seen in an accompanying fluoroscopy display.

Once the implant 200 is properly deployed, the insertion instrument 100 is disengaged from the implant 200. To disengage the implant 200, the plunger 110 is withdrawn from the implant 200. To withdraw the plunger 110, the plunger knob 130 is loosened or rotated in the counter-clockwise direction relative to the handle 106 of the elongated main body 102 to move the plunger tab 131 proximally. As the plunger tab 131 slides proximally within the staggered path 121, the distal pushing end 112 is translated proximally.

Once the plunger tab 131 abuts the transition wall 127 the plunger tab 131 is rotated from the second path 125 to the first path 123. The plunger knob 130 is loosened or rotated in the counter-clockwise direction relative to the handle 106 of the elongated main body 102 to continue to slide the plunger tab 131 proximally. The plunger 110 is withdrawn from the tip 113 and the flexible arms 109 are again allowed to flex so that the tip 113 pops out of the proximal internal recess 250 of the implant 200. With the plunger 110 retracted to the unlocked position, the coupling force of the tip 113 to the implant 200 can be overcome to fully detach the insertion instrument 100. In some embodiments, the force of spring 163 may aid in the detachment of the tip 113 from the implant 200 by biasing the drive shaft 160 away from the implant 200. Once removed, the insertion instrument 100 can be removed from the patient for disassembly, cleaning, and re-use.

Disassembly of the Insertion Instrument

It is advantageous to disassemble the insertion instrument 100 for cleaning. Referring to FIGS. 3-10 in reverse, the plunger 110 can be removed from the elongated main body 102. The plunger knob 130 can be unscrewed from the plunger 110. The elongated main body 102 can be removed from the hex nut driver 140. The adapter 170 can be unsnapped from the hex nut driver 140. At this point, the components of the insertion instrument 100 are ready to be cleaned.

Additional Embodiment

Figure 24:
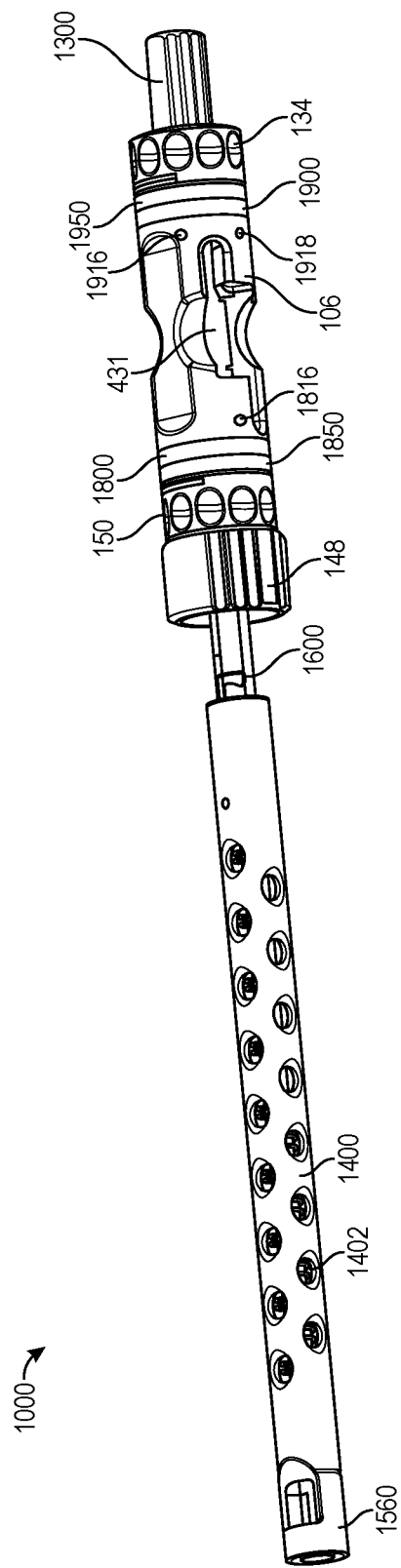
FIG. 24 is a perspective view of a second embodiment of the insertion instrument.

Illustrated in FIGS. 24-41 is an additional embodiment of an insertion instrument 1000. With reference to FIG. 24, similar to aforementioned embodiments, insertion instrument 1000 comprises handle 1060, knob 148, and plunger tab 431, as well as other components described above. As described above with reference to FIGS. 13-15, plunger tab 431 may instead be plunger tab 131 or plunger tab 331 in insertion instrument 1000. In some embodiments of insertion instrument 1000, the knob 148 operatively engages a proximal drive shaft 1600 rather than a hex nut driver 140, as described previously.

In some embodiments, the insertion instrument 1000 includes the proximal drive shaft 1600 located proximally of a distal hex nut driver 1400. The distal hex nut driver 1400 defines an axial passage 1440 extending therethrough. The distal hex nut driver 1400 terminates at the distal end in a socket end 1560. The socket end 1560 is tubular but forms a shaped opening 1580, which may be square, hexagonal, or any other shape to provide anti-rotation engagement, for coupling, either directly or indirectly, to the implant 200 or the adapter 170. The socket end 1560 also forms a transverse locking passage 1570, which may be square, hexagonal, or any other shape to provide anti-rotation engagement. Distal hex nut driver 1400 may also include openings 1402 within the walls to reduce the weight of the element or to assist with cleaning of the instrument.

The axial passage 1440 of the distal hex nut driver 1400 is configured to receive the distal section of the proximal drive shaft 1600. For example, with reference to FIGS. 24-27, an elongated main body 1020 may be received within the proximal drive shaft 1600 and the distal end and tip 1130 of the elongated main body 1020 may extend distally therefrom. Distal to the proximal drive shaft 1600, a spring 1630 may surround a portion of the elongated main body 1020 that extends distally from the proximal drive shaft 1600. Subsequently, in some embodiments, the axial passage 1440 of the distal hex nut driver 1400 may receive the spring 1630, a portion of the elongated main body 1020, and a distal portion of the proximal drive shaft 1600.

In some embodiments, the distal hex nut driver 1400 is secured to and operatively engages the proximal drive shaft 1600. This may be accomplished by fastening pins 1650 through one or more pin holes 1467. As can be seen from FIG. 25, the pins 1650 may be configured to insert into complementary slots 1610 in proximal drive shaft 1600 when insertion instrument 1000 is assembled.

Figure 25:
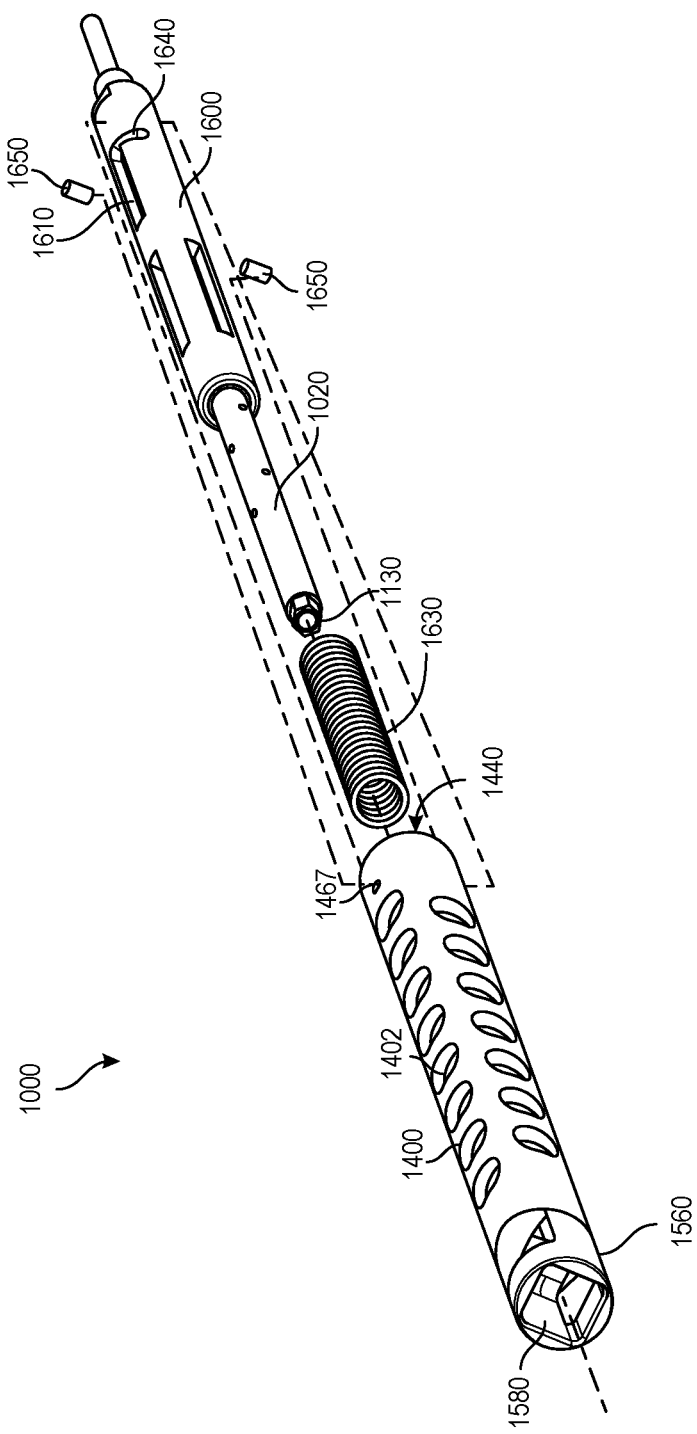
FIG. 25 is an exploded view of components of the insertion instrument of FIG. 24, in some embodiments.

Additionally, when fully assembled, the tip 1130 of elongated main body 1020 may extend into the socket end 1560, terminating near opening 1580 (see FIG. 25). Similar to the description above, tip 1130 may be configured to operatively engage an implant 200. As will be described below, displacement of the distal hex nut driver 1400 may reveal tip 1130, such that a user may secure the implant 200 to tip 1130. In some embodiments, tip 1130 may be replaceable. For example, tip 1130 may be removably attached to elongated main body 1020 such that it may not become dislodged during a surgical procedure. However, following the procedure, a user may remove a used tip 1130 and replace it with a new tip 1130.

Figure 26:
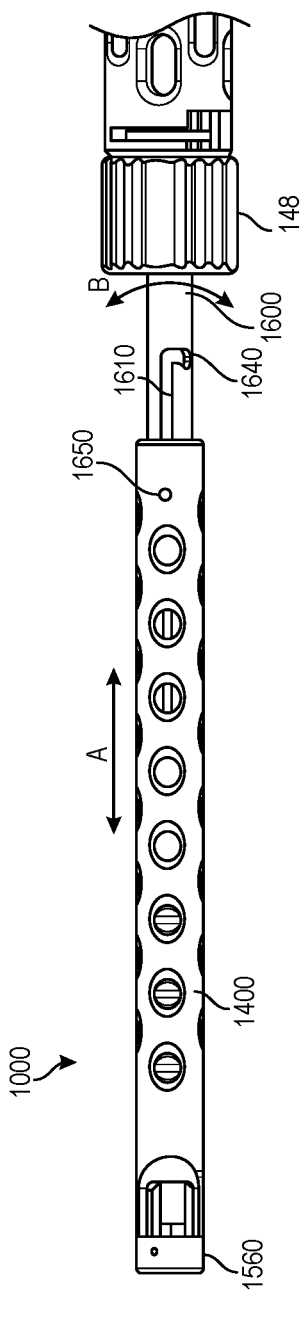
FIG. 26 is a side view of some embodiments of the insertion instrument of FIG. 24 in an extended configuration.
Figure 27:
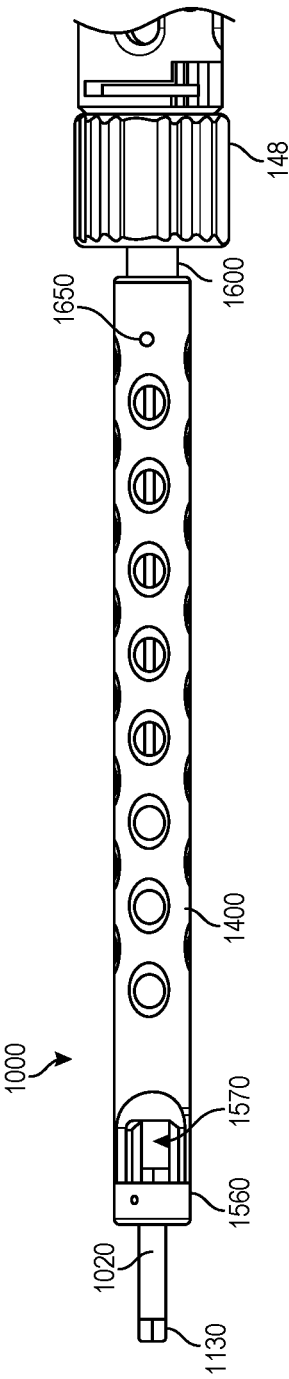
FIG. 27 is a side view of some embodiments of the insertion instrument of FIG. 24 in a retracted configuration.

Referring now to FIGS. 26 and 27, operation of the distal hex nut driver 1400 and proximal drive shaft 1600 is discussed. As mentioned above, the positioning of the distal hex nut driver 1400 in relation to the proximal drive shaft 1600 may allow for the tip 1130 of the elongated main body 1020 to be accessible. For example, when fully assembled, the pins 1650 may be received by complementary slots 1610. As depicted in FIG. 26, this may allow for movement of distal hex nut driver 1400 along a longitudinal direction (e.g., direction A). It will be noted that in some embodiments, spring 1630 biases the distal hex nut driver 1400 in the distal direction in comparison to the proximal drive shaft 1600 (i.e., away from proximal drive shaft 1600). Therefore, to adjust distal hex nut driver 1400 along direction A in the proximal direction, a user must overcome the force of spring 1630.

In some embodiments, complementary slots 1610 disposed on proximal drive shaft 1600 may comprise a radial portion 1640. Accordingly, once distal hex nut driver 1400 is moved substantially along direction A, the pins 1650 may abut radial portion 1640, thus preventing further movement along direction A. Once stopped, a user may twist distal hex nut driver 1400 along direction B, such that pins 1650 travel along and inside radial portion 1640. As shown in FIG. 27, such a movement of the distal hex nut driver 1400 may distally extend the tip 1130 of the elongated main body 1020. Additionally, by placing pins 1650 in the radial portion 1640, the distal hex nut driver 1400 is secured in the retracted position.

By placing the distal hex nut driver 1400 in the secured position, as shown in FIG. 27, a user may place an adapter (e.g., adapter 170) over the distal portion 108 of the elongated main body 1020 so that the legs 175, 176 can be inserted into the opening 1580. In some embodiments, the locking tabs 177 provide an audible click when the legs 175, 176 deflect outward into the transverse locking passage 1570 to confirm positive engagement for the user.

After positioning the adapter 170 on the distal hex nut driver 1400, the implant 200 may be partially engaged to the tip 1130 by a snap friction fit. In some embodiments, the tip 1130 is slightly compressed, by virtue of the flexible arms 109, and passed into the proximal internal recess 250 of the implant 200 with the blades 220*a*, 220*b* of the implant 200 aligned with the flexible arms 109 of the elongated main body 1020. As a result, the user can determine proper blade orientation visually prior to and during insertion. The tip 1130 stops within the proximal internal recess 250 when the ridges 111 seat into the transverse groove 253. At this point, the implant 200 is coupled to the insertion instrument 1000 but not yet "locked."

In some embodiments, to lock the implant 200 to the insertion instrument 1000, the plunger 110 is moved from the unlocked position to the locked position. To move the plunger 110 distally, the exchangeable plunger knob 1300 is rotated clockwise (looking from the proximal end) until the plunger tab 131 rests adjacent the transition wall 127, as shown in FIGS. 9 and 10. The distal pushing end 112 of the plunger 110 is approximately flush with the tip 1130 of the elongated main body 1020. Thus, the flexible arms 109 of the elongated main body 1020 can no longer flex out of the transverse groove 253. Consequently, the implant 200 is tightly coupled and locked to the tip 1130 so that inadvertent removal does not occur. The insertion instrument 1000 is now ready to have the socket end 1560 of the distal hex nut driver 1400 engaged to the hex nut 235 of the implant 200.

To engage the distal hex nut driver 1400 to the hex nut 235 of the implant, the knob 148 is held to prevent rotation while the distal hex nut driver 1400 is rotated to bring the pins 1650 out of the radial portions 1640 and into the complementary slots 1610. The spring 1630 will bias the distal hex nut driver 1400 outward so care should be taken to slowly extend the distal hex nut driver 1400 to have the hex socket 172 properly engage the hex nut 235, a slight manual rotation or jiggle of the distal hex nut driver 1400 may be required. The implant 200 is now locked to the insertion instrument 1000 to be ready for spinal implantation.

The particular arrangement of components of insertion instrument 1000 may provide certain advantages to a user while operating the device. For example, in the configuration of FIGS. 24-27, a user may be able to access the proximal drive shaft 1600 while the insertion instrument 1000 is in use from outside the body. As described earlier with reference to FIG. 20, when operating insertion instrument 1000 inside of the introducer tube 387, the user has access to the proximal drive shaft 1600 and distal hex nut driver 1400. This allows the user to adjust the distal hex nut driver 1400 in relation to the proximal drive shaft 1600 while functioning. For instance, the user may adjust the positioning of pins 1650 along complementary slots 1610 or radial portion 1640 during use.

In one example, during an operation, the tissue of a patient may displace the adapter 170 from the hex nut 235. In such a case, having the distal hex nut driver 1400 accessible to the user may allow the user to manipulate the distal hex nut driver 1400 to re-engage the adapter 170 and the hex nut 235. In another example, if a user forgets to engage the distal hex nut driver 1400 with the hex nut 235 before insertion into the patient, they can still correct this during the procedure. In this example, if the implant 200 is partially threaded into tissue of a patient while operatively connected to the insertion instrument 1000, the user may access the distal hex nut driver 1400 during operation to engage the hex nut 235. Such access allows the user to maintain the coupling of the implant 200 to the insertion instrument 1000 throughout the operation. This avoids the user from having to withdraw the entire inserter and implant and restart the procedure entirely.

Figure 28:
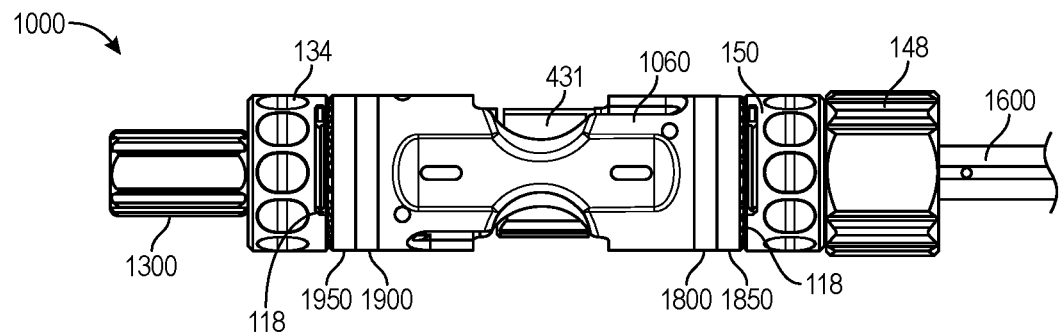
FIG. 28 is a side view of some embodiments of the insertion instrument of FIG. 24 showing a plunger knob.
Figure 29:
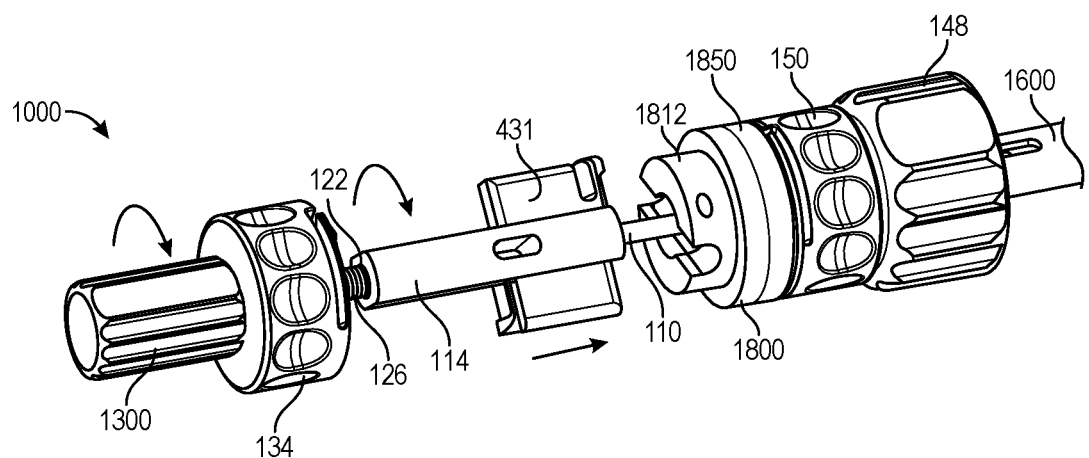
FIG. 29 is a side perspective view of some embodiments of the insertion instrument of FIG. 24 showing connectivity of some components.

FIGS. 28-29 illustrate some embodiments of an exchangeable plunger knob 1300 of insertion instrument 1000. Similar to the plunger knob 130 shown in FIG. 5, the exchangeable plunger knob 1300 is coupled to the locking cap 114 of the plunger 110. In some embodiments, the exchangeable plunger knob 1300 includes a threaded core 126 that is rotated into a recess 122 of the locking cap 114. In some embodiments, the threaded core 126 and recess 122 comprise complementary quad lead threads, thereby allowing rotation of the exchangeable plunger knob 1300 to translate to axial movement of plunger tab 431 and plunger 110 more efficiently. Thus, the exchangeable plunger knob 1300 is involved in deployment of the implant 200 as described above through axial movement of the plunger 110. Further, in some embodiments one or more of the plunger 110, the plunger tab 431, the elongated main body 1020, the tip 1130, and other components are coated in a biocompatible, corrosion resistant material to help protect and/or strengthen the component. For example, some or all portions of insertion instrument 1000 may be advantageously reinforced with a coating material to increase the durability of the components while maintaining safety to the patient by the coating material being of a biocompatible substance. Such a coating material may be applied specifically to components of insertion instrument 1000 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 2000™. In some embodiments, the coating material may be applied to the entirety of the plunger 110 and the plunger tab 131, 331, 431. In some embodiments, the thickness of the coating material may be between about 1 μm to about 15 μm. In some embodiments, the coating material may be between about 2 μm to about 10 μm. To deploy the implant 200, the handle 1060 is rotated to translate the plunger tab 131 from the first path 123 to the second path 125 along the transition wall 127 (best shown in FIGS. 9-12). After the plunger tab 431 is fully positioned within the second path 125, the exchangeable plunger knob 1300 is again rotated clockwise to continue distal movement of the plunger tab 431 and plunger 110, as illustrated in FIG. 29.

As the plunger 110 continues to move distally, the distal pushing end 112 enters in the recess 221 of the implant plunger 226. As the plunger 110 continues to move distally, the distal pushing end 112 applies pressure and moves the implant plunger 226 distally to deploy the blades 220a, 220b. Once the plunger tab 431, 131 is positioned in the distalmost position of the staggered path 121 (as shown in FIG. 12), the implant is 'deployed'.

As described above, rotation of the exchangeable plunger knob 1300 is directly translated into axial movement of the plunger 110, which then translates into outward rotation of blades 220a, 220b (as shown in FIG. 22). Due to this motion, the size (i.e., diameter) of exchangeable plunger knob 1300 directly relates to the relative force of the axial movement of plunger 110 and blades 220a, 220b. In some embodiments, the diameter of exchangeable plunger knob 1300 may be adjusted based on the necessary force to deploy blades 220a, 220b. For example, an increase in the diameter of exchangeable plunger knob 1300 will translate a higher axial force to the blades 220a, 220b of the implant 200. Similarly, less rotational force is needed for the increased diameter exchangeable plunger knob 1300 to exert equal axial force of blades 220a, 220b in comparison to a smaller diameter exchangeable plunger knob 1300.

Thus, in some embodiments, the size of exchangeable plunger knob 1300 may be adjusted based on the type of surgery or the size of the implant being performed. For example, if there is greater amounts or density of tissue in which blades 220a, 220b are to be deployed, then the diameter of exchangeable plunger knob 1300 may be increased to decrease the necessary applied force applied to exchangeable plunger knob 1300 to deploy the blades 220a, 220b (e.g., decrease the force required by the physician to turn exchangeable plunger knob 1300). In another example, the size/age of the patient may be decreased and therefore decrease the amount/density of tissue in which blades 220a, 220b are to be deployed. In this example, it may be advantageous to decrease the diameter of exchangeable plunger knob 1300 so as to increase the applied force required to deploy blades 200a, 200b. In this example, decreasing the diameter of exchangeable plunger knob 1300 may prevent the physician from accidentally applying too much force to exchangeable plunger knob 1300, thereby deploying the blades 220a, 220b too far in the outward direction which may cause unnecessary tissue scarring/damage.

In yet further embodiments, the size of exchangeable plunger knob 1300 may be adjusted based on the size and shape of blades 200a, 220b and/or implant 200. For example, if blades 220a, 220b are longer, then more applied force may be required to deploy the blades 220a, 220b through tissue. Thus, the diameter of the exchangeable plunger knob 1300 may be increased to decrease the applied force required to deploy blades 220a, 220b. The above are just some examples as to when the diameter of exchangeable plunger knob 1300 may be adjusted. It is contemplated that many other situations encountered by a physician may be advantageous to similarly adjust the diameter of exchangeable plunger knob 1300. For exemplary purposes, in some embodiments, the diameter of the exchangeable plunger knob 1300 may be between about 5 mm to about 30 mm. In some embodiments, the diameter of the exchangeable plunger knob 1300 may be between about 8 mm to about 20 mm. In some embodiments, the diameter of the exchangeable plunger knob 1300 may be between about 12 mm and about 16 mm.

In some embodiments, it may be advantageous to replace some components of insertion instrument 1000 that experience greater force than others. For example, as will be described in greater detail below, the elongated main body 1020 may experience a greater amount of torsional force when inserting/deploying implant 200. This greater amount of action on the elongated main body 1020 may increase the likelihood of damage to certain portions of the elongated main body 1020 (e.g., tip 1130) while leaving some or all of the other components of insertion instrument 1000 in good operating condition. Below, some embodiments will be discussed in greater detail that allow for the replacement of the elongated main body 1020 while maintaining the other components of insertion instrument 1000. Additionally, some embodiments may include aspects of certain components that increase the durability of components of insertion instrument 1000 when encountering regular, high levels of torsional force.

Figure 30:
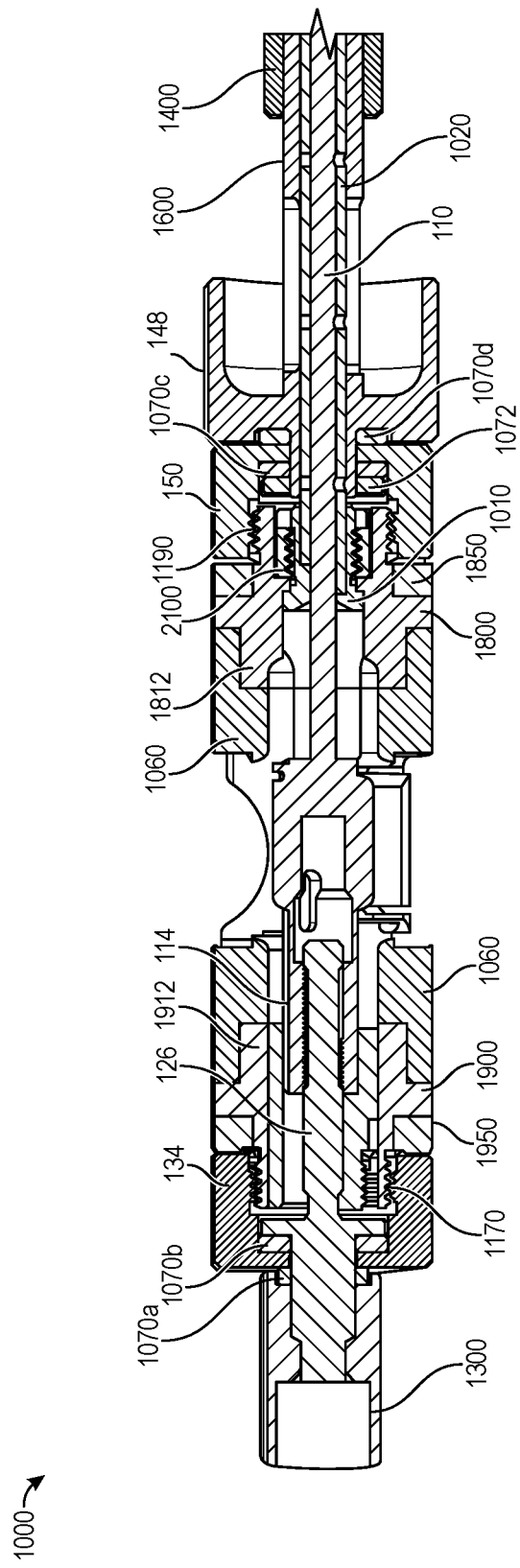
FIG. 30 is a side cross-sectional view of some embodiments of the insertion instrument of FIG. 24.

FIG. 30 illustrates a cross sectional view of some embodiments of insertion instrument 1000. In some embodiments, handle 1060 is operatively connected to a medial housing 1800 and a proximal housing 1900. As will be discussed further below with reference to FIG. 31, in some embodiments the medial housing 1800 and proximal housing 1900 may be connected to the handle 1060 by pins inserted into holes located in handle 1060.

In some embodiments, the proximal housing 1900 and the medial housing 1800 are mechanically coupled to end caps 134 and 150, respectively. For example, differing from insertion instrument 100, proximal housing 1900 and medial housing 1800 comprise a proximal threaded feature 1170 and distal threaded feature 1190 extending therefrom. In some embodiments, the proximal threaded feature 1170 may be configured to threadably engage end cap 134. In some embodiments, the distal threaded feature 1190 may be configured to threadably engage end cap 150.

In some embodiments, portions of the proximal housing 1900 and the medial housing 1800 are separated from the end caps 134, 150 by a proximal ring 1950 and a medial ring 1850, respectively. In some embodiments, as illustrated in FIG. 28, the proximal ring 1950 and medial ring 1850 include ratchet teeth 118 directed towards the end cap 134 and 150, respectively. As discussed above with reference to FIG. 7, the ratchet teeth 118 in some embodiments are configured to aid in the connection to end caps 134, 150 via flexible tabs 136 and teeth 136a, 152a.

In some embodiments, one or more bearings may be disposed within a portion or portions of insertion instrument 1000 to allow for separate rotation of different components in relation to one another. For example, in some embodiments bearing 1070a may be placed between exchangeable plunger knob 1300 and end cap 134 to allow the rotation of exchangeable plunger knob 1300 in relation to end cap 134. In some embodiments, bearing 1070b may be disposed on the inner portion of end cap 134 and operatively engaging a portion of the threaded core 126. Similar to bearing 1070a, bearing 1070b may aid in the rotation of exchangeable plunger knob 1300, and threaded core 126, in relation to end cap 134. In some embodiments, insertion instrument 1000 may include bearing 1070c and bearing 1070d, which are configured to allow rotation of knob 148 with respect to handle 1060. In some embodiments, bearings 1070c, 1070d may be kept in place by a washer cap 1072. Such placement of bearings 1070c and 1070d may be advantageous, for example, when rotating knob 148 to drive rotation of the hex nut 235 and axial movement of the spike cap 230.

Figure 31:
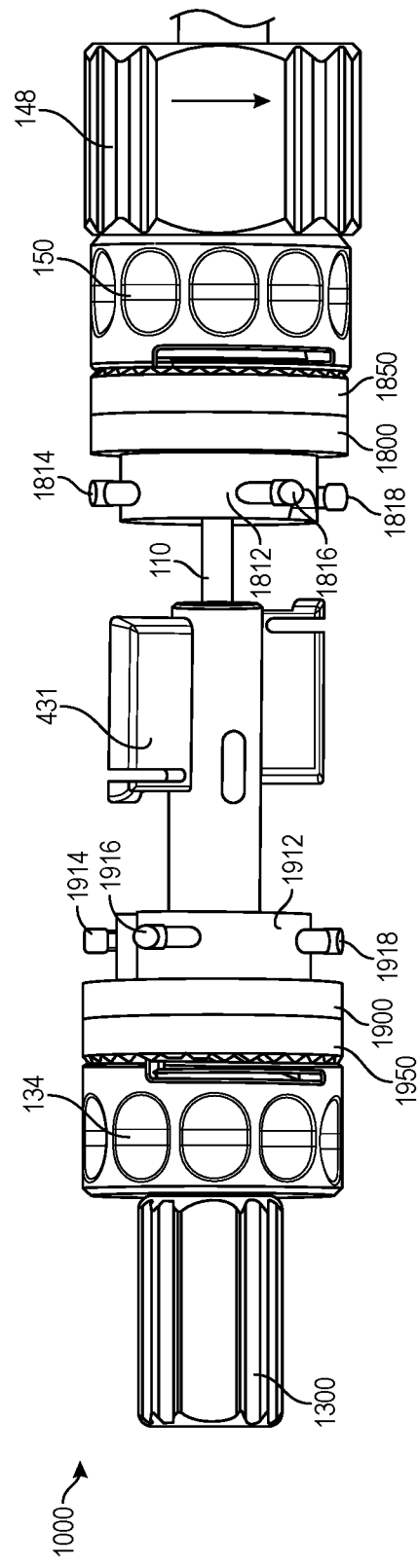
FIG. 31 is a side view of some embodiments of the insertion instrument of FIG. 24 with the handle hidden.

FIG. 31 illustrates some embodiments of insertion instrument 1000 with the handle 1060 hidden such that connective portions of the proximal housing 1900 and medial housing 1800 are visible. For example, in some embodiments proximal housing 1900 and medial housing 1800 include handle engagement walls 1912 and 1812, respectively. As illustrated in FIG. 30, in some embodiments, portions of handle engagement walls 1912 and 1812 are received within handle 1060. In some embodiments, handle engagement walls 1912, 1812 comprise one or more handle pins. Illustrated for exemplary purposes, proximal housing 1900 includes handle pins 1914, 1916, and 1918, and medial housing 1800 includes handle pins 1814, 1816, and 1818. The one or more handle pins are configured to extend from either or both of the proximal housing 1900 and the medial housing 1800 through holes located in handle 1060. Accordingly, any movement (e.g., rotational movement) will be translated from handle 1060 to proximal housing 1900 and medial housing 1800 via the handle pins. While three handle pins are illustrated here, it will be understood that any number of handle pins may be used to operatively connect the proximal housing 1900 and medial housing 1800 to the handle 1060. For example, one, two, three, four, five, six, seven, eight, or more handle pins may be used to operatively connect the proximal and medial housings 1900/1800 to the handle 1060.

Figure 32:
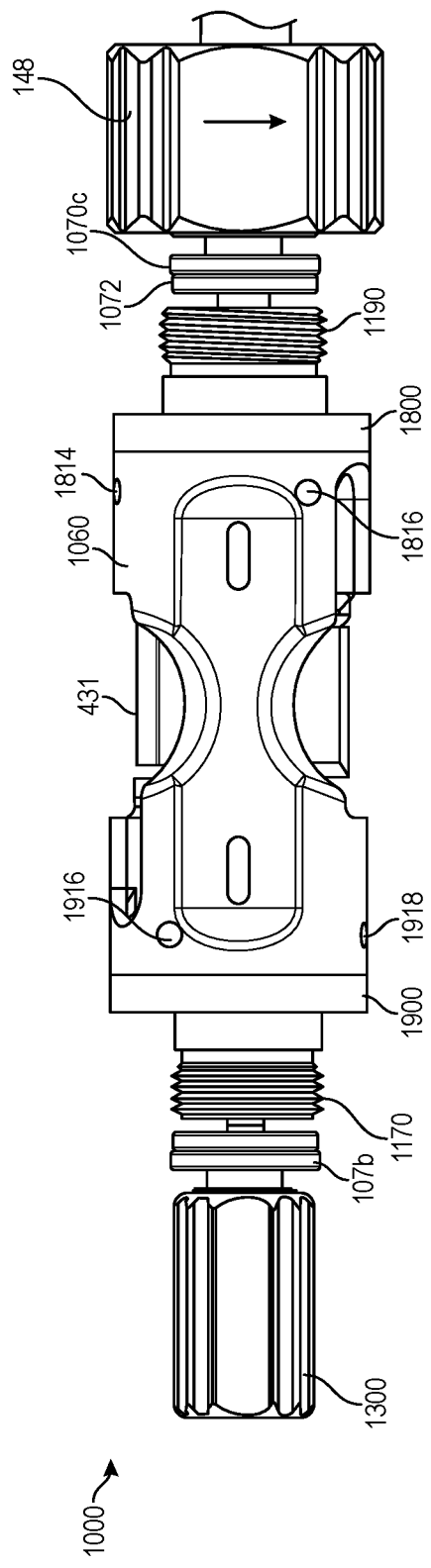
FIG. 32 is a side view of some embodiments of the insertion instrument of FIG. 24 showing threaded features.

FIG. 32 illustrates some embodiments of insertion instrument 1000 with the end caps 134/150, medial ring 1850 and proximal ring 1950 hidden. As mentioned above with reference to FIG. 30, the proximal housing 1900 may include a proximal threaded feature 1170 extending proximally. As illustrated in FIG. 30, end cap 134 may include an inner threaded portion configured to threadably receive the proximal threaded feature 1170 of proximal housing 1900. Similarly, in some embodiments, medial housing 1800 may include distal threaded feature 1190 extending distally. As illustrated in FIG. 30, end cap 150 may include an inner threaded portion configured to threadably receive the distal threaded feature 1190 of medial housing 1800. While end caps 134/150 are illustrated here as threadably connected to proximal and medial housings 1900/1800, it is contemplated that any method of operatively engaging these components may be used.

Also illustrated in FIG. 32 is the extension of handle pins 1916, 1918, 1814, and 1816 through holes located in handle 1060. In some embodiments, the ends of handle pins 1916, 1918, 1814, 1816, and any others may be shaped to conform to the outer shape of handle 1060. For example, the end of handle pin 1918 may be slightly curved such that a user gripping handle 1060 will not notice the difference between the surface of handle 1060 and the end of handle pin 1918. The same may be true of any or all of handle pins 1914, 1916, 1918, 1814, 1816, and/or 1818, or any other handle pins that may be present.

Figure 33:
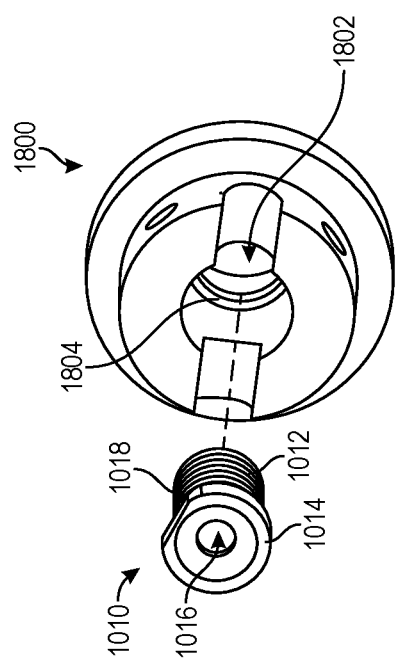
FIG. 33 is an exploded perspective proximal view of some components of a locking system of the insertion instrument of FIG. 24, in some embodiments.

FIGS. 33-36 illustrate embodiments of components of a locking system 2000 (best illustrated together in FIGS. 37-39) of insertion instrument 1000, and are best viewed together for the following description. In some embodiments, locking system 2000 includes a hub 1010 and medial housing 1800. In some embodiments, hub 1010 includes a distal threaded portion 1012 and a flange head 1014 defining a bore 1016 therethrough. In some embodiments, the flange head 1014 may include a planar side 1018, that gives the flange head 1014 an "D" shape, the planar side 1018 configured to abut an internal planar wall 1806 of the medial housing 1800. As illustrated in FIG. 33, the hub 1010 is configured to be received by a central bore 1802 of the medial housing 1800. As such, the distal threaded portion 1012 will extend through the central bore 1802 of the medial housing 1800 while the flange head 1014 will abut a flange wall 1804. The interaction of the flange head 1014 with the flange wall 1804 prevents further distal movement of the hub 1010 through the medial housing 1800.

Figure 34:
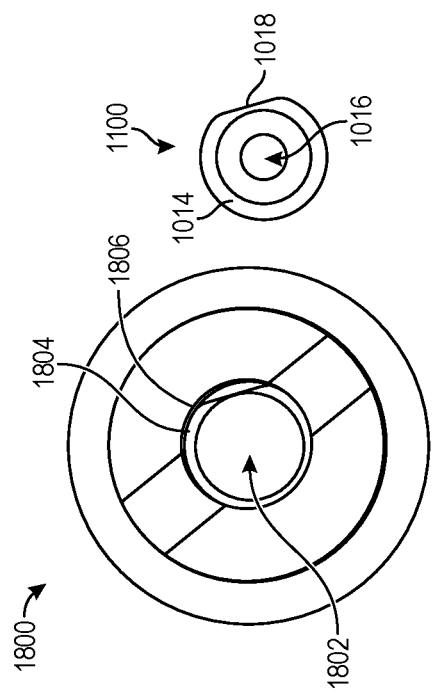
FIG. 34 is a front proximal view of some components of the locking system of the insertion instrument of FIG. 24, in some embodiments.

As mentioned above, and best illustrated in the front proximal views of the hub 1010 and the medial housing 1800 in FIG. 34, the medial housing 1800 in some embodiments includes an internal planar wall 1806. The internal planar wall 1806 is configured to abut the planar side 1018 of the hub 1010. This configuration allows for more efficient and stable force transfer when the handle 1060 and thus medial housing 1800 are rotated. As discussed above, this aids in rotation of the elongated main body 1020 and thus insertion of the implant 200 into the target interspinous process space 382.

Figure 35:
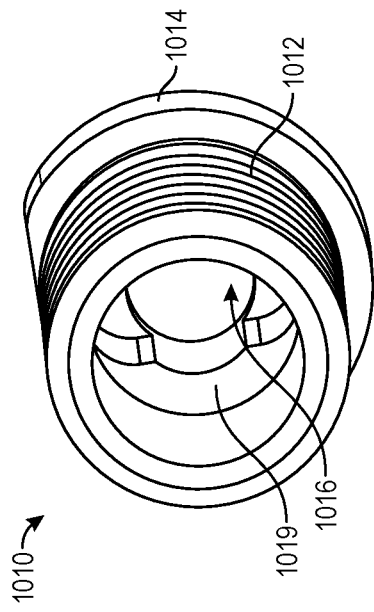
FIG. 35 is a perspective distal view of a hub of the insertion instrument of FIG. 24, in some embodiments.
Figure 36:
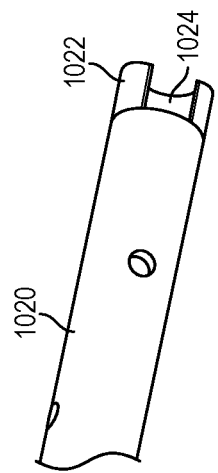
FIG. 36 is a side view of a proximal end of an elongated main body of the insertion instrument of FIG. 24, in some embodiments.

As illustrated in FIG. 35, a distal prospective view of the hub 1010 is shown in which the distal side of bore 1016 includes an elongated main body lock 1019 that is configured to be received by an indent 1024 of the elongated main body 1020 shown in FIG. 36. Additionally, in some embodiments, the elongated main body 1020 comprises an extension 1022 that is configured to extend beyond the elongated main body lock 1019. Extension 1022 extends circumferentially around a portion of the outer surface, such that an opening remains. The extension 1022 is configured to directly abut the walls of the elongated main body lock 1019. Similar to the planar side 1018 and internal planar wall 1806, the interaction between the elongated main body lock 1019 and the extension 1022 located on the proximal end of the elongated main body 1020 is configured to translate rotational movement more efficiently and sturdily between the hub 1010 and the elongated main body 1020.

Figure 37:
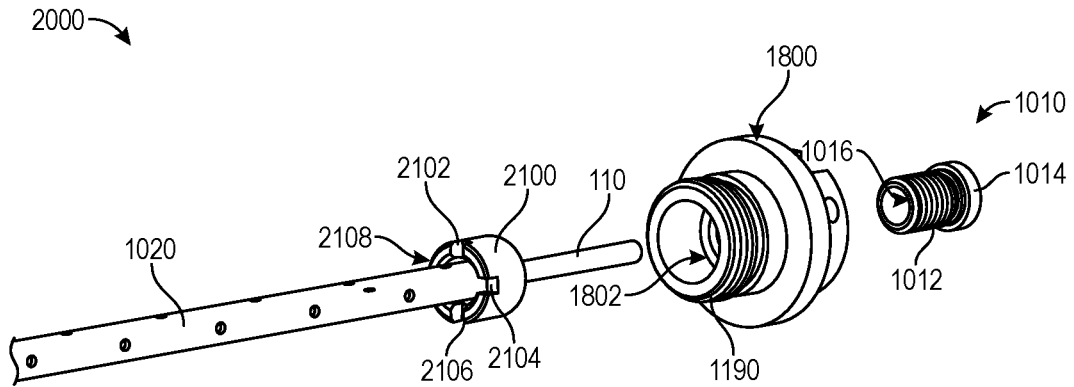
FIG. 37 is an exploded perspective view of the locking system of the insertion instrument of FIG. 24, in some embodiments.
Figure 38:
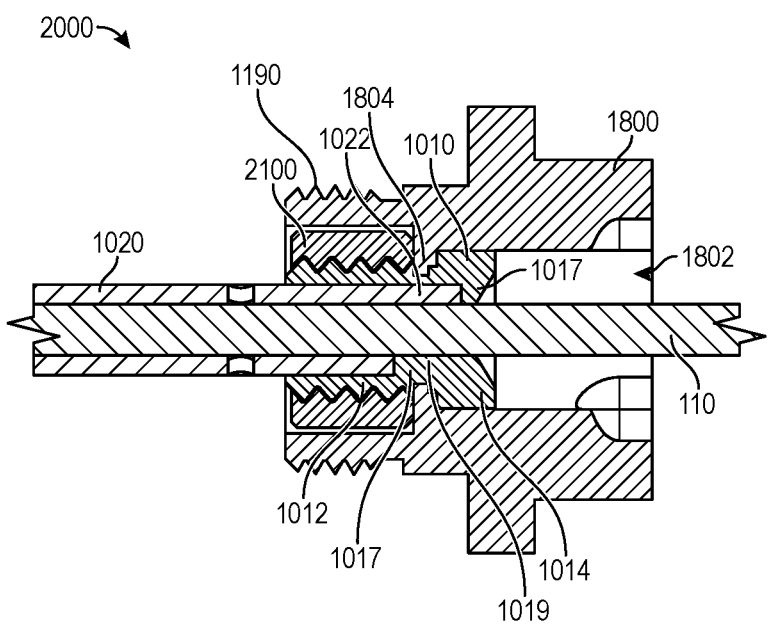
FIG. 38 is a cross sectional view of the locking system of the insertion instrument of FIG. 24, in some embodiments.

FIG. 37 illustrates an exploded distal perspective view of some embodiments of the locking system 2000 (with certain elements not shown for clarity). FIG. 38 illustrates a cross-sectional view locking system 2000 in the locked configuration. As such, FIGS. 37-38 are best viewed together for the following description. As illustrated, in some embodiments, the medial housing 1800 is configured to receive the hub 1010 through the central bore 1802. In some embodiments, the bore 1016 of the hub 1010 is configured to receive the plunger 110 therethrough and a proximal portion of the elongated main body 1020 that may not extend therethrough.

As best illustrated in FIG. 38, the flange head 1014 of the hub 1010 abuts the flange wall 1804 of the medial housing 1800, thereby preventing further distal movement of the hub 1010. In some embodiments, the distal threaded portion 1012 extends distally from the flange wall 1804 and is configured to operatively connect with a lock nut 2100.

In some embodiments, the lock nut 2100 is configured to receive the distal threaded portion 1012, a portion of the elongated main body 1020, as well as the plunger 110. For example, in some embodiments, the diameter of the lock nut 2100 is between about 5 mm and about 30 mm. In some embodiments, the diameter of the lock nut 2100 is between about 10 mm and about 20 mm. In some embodiments, the diameter of the lock nut 2100 is between about 12 mm and about 16 mm. When locking system 2000 is assembled, the distal portion of central bore 1802 of the medial housing 1800 is configured to receive the lock nut 2100 with the most proximal side of lock nut 2100 abutting the distal side of flange wall 1804. As can be seen in FIG. 38, the lock nut 2100 is configured to receive the distal threaded portion 1012 of the hub 1010. Accordingly, in some embodiments, the hollow inner side of the lock nut 2100 is threaded such that it may be threadably connected to the distal threaded portion 1012 of the hub 1010. Rotational threading of the lock nut 2100 onto the distal threaded portion 1012 of the hub 1010 may be accomplished by one or more notches disposed on the distal side of the lock nut 2100. For exemplary purposes, four notches 2102, 2104, 2106, 2108 are illustrated on lock nut 2100. However, in some embodiments lock nut 2100 may comprise one, two, three, four, five, six, or more notches. As will be discussed in greater detail below with reference to FIGS. 39-41, notches 2102, 2104, 2106, 2108 allow for rotating lock nut 2100 using a lock nut tool 2200.

As can be seen in FIG. 38 and as discussed above, in some embodiments, the proximal end of the elongated main body 1020 is received within the distal portion of bore 1016 of the hub 1010. The hub 1010 includes an inner protrusion 1017 that protrudes circumferentially inwards and prevents extension of the elongated main body 1020 proximally through the bore 1016. In some embodiments, as illustrated in FIG. 38, the bore 1016 is configured to allow the passage of the plunger 110 therethrough.

When assembling the locking system 2000, the plunger 110 may be inserted through the central bore 1802 of the medial housing 1800 and the bore 1016 of the hub 1010. The hub 1010 may subsequently be inserted into the proximal side of the central bore 1802 of the medial housing 1800. As mentioned above, the flange head 1014 may abut the flange wall 1804 located within the central bore 1802. The elongated main body 1020 may then be placed around the distal end of the plunger 110 along with the lock nut 2100, as illustrated in FIG. 37. The proximal end of the elongated main body 1020 may then be inserted into and received by the distal portions of the bore 1016 of the hub 1010. In some embodiments, the indent 1024 on the proximal end of the elongated main body 1020 may be lined up with the elongated main body lock 1019 located within the bore 1016 for proper reception of the elongated main body 1020 therein. In some embodiments, following insertion of the elongated main body 1020 into the bore 1016, the lock nut 2100 may threadably receive the distal threaded portion 1012 of the hub 1010. For example, in some embodiments, a user may use lock nut tool 2200 to threadably connect lock nut 2100 to the distal threaded portion 1012 of the hub 1010.

Figure 40:
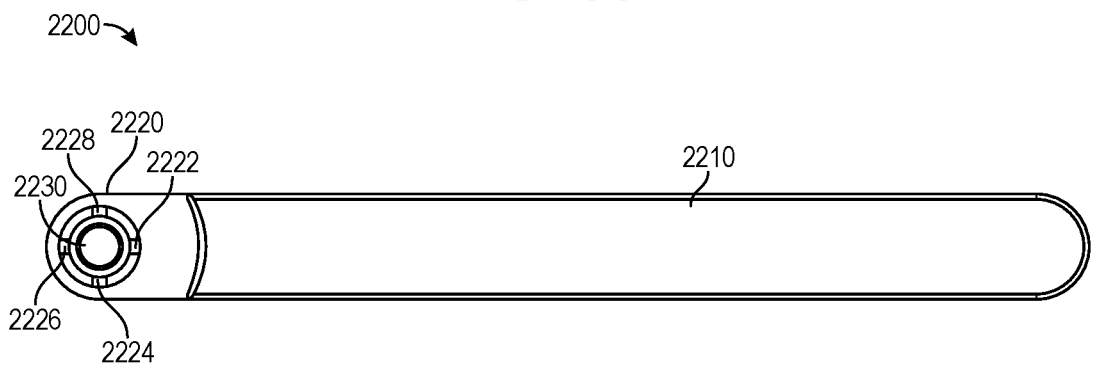
FIG. 40 is a front view of some embodiments of a lock nut tool.
Figure 41:
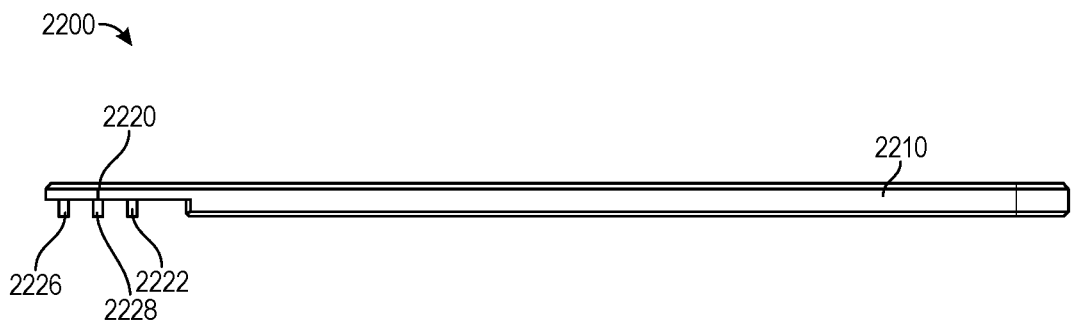
FIG. 41 is a side view of some embodiments of the lock nut tool of FIG. 40.

With reference to FIGS. 40 and 41, in some embodiments, the lock nut tool 2200 comprises a head portion 2220 and an arm portion 2210. The head portion 2220 may be configured to operatively engage the lock nut 2100 while the arm portion 2210 may be configured to rotationally drive the lock nut 2100 in a clockwise or counterclockwise direction. In some embodiments, the head portion 2220 comprises one or more protrusions configured to be inserted into the one or more notches 2102, 2104, 2106, 2108 on lock nut 2100. As an example, illustrated in FIGS. 40-41 lock nut tool 2200 comprises four protrusions 2222, 2224, 2226, and 2228. While four protrusions 2222, 2224, 2226, 2228 are illustrated here, it is contemplated that head portion 2220 may comprise any number of protrusions for operatively engaging the lock nut 2100. In some embodiments, the lock nut tool 2200 may comprise the same number of protrusions as notches in the lock nut 2100. In some embodiments, the lock nut tool 2200 may comprise a different number of protrusions as notches in the lock nut 2100.

Figure 39:
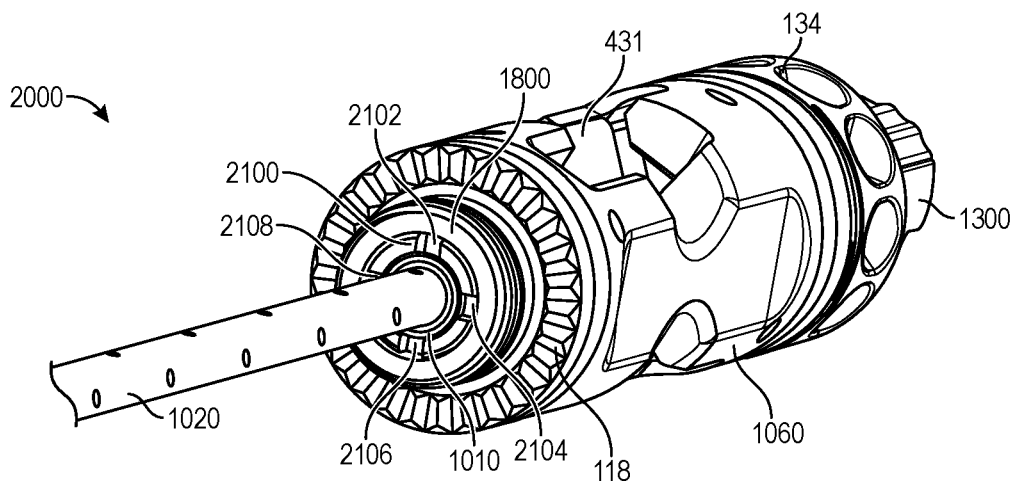
FIG. 39 is a distal perspective view of the locking system of the insertion instrument of FIG. 24, in some embodiments.

In some embodiments, the head portion 2220 may include a hole 2230. The hole 2230, in some embodiments, may be configured to receive one or both of the plunger 110 and the elongated main body 1020. Accordingly, in these embodiments, the lock nut tool 2200 may be slid proximally towards the lock nut 2100 while receiving the elongated main body 1020 and the plunger 110 through the hole 2230. In some embodiments, this motion allows the protrusions 2222, 2224, 2226, 2228 to reach the notches 2102, 2104, 2106, 2108 located on the lock nut 2100. In some embodiments, the notches 2102, 2104, 2106, 2108 receive the protrusions 2222, 2224, 2226, 2228, thereby operatively engaging the lock nut tool 2200 with the lock nut 2100. A user may subsequently, via rotation of the arm portion 2210, thread the lock nut 2100 onto and around the distal threaded portion 1012 of the hub 1010. As the hub 1010 is prevented from moving distally due to the flange head 1014 abutting the flange wall 1804, threading of the lock nut 2100 may pull the lock nut 2100 proximally into the central bore 1802 until seated against the distal side of the flange wall 1804. This is best depicted in FIGS. 38-39, which illustrate the lock nut 2100 flush with the distal end of the medial housing 1800, securing the hub 1010 and the elongated main body 1020 therein.

In some embodiments, opposite operations may cause unfastening of the lock nut 2100 from the distal threaded portion 1012 of the hub 1010. For example, a user may use the lock nut tool 2200 to similarly engage the lock nut 2100 by inserting the protrusions 2222, 2224, 2226, 2228 into the notches 2102, 2104, 2106, 2108 and rotating the arm portion 2210 of the lock nut tool 2200. This rotation may be counterclockwise or clockwise depending on the threading direction of the distal threaded portion 1012 and the internal threading of the lock nut 2100. Eventual separation of the lock nut 2100 from the hub 1010 may allow a user to subsequently separate some components of the insertion instrument 1000. For example, a user may remove a used elongated main body 1020 and replace it with a new elongated main body 1020. Other components, such as the lock nut 2100, the hub 1010, the medial housing 1800, or others, may also be removed and replaced or serviced.

Assembly of the Insertion Instrument

Referring now to FIGS. 3 and 25-39, the insertion instrument 1000 is designed for ease of assembly. As best shown in FIGS. 29-30, the exchangeable plunger knob 1300 is coupled to the locking cap 114 of the plunger 110. The exchangeable plunger knob 1300 includes a threaded core 126 that is rotated into a recess 122 of the locking cap 114. Next, the plunger 110 and plunger tab 431, 331, 131 are inserted through the proximal ring 1950 and proximal housing 1900 and into the handle 1060. The proximal housing 1900, proximal ring 1950, and handle 1060 include an opening 132 (similar to shown in FIG. 5) for slidably engaging the plunger tab 431, 331, 131 therein. As the plunger 110 and plunger tab 431 are slid within the handle 1060, the end cap 134 of exchangeable plunger knob 1300 abuts the proximal ring 1950. The exchangeable plunger knob 1300 and/or end cap 134 are rotated to threadably engage the proximal threaded feature 1170 of the proximal housing 1900 and secure the plunger 110 and exchangeable plunger knob 1300 to the handle 1060.

The plunger 110 can next be inserted through the hub 1010, the medial housing 1800, and into the elongated main body 1020 with the lock nut 2100 located around the elongated main body 1020 (see FIG. 37). The system is then locked as described above. For example, a lock nut tool 2200 may be slid over the elongated main body 1020 and operatively engage the lock nut 2100. The lock nut 2100 may then be threadably rotated around the distal threaded portion 1012 of the hub 1010, with a proximal portion of the elongated main body 1020 being disposed within the bore 1016 of the hub 1010 (see FIGS. 37-38). Once fully threaded therein, the insertion instrument 1000 is in a locked position.

The distal portion 108 of the elongated main body 1020 is inserted through the proximal drive shaft 1600 and spring 1630 and into the axial passage 1440 of the distal hex nut driver 1400 (see FIG. 25), with the spring 1630 abutting a portion of the distal hex nut driver 1400 and the distal end of the proximal drive shaft 1600. The knob 148 of the proximal drive shaft 1600 and/or end cap 150 are rotated to couple the distal threaded feature 1190 of the medial housing 1800 with the end cap 150.

At this point, with the plunger 110 and exchangeable plunger knob 1300 secured to the handle 1060, the plunger tab 431, 331, 131 is in the proximal position within the staggered path 121 (as shown in FIG. 9). The insertion instrument 1000 is now in the "unlocked" position. "Unlocked" refers to the implant 200 not being secured to the insertion instrument 1000 even if the implant 200 is mounted on the tip 1130. The implant 200 is locked to the insertion instrument 1000 by deploying the plunger 110 as described below.

Locking the Implant to the Insertion Instrument

To lock the implant 200 to the insertion instrument 1000 the plunger 110 should be fully retracted into the unlocked position. This can be easily viewed by the plunger tab 431, 331, 131 being in the proximal most location within the staggered path 121 of the handle 1060.

During use, three components of the insertion instrument are used to translate the plunger 110 and deploy the implant 200: the exchangeable plunger knob 1300, the plunger tab 431, 331, 131 and the knob 148 of the proximal drive shaft 1600. Each of these components may include a coating with PVD. The black PVD coating provides anti-galling coating as well as a usability indicator to the user as to which instrument components are manipulated during the surgical technique.

To lock the implant, the distal portion 108 of the elongated main body 1020 is uncovered by sliding the distal hex nut driver 1400 distally around the proximal drive shaft 1600. The distal hex nut driver 1400 is initially prevented from rotation because the pins 1650 are riding in the complementary slots 1610 (best seen in FIG. 26). However, once the pins 1650 bottom out in the complementary slots 1610, the user can hold the knob 148 and rotate the distal hex nut driver 1400 so the pins 1650 come to rest in the radial portion 1640 of the complementary slots 1610. As a result, the distal hex nut driver 1400 is retained and will stay retracted even when released by the user.

A matching adapter 170 can be slid over the distal portion 108 of the elongated main body 1020 so that the legs 175, 176 can be inserted into the opening 1580. Locking tabs 177 may provide an audible click when the legs 176 deflect outward into the transverse locking passage 157 to confirm positive engagement for the user.

After positioning the adapter 170 on the hex nut driver 1400, the implant 200 can be partially engaged to the tip 1130 by a snap friction fit. The tip 1130 is slightly compressed, by virtue of the flexible arms 109, and passed into the proximal internal recess 250 of the implant 200 with the blades 220a, 220b of the implant 200 aligned with the flexible arms 109. The tip 1130 stops within the recess 250 when the flexible arms 109 fit within the transverse groove 253. At this point, the implant 200 is coupled to the insertion instrument 1000 but not yet "locked."

To lock the implant 200 to the insertion instrument 1000, the plunger 110 is moved from the unlocked position to the locked position. To move the plunger 110 distally, the exchangeable plunger knob 1300 is rotated clockwise (looking from the proximal end) until the plunger tab 431, 331, 131 rests adjacent the transition wall 127, as shown in FIGS. 9 and 10. The distal pushing end 112 of the plunger 110 is approximately flush with the tip 1130 of the elongated main body 1020. Thus, the flexible arms 109 of the elongated main body 102 can no longer flex out of the transverse groove 253. Consequently, the implant 200 is tightly coupled and locked to the tip 1130 so that inadvertent removal does not occur. The insertion instrument 1000 is now ready to have the socket end 1560 of the distal hex nut driver 1400 engaged to the hex nut 235 of the implant 200.

To engage the distal hex nut driver 1400 to the hex nut 235 of the implant 200, the knob 148 is held to prevent rotation while the distal hex nut driver 1400 is rotated to bring the pins 1650 out of the radial portion 1640 of the complementary slots 1610. The spring 1630 will bias the distal hex nut driver 1400 outward so care should be taken to slowly extend the distal hex nut driver 1400 to have the hex socket 172 properly engage the hex nut 235 of the implant 200 (best seen in FIG. 22). In order to have the hex socket 172 properly engage the hex nut 235, a slight manual rotation or jiggle of the distal hex nut driver 1400 may be required. The implant 200 is now locked to the insertion instrument 1000 and ready for implantation. The force provided by the spring 1630 is optimized to ensure proper, reliable engagement between the adapter 170 and hex nut 235 while not providing excessive force to interfere with the operation of the insertion instrument 1000 or deployment of the implant 200.

Deployment of the Implant in the Interspinous Space

FIGS. 20-23 illustrate various stages during insertion and placement of the implant 200 into a target interspinous process space 382. Steps of deployment of the implant are similar between insertion instrument 100 and insertion instrument 1000, and therefore the below description is in reference to both insertion instruments 100, 1000. Additional details are set forth in U.S. patent application Ser. No. 12/011,905, filed Jan. 30, 2008 (U.S. Patent Pub. No. 2009/0054988), which is incorporated herein by reference in its entirety.

FIG. 20 is a dorsal (rear) view of the implant 200, still held by the insertion instrument 1000, within a lumen of an introducer tube 387, during lateral insertion thereof. For direct lateral insertion of the implant 200 into the target interspinous process space 382, an incision is formed in the skin 388 of a patient, and ultimately an introducer tube 387 is advanced through the tissue to the target interspinous process space 382, through which the implant 200 is advanced, connected to the insertion instrument 1000.

The implant 200 is axially rotated by way of the insertion instrument 1000, thus threading the implant 200 into the target interspinous process space 382, distracting the adjacent spinous processes 381a, 381b, and advancing the implant 200, generally centered with respect to the spinous processes 381a, 381b.

To rotate the implant 200, the handle 1060 of the elongated main body 1020 is rotated in a tightening or clockwise direction to self-thread the implant 200 through the interspinous space 382, as shown in FIG. 21. During the rotation of the implant 200, the implant 200 distracts the interspinous space. Relative rotation and axial translation between the implant 200 and the insertion instrument 1000 is inhibited because the implant 200 is locked onto the tip 1130 by the distal pushing end 112 of the plunger 110. Distraction can also be performed in advance by a separate instrument, with insertion of the implant 200 following, and maintaining such distraction.

When anchoring blades 220a, 220b have passed through the interspinous space 382 as shown in FIG. 22, the anchoring blades 220a, 220b can be deployed.

To deploy the implant 200, the plunger tab 431, 331, 131 is rotated by the user from the first path 123 to the second path 125 along the transition wall 127 (best shown in FIGS. 9-12). After the plunger tab 431, 331, 131 is fully positioned within the second path 125, the exchangeable plunger knob 1300 is again rotated clockwise to continue distal movement of the plunger tab 431, 331, 131.

As the plunger 110 continues to move distally, the distal pushing end 112 enters in the recess 221 of the implant plunger 226. As the plunger 110 continues to move distally, the distal pushing end 112 applies pressure and moves the implant plunger 226 distally to deploy the blades 220a, 220b. Once the plunger tab 431, 331, 131 is positioned in the distal most position of the staggered path 121 (as shown in FIG. 12), the implant is "deployed". The physician can also verify proper deployment of the blades 220a, 220b by fluoroscopy. Once the blades 220a, 220b are deployed, the implant 200 can be set in final position.

Referring now to FIG. 23, the hex nut 235 of the implant 200 is shown being driven by the distal hex nut driver 1400 to engage the spikes 224, 234 to the spinous processes 381a, 381b. The distal hex nut driver 1400 rotates the hex nut 235 to move the spike cap 230 distally. Because the spike cap 230 is keyed to the implant 200 to prevent rotation, as the hex nut 235 turns, the spike cap 230 slides distally.

To rotationally drive the hex nut 235, the knob 148 is rotated clockwise relative to the elongated main body 1020. In some embodiments, the handle 1060 is held in place while rotating the knob 148 to maintain the position of the elongated main body 1020. Turning the knob 148 turns the adapter 170 and thereby the hex nut 235. Once the spike cap 230 engages the spinous processes 381a, 381b, the blades 220a, 220b are drawn proximally into engagement with the bone 381a, 381b. A flat portion of the implant 200 is not threaded so that the implant 200 slides proximally, and allows the spike cap 230 to translate linearly along the body 212 without rotation. While the distal hex nut driver 1400 is used to tighten the hex nut 235, the surgeon can feel the spike cap 230 become fully seated and/or full seating is seen in an accompanying fluoroscopy display.

Once the implant 200 is properly deployed, the insertion instrument 1000 is disengaged from the implant 200. To disengage the insertion instrument 1000, plunger 110 is withdrawn from the implant 200. To withdraw the plunger 110, the exchangeable plunger knob 1300 is loosened or rotated in the counter-clockwise direction relative to the handle 1060 of the elongated main body 1020 to move the plunger tab 431, 331, 131 proximally. As the plunger tab 431, 331, 131 slides proximally within the staggered path 121, the distal pushing end 112 is translated proximally.

Once the plunger tab 431, 331, 131 abuts the transition wall 127 the plunger tab 431, 331, 131 is rotated from the second path 125 to the first path 123. The exchangeable plunger knob 1300 is loosened or rotated in the counter-clockwise direction relative to the handle 1060 of the elongated main body 1020 to continue to slide the plunger tab 431, 331, 131 proximally. The plunger 110 is withdrawn from the tip 1130 and the flexible arms 109 are again allowed to flex so that the tip 1130 pops out of the proximal internal recess 250 of the implant 200. With the plunger 110 retracted to the unlocked position, the coupling force of the tip 1130 to the implant 200 can be overcome to fully detach the insertion instrument 1000. In some embodiments, spring 1630 may bias the distal hex nut driver 1400 away from implant 200, thereby aiding in detachment of the implant 200. Once removed, the insertion instrument 1000 can be removed from the patient for disassembly, cleaning, and re-use.

Disassembly of the Insertion Instrument

It is advantageous to disassemble the insertion instrument 1000 for cleaning or replacing parts. Referring to FIGS. 3-10 and 25-30, the plunger 110 can be removed from the elongated main body 1020. The exchangeable plunger knob 1300 can be unscrewed from the plunger 110. The distal hex nut driver 1400 and the proximal drive shaft 1600 can be removed from around the elongated main body 1020. The elongated main body 1020 can be removed from the handle 1060 by unlocking the locking system 2000 as described above. The adapter 170 can be unsnapped from the distal hex nut driver 1400. At this point, the components of the insertion instrument 1000 are ready to be cleaned and/or replaced.

Additionally, in some embodiments as described above it may be advantageous to replace a first exchangeable plunger knob 1300 with a second exchangeable plunger knob 1300 so as to change the diameter of the knob. In some embodiments, a user may maintain portions or all of insertion instrument 1000 together and replace the exchangeable plunger knob 1300. For example, in some embodiments a user may rotatably uncouple the end cap 134 from the proximal threaded feature 1170. In some embodiments, a user may rotatably uncouple the threaded core 126 of the first exchangeable plunger knob 1300 from the locking cap 114. Once removed, in some embodiments the threaded core 126 of a second exchangeable plunger knob 1300 may be threadably coupled to the locking cap 114. In some embodiments, the end cap 134 may be threadably recoupled to the proximal threaded feature 1170 of the proximal housing 1900. Accordingly, in some embodiments it may be easy for a user to exchange the exchangeable plunger knob 1300 for purposes as described above.

As described in detail above, the locking system 2000 allows for relatively easy replacement of one or more components of the insertion instrument 1000. Due to the relatively frequent forces exerted on certain components of insertion instrument 1000, parts may become damaged and need to be replaced or in need of servicing. Accordingly, the locking system 2000 allows a user to easily remove and replace the damaged components without having to alter or dispose of any components that are not damaged. For example, the tip 1130 of the elongated main body 1020 may become damaged following the insertion of an implant 200 due to the strong forces exerted on the flexible arms 109 during an operation. Accordingly, a user may replace the elongated main body 1020 by simply unlocking the locking system 2000 and securing a new elongated main body 1020 by locking the locking system 2000 back into place. As mentioned above, other components subjected to similar forces may also need replacement or repair and may similarly be replaced with relative ease.

Furthermore, the locking system 2000 provides certain aspects that form a stable connection between certain components of the insertion instrument 1000 that improves the durability and life of the insertion instrument 1000. For example, the handle pins 1814, 1816, 1818 are configured to increase the stability and transfer of rotational force between the handle 1060 and medial housing 1800. In another example, the combination of the planar side 1018 and internal planar wall 1806 improve the transfer of applied forces from the medial housing 1800, and thus the handle 1060, to the hub 1010 and thus the elongated main body 1020 and the implant 200. In yet another example, the indent 1024 in the proximal end of the elongated main body 1020 receiving the elongated main body lock 1019 further helps transfer rotational force from the hub 1010 to the elongated main body 1020. As hub 1010 is rotated via the medial housing 1800, the elongated main body lock 1019 will press against the extension 1022 disposed on the proximal end of the elongated main body 1020. Such rotation will directly press against the extension 1022 and cause rotation of the elongated main body 1020. These examples, alone or in combination, greatly improve the durability of the insertion instrument 1000 as rotational forces are required to drive the implant 200 into the tissue.

Additional Embodiment

Figure 42:
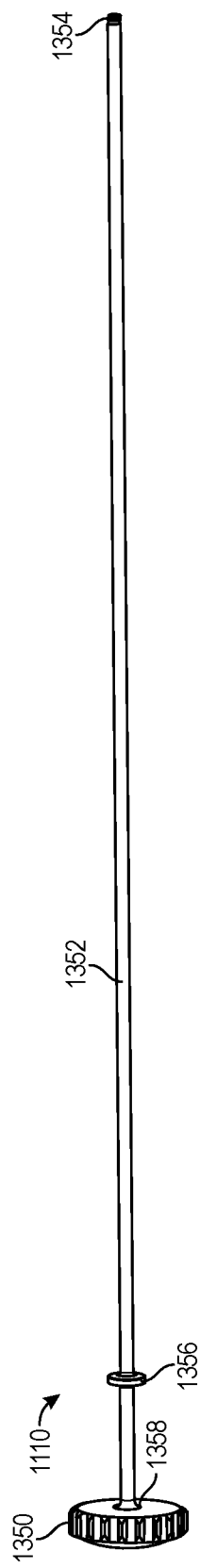
FIG. 42 is a side view of an embodiment of a wing actuation tool.

Illustrated in FIGS. 42-56 is an additional embodiment of an insertion instrument 3000. With reference to FIG. 42, a wing actuation tool 1110 is depicted. In some embodiments, and as will be described in greater detail below, wing actuation tool 1110 may be disposed within insertion instrument 3000 and configured to actuate certain components of an implant, such as implant 3200 or 3400. In some embodiments, wing actuation tool 1110 includes a plunger knob 1350 mechanically coupled to a plunger shaft 1352. In some embodiments, the plunger shaft 1352 includes a coupling tip 1354 on the distal end. In some embodiments, plunger shaft 1352 includes a concentric flange 1356 disposed distal to the plunger knob 1350.

In some embodiments, plunger shaft 1352 is mechanically coupled to the plunger knob 1350 at the proximal end via an extension 1358. In some embodiments, the extension 1358 may include external thread that is received by and threaded into a bore located within the plunger knob 1350. In some embodiments, the extension 1358 may be welded to the plunger knob 1350. Welding of the extension 1358 may occur with or without threading the extension 1358 to the plunger knob 1350. Other mechanical coupling systems known to one skilled in the art may be used to mechanically couple the plunger shaft 1352 to the plunger knob 1350. Alternatively, plunger shaft 1352 and plunger knob 1350 may be manufactured as a unitary part.

In some embodiments, one or more components of the wing actuation tool 1110 may be coated in a biocompatible, corrosion resistant material to help protect and/or strengthen the component. For example, some or all portions of wing actuation tool 1110 may be advantageously reinforced with a coating material to increase the durability of the components while maintaining safety to the patient. In some embodiments, the coating material may be a biocompatible substance. Such a coating material may be applied specifically to components of wing actuation tool 1110 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 2000™. In some embodiments, the coating material may be applied to the entirety of the wing actuation tool 1110. In some embodiments, the coating material may be applied to particular portions of the wing actuation tool 1110 that experience greater forces, such as the plunger shaft 1352 and the coupling tip 1354. In some embodiments, the thickness of the coating material may be between about 1 μm to about 15 μm. In some embodiments, the coating material may be between about 2 μm to about 10 μm.

Figure 43:
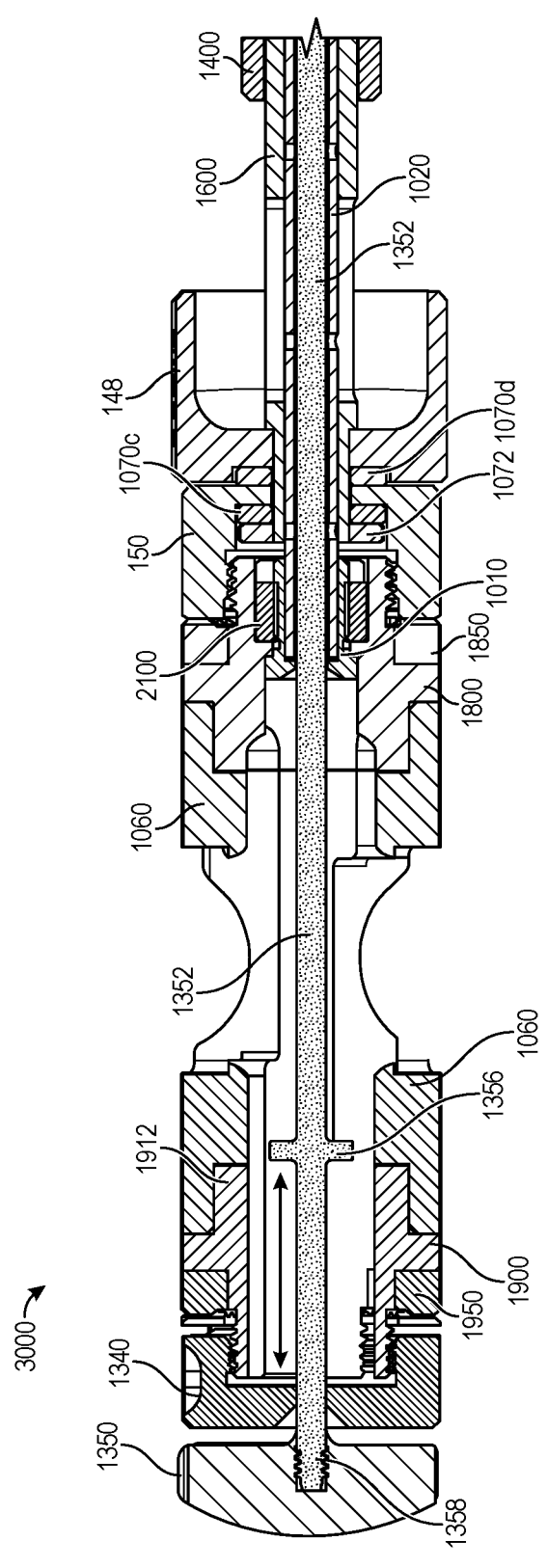
FIG. 43 is a cross sectional view of an embodiment of an insertion instrument including the wing actuation tool of FIG. 42.

FIG. 43 illustrates a cross-sectional view of some components of insertion instrument 3000. In some embodiments, similar to plunger 110, a distal portion of plunger shaft 1352 is received by the elongated main body 1020. In some embodiments, the distal portion of plunger shaft 1352 is configured to extend through the elongated main body 1020 such that the coupling tip 1354 may extend distally therefrom upon distal movement of the wing actuation tool 1110 (see FIG. 46).

As illustrated, in some embodiments plunger shaft 1352 extends through a proximal end cap 1340. In some embodiments, the plunger knob 1350 is maintained on the proximal end of the proximal end cap 1340. In some embodiments, the concentric flange 1356 is maintained on the distal end of the proximal end cap 1340. Accordingly, in some embodiments, longitudinal movement of the plunger shaft 1352 is bounded by the plunger knob 1350 in the distal direction and the concentric flange 1356 in the proximal direction. As such, the plunger shaft 1352 may only move longitudinally roughly the distance between the plunger knob 1350 and the concentric flange 1356.

Figure 44:
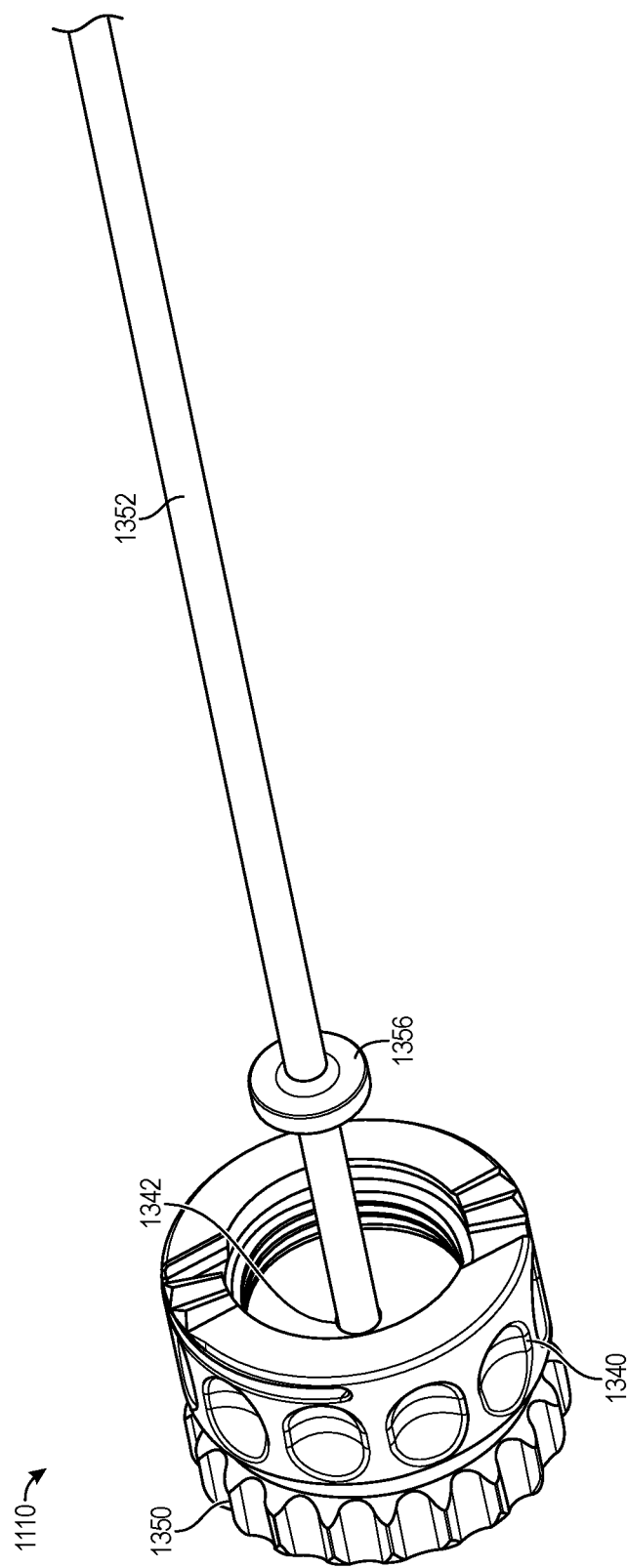
FIG. 44 is a distal perspective view of the wing actuation tool of FIG. 42.
Figure 45:
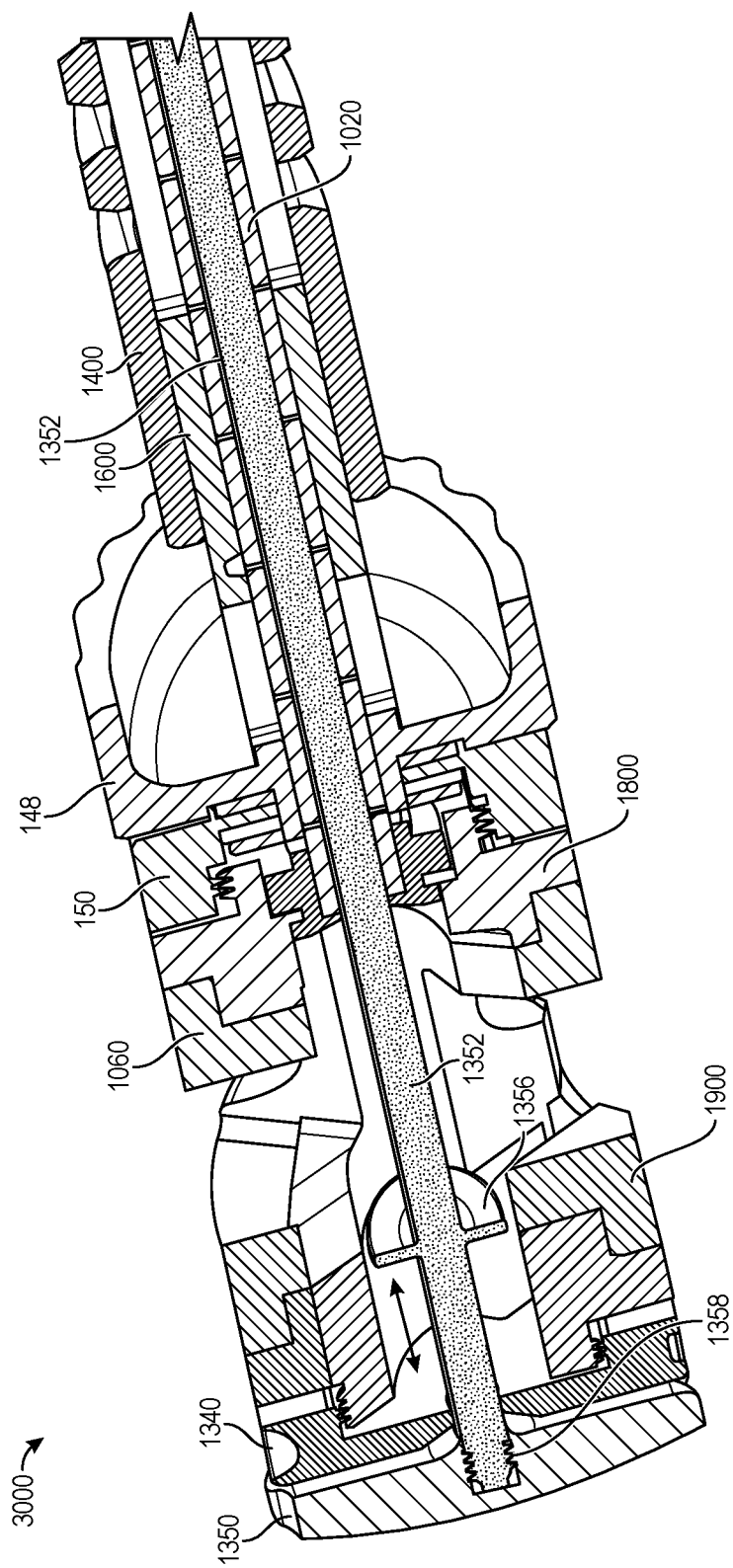
FIG. 45 is a distal perspective view of a cross section of the insertion instrument of FIG. 43.

FIGS. 44-45 illustrate a distal perspective view of the wing actuation tool 1110 and are best viewed together for the following description. As can be seen, the proximal end cap 1340 includes a hole 1342 configured to receive a portion of the plunger shaft 1352. The hole 1342 may be configured to allow longitudinal movement of the plunger shaft 1352 therethrough. In some embodiments, hole 1342 may have a smaller diameter than that of the concentric flange 1356. Accordingly, the concentric flange 1356 may abut the distal side of the proximal end cap 1340 when wing actuation tool 1110 is retracted proximally. In some embodiments, the concentric flange 1356 may be configured to be received within handle 1060 and be translatable therewithin.

As mentioned above, in some embodiments, a distal portion of the plunger shaft 1352 may be received by the elongated main body 1020. Similar to plunger 110, plunger shaft 1352 may be longitudinally translatable and rotatable within the elongated main body 1020.

In comparison to some embodiments, plunger shaft 1352 may lack a plunger tab 131/331/431 as described above. As previously described, the plunger tab 131/331/431 is configured to indicate and regulate the phases of deployment of implant 200. In some embodiments, the concentric flange 1356 keeps the plunger shaft 1352 secured to the insertion instrument 3000.

Importantly, in some embodiments, wing actuation tool 1110 and proximal end cap 1340 may be configured to easily exchange with certain components of insertion instrument 100/1000. As will be described in greater detail below, in some embodiments wing actuation tool 1110 and proximal end cap 1340 may be configured to replace one or more of plunger 110, plunger tab 131/331/431, plunger knob 130, exchangeable plunger knob 1300, threaded core 126, end cap 134, etc. For example, a user may threadably remove end cap 134 from proximal housing 1900. When disconnected, the plunger knob 130/1300, threaded core 126, plunger tab 131/331/431, and plunger 110 may be removed from the insertion instrument 100/1000. Following removal, a user may then insert plunger shaft 1352 of wing actuation tool 1110 through the proximal housing 1900, handle 1060, medial housing 1800, and the elongated main body 1020. As shown in FIG. 43, the proximal end cap 1340 may then be threadably coupled to the proximal housing 1900, thereby securing the wing actuation tool 1110 to the insertion instrument 100/1000/3000.

Figure 46:
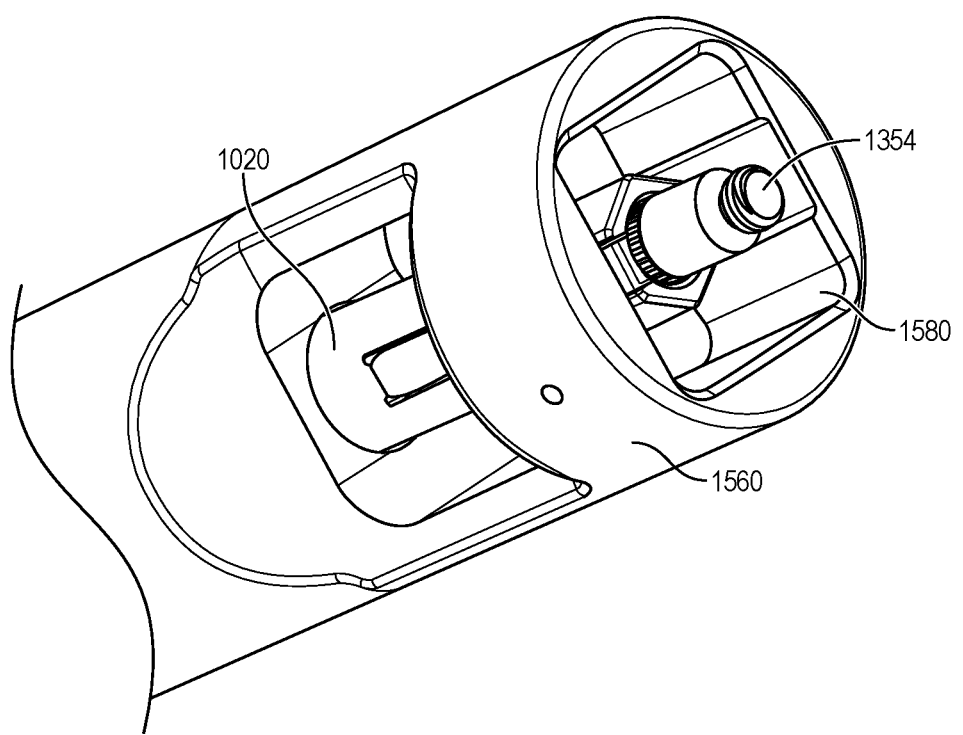
FIG. 46 is a distal perspective view of a coupling tip of the wing actuation tool of FIG. 42.

FIG. 46 illustrates a distal perspective view of distal components of insertion instrument 3000. As described above, in some embodiments the coupling tip 1354 of the plunger shaft 1352 may be configured to extend distally from the elongated main body 1020 (e.g., when coupling to implant 3200/3400). In some embodiments, coupling tip 1354 may be received by a portion of implant 3200/3400. In some embodiments, coupling tip 1354 may be threadably received by a portion of implant 3200/3400. In some embodiments, coupling tip 1354 may temporarily attach to implant 3200/3400 by any means commonly known to one skilled in the art. Temporary attachment of the coupling tip 1354 to the implant 3200/3400 may prevent disconnection of the implant 3200/3400 from the wing actuation tool 1110 during implantation. Further, in some embodiments, temporary attachment of the coupling tip 1354 to the implant 3200/3400 may allow for the wings 3230, 3232 or 3430, 3432 to be retracted by proximal displacement of wing actuation tool 1110. This will be discussed in greater detail below with reference to FIGS. 49-52.

Figure 47:
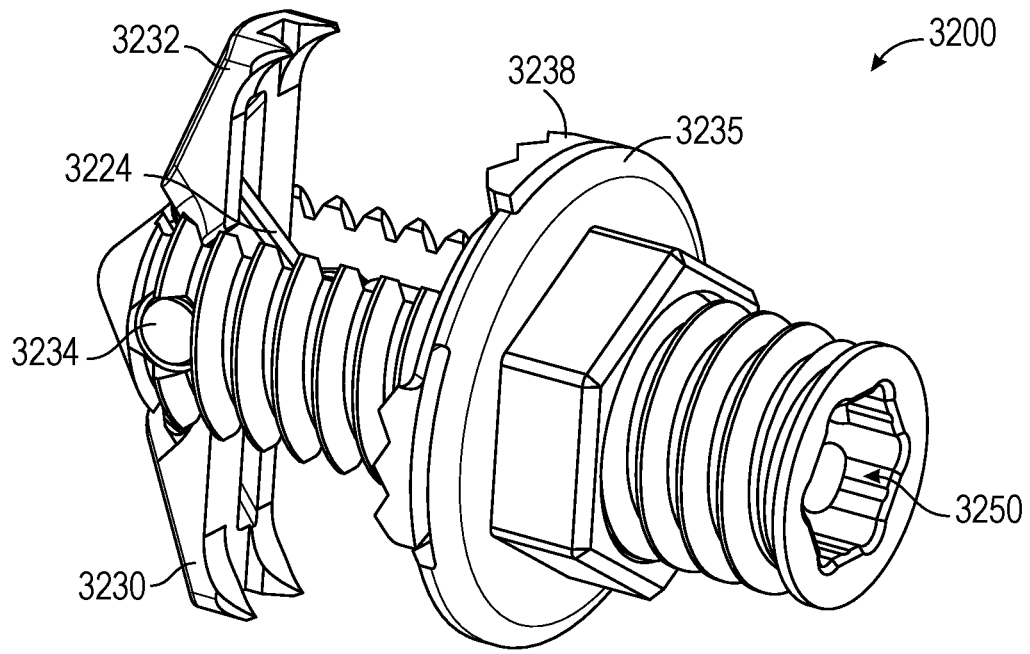
FIG. 47 is a distal perspective view of a second embodiment of an implant in a deployed configuration, in some embodiments.
Figure 48:
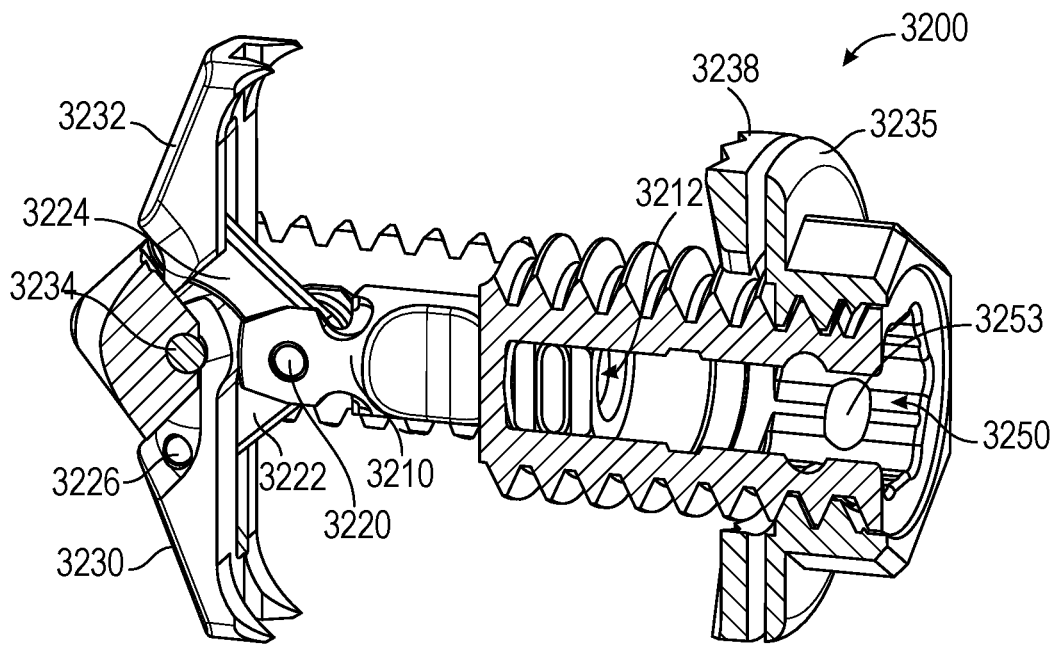
FIG. 48 is a distal perspective view of a cross section of the implant of FIG. 47 in a deployed configuration.

FIGS. 47 and 48 illustrate an embodiment of implant 3200 in the deployed state, which can be used together with insertion instrument 3000, and are best viewed together for the following description. Implant 3200 may include a plurality of wings (e.g., wings 3230, 3232) that are deployable (i.e., radially movable) from the implant 3200. The wings 3230, 3232 may pivot around a pivot pin 3234, which will be discussed in greater detail below. In some embodiments, wings 3230, 3232 may be operatively connected to an implant plunger 3210 via one or more linkages (e.g., linkages 3222, 3224). In some embodiments, linkages 3222, 3224 are connected to implant plunger 3210 via a linkage pin 3220. In some embodiments, linkages 3222, 3224 may be connected to the implant plunger 3210 via two or more linkage pins. Further, in some embodiments, each linkage 3222, 3224 is connected to a single wing 3230, 3232, respectively, at the distal end via pin 3226, 3228 (see FIG. 49). As will be discussed in greater detail below, longitudinal movement of implant plunger 3210 may cause wings 3230, 3232 to deploy and/or retract by way of linkages 3222, 3224.

Figure 49:
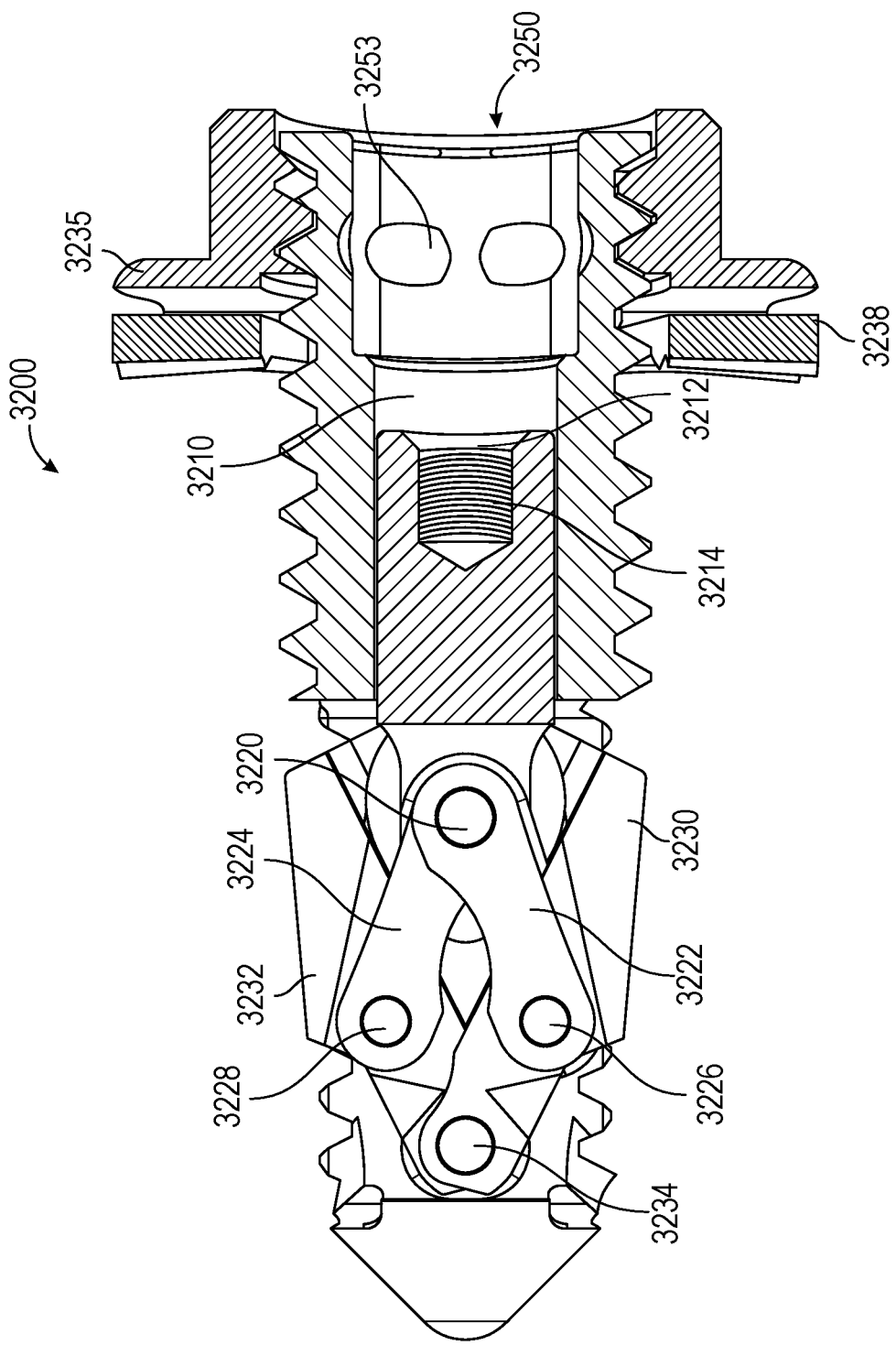
FIG. 49 is a cross sectional view of the implant of FIG. 47 in a retracted configuration.
Figure 50:
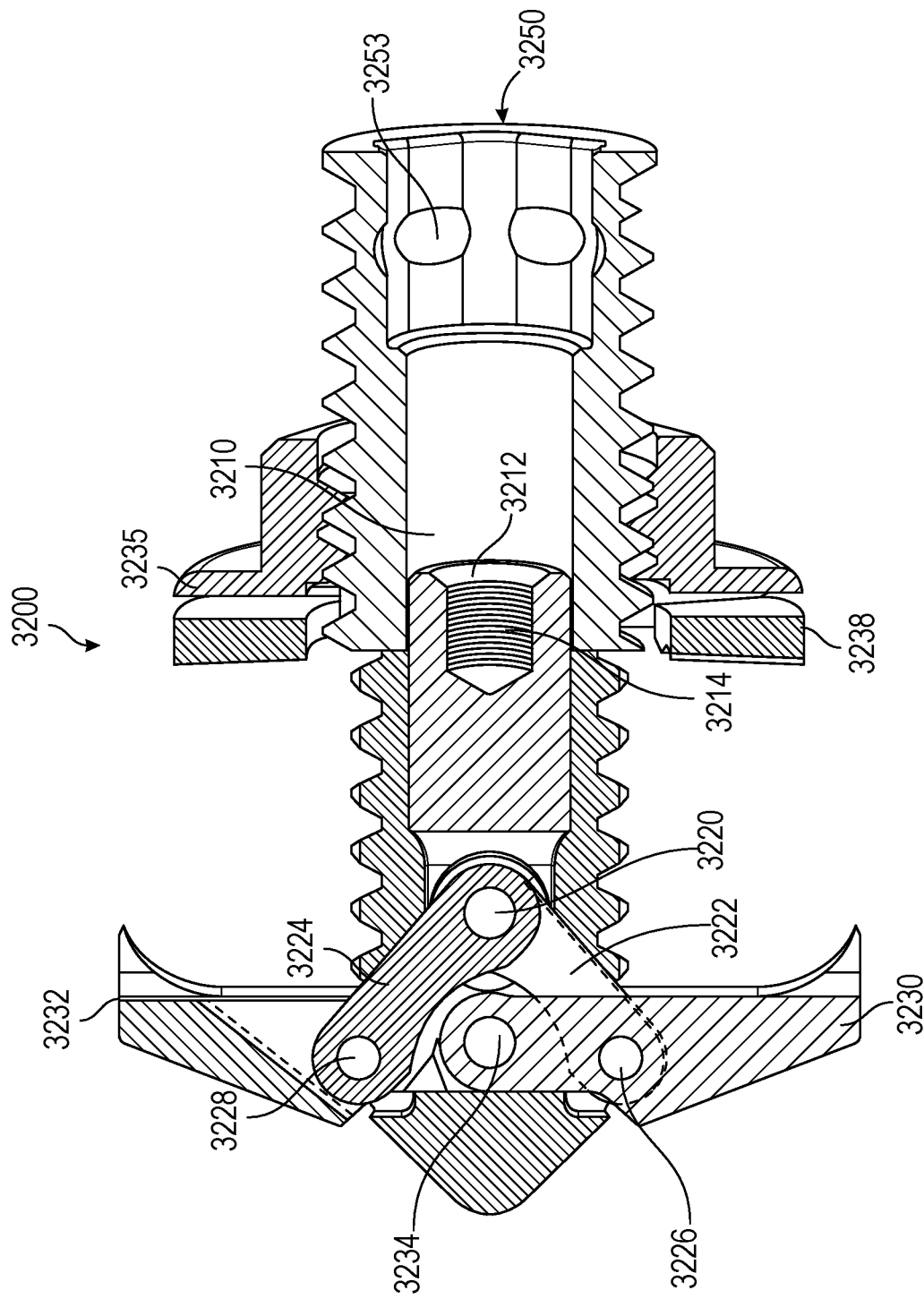
FIG. 50 is a cross sectional view of the implant of FIG. 47 in a deployed configuration.
Figure 51:
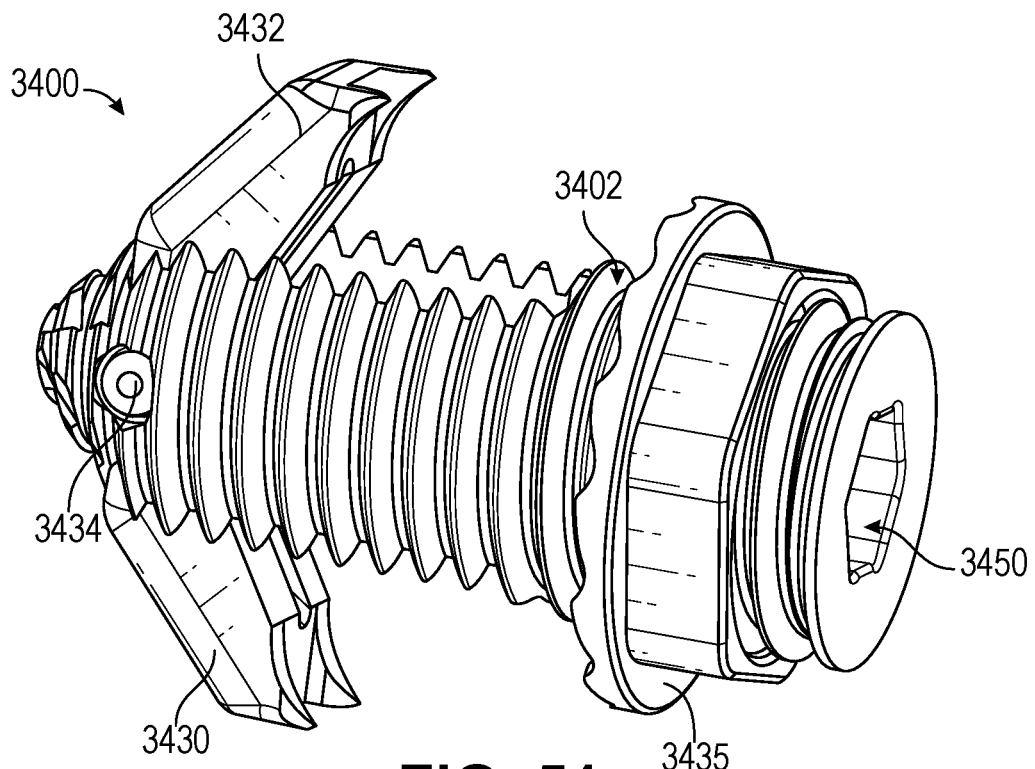
FIG. 51 is a distal perspective view of a third embodiment of an implant in a deployed configuration, in some embodiments.

In some embodiments, similar to implant 200, implant 3200 may include a hex nut 3235, which may also serve the functions of a spike cap. For example, hex nut 3235 may include a grip plate 3238 having flex arms on the distal side of the hex nut 3235 to allow for the hex nut 3235 to seat into the spinal process (e.g., spinal process 381*a*/381*b*) during surgery. In some embodiments, similar to implant 200 and 3400 (discussed below), implant 3200 may include a proximal internal recess 3250. In some embodiments, proximal internal recess 3250 includes detents 3253 configured to receive a portion of the elongated main body 1020 (e.g., ridges 111), as seen in FIGS. 51 and 54. In some embodiments and as illustrated in FIG. 48, implant plunger 3210 may include an implant plunger bore 3212. In some embodiments, implant plunger bore 3212 may be configured to receive a portion of the plunger shaft 1352 (e.g., coupling tip 1354). In some embodiments, implant plunger bore 3212 may be configured to temporarily attach to coupling tip 1354. For example, as illustrated in FIG. 49, in some embodiments, implant plunger bore 3212 may include a threaded bore 3214. In these embodiments, threaded bore 3214 may be configured to threadably receive coupling tip 1354. As such, implant plunger 3210 and wing actuation tool 1110 may be threadably coupled, such that movement of the wing actuation tool 1110 may deploy/retract wings 3230, 3232. FIG. 49 illustrates a cross section of implant 3200 in a retracted state, in some embodiments. FIG. 50 illustrates a cross section of implant 3200 in a deployed state, in some embodiments.

Figure 52:
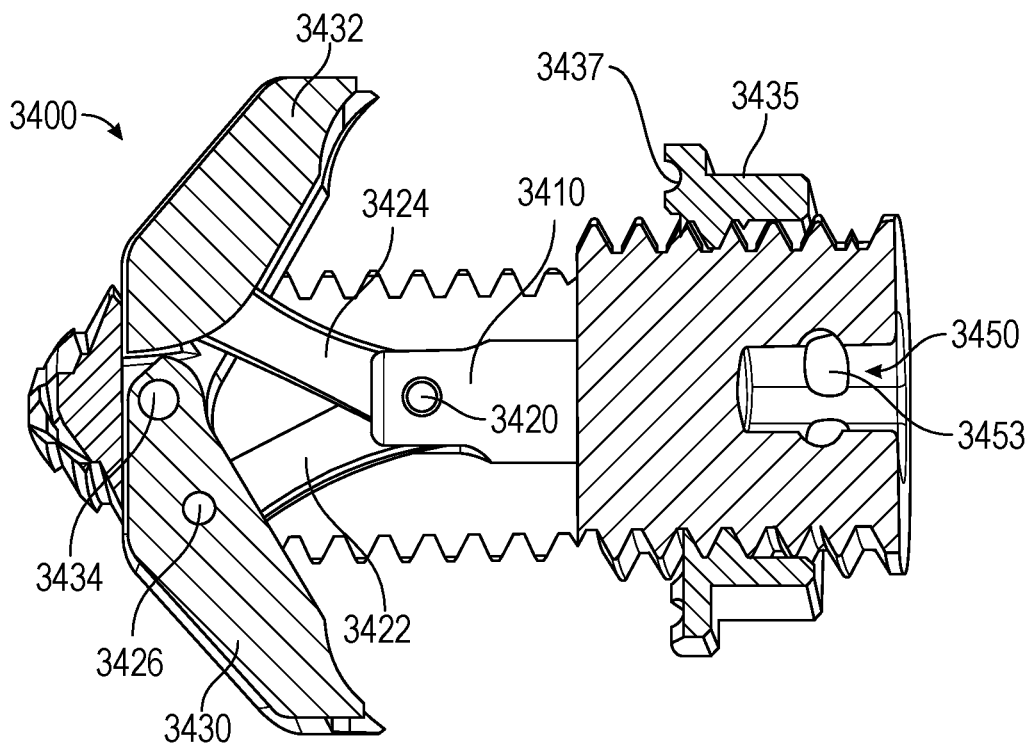
FIG. 52 is a distal perspective view of a cross section of the implant of FIG. 51 in a deployed configuration, in some embodiments.

FIGS. 51 and 52 illustrate an embodiment of implant 3400 in the deployed state, which can be used together with insertion instrument 3000 and are best viewed together for the following description. Implant 3400 may include a plurality of wings (e.g., wings 3430, 3432) that are deployable (i.e., radially movable) from the implant main body 3402. The wings 3430, 3432 may pivot around a pivot pin 3434, which will be discussed in greater detail below. In some embodiments, wings 3430, 3432 may be operatively connected to an implant plunger 3410 via one or more linkages (e.g., linkages 3422, 3424). In some embodiments, linkages 3422, 3424 are connected to implant plunger 3410 via a linkage pin 3420. In some embodiments, linkages 3422, 3424 may be connected to the implant plunger 3410 via two or more linkage pins. Further, in some embodiments, each linkage 3422, 3424 is connected to a single wing 3430, 3432, respectively, at the distal end via pin 3426, 3428. As will be discussed in greater detail below, longitudinal movement of implant plunger 3410 may cause wings 3430, 3432 to deploy and/or retract by way of linkages 3422, 3424.

Figure 56:
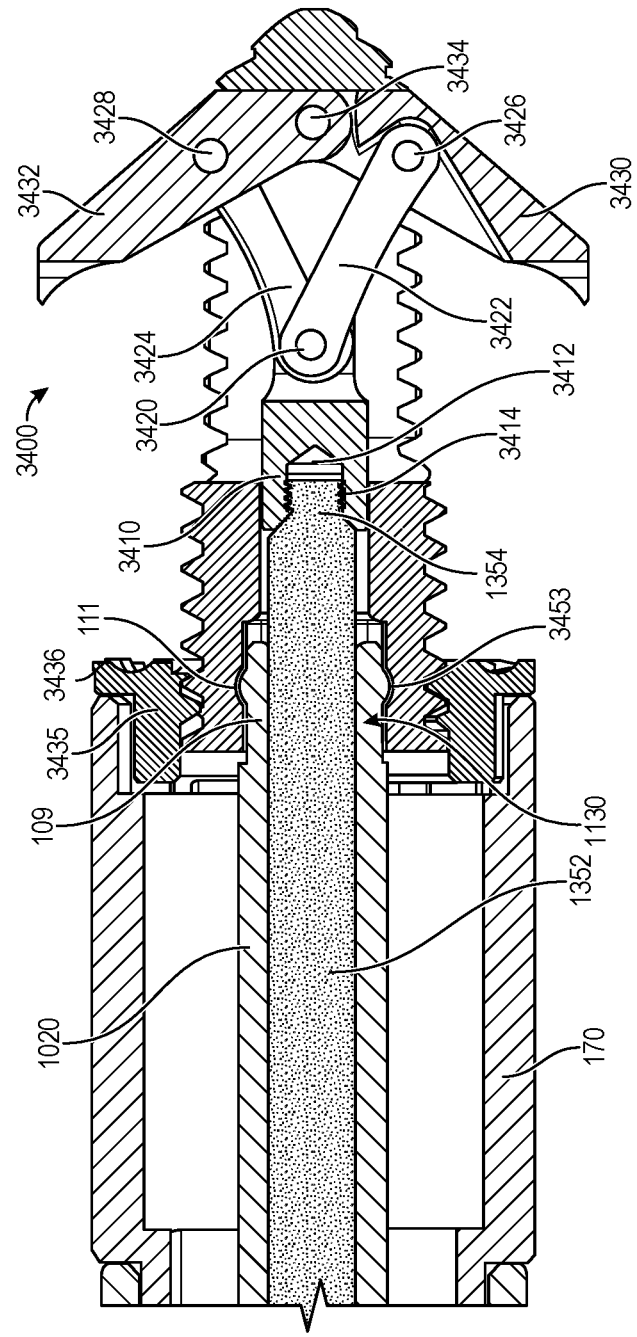
FIG. 56 is a cross sectional view of the insertion instrument attached to the implant of FIG. 51 in the deployed configuration.

In some embodiments, similar to implant 200, implant 3400 may include a hex nut 3435, which may also serve the functions of a spike cap. For example, hex nut 3235 may include a grip plate having a textured surface 3437 on the distal side of the hex nut 3435 to allow for the hex nut 3435 to seat into the spinal process (e.g., spinal process 381a/ 381b) during surgery. In some embodiments, similar to implant 200 and 3200, implant 3400 may include a proximal internal recess 3450. In some embodiments, proximal internal recess 3450 includes detents 3453 configured to receive a portion of the elongated main body 1020 (e.g., ridges 111), as seen in FIGS. 54 and 56 In some embodiments, similar to implant 3200, implant plunger 3410 may include an implant plunger bore 3412. In some embodiments, implant plunger bore 3412 may be configured to receive a portion of the plunger shaft 1352 (e.g., coupling tip 1354). In some embodiments, implant plunger bore 3412 may be configured to temporarily attach to coupling tip 1354. For example, as illustrated in FIGS. 54 and 56 in some embodiments, implant plunger bore 3412 may include a threaded bore 3414. In these embodiments, threaded bore 3414 may be configured to threadably receive coupling tip 1354. As such, implant plunger 3410 and wing actuation tool 1110 may be threadably coupled, such that movement of the wing actuation tool 1110 may deploy/retract wings 3430, 3432.

FIGS. 53-54 illustrate implant 3400 connected to the insertion instrument 3000 while in a retracted state, in some embodiments. As mentioned above, with the implant plunger 3410 at the most proximal location, the wings 3430, 3432 are in the retracted position. This position may be maintained when the coupling tip 1354 of the plunger shaft 1352 is inserted and threadably coupled to the implant plunger 3410 via the threaded bore 3414. As illustrated in FIG. 53, the retracted position is maintained with the plunger knob 1350 pulled or left at the most proximally translated position. As mentioned above and with reference to FIGS. 43-45, in some embodiments when plunger shaft 1352 is in the most proximally translated position, the concentric flange 1356 may abut the distal end of the proximal end cap 1340. In some embodiments, the concentric flange 1356 may not abut the distal end of the proximal end cap 1340 when coupling tip 1354 is coupled to the threaded bore 3414. In some embodiments, the longitudinal distance traveled by the plunger shaft 1352 may be determined by the distance implant plunger 3410 is configured to move within the implant 3400.

Figure 55:
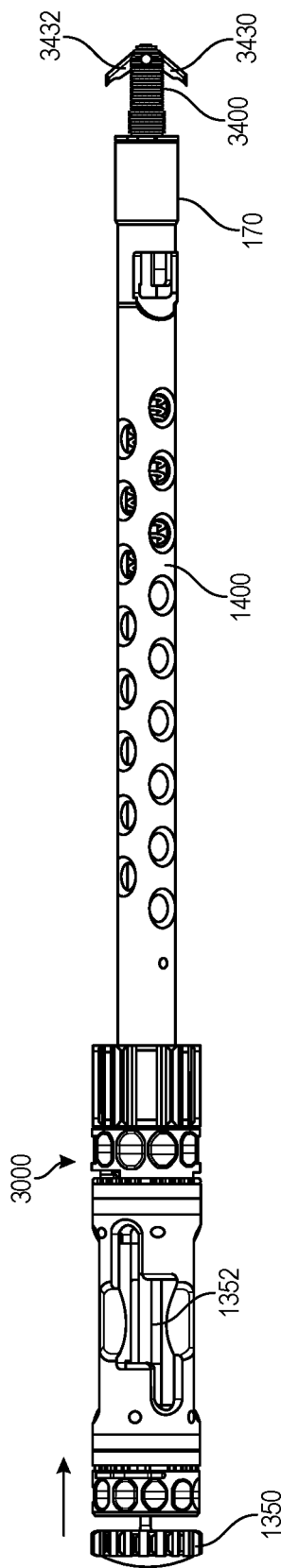
FIG. 55 is a side view of the insertion instrument of FIG. 43 attached to the implant of FIG. 51 in a deployed configuration.

FIGS. 55-56 illustrate implant 3400 connected to the insertion instrument 3000 while in a deployed state, in some embodiments. As mentioned above, translation of the implant plunger 3410 in the distal direction will actuate the wings 3430, 3432 radially outwards into the deployed position. In some embodiments, translation of the implant plunger 3410 in the distal direction occurs via actuation of the plunger knob 1350 in the distal direction (see FIG. 55). For example, note the distal displacement of implant plunger 3410 in FIG. 56 (i.e., deployed) compared to the location of implant plunger 3410 in FIG. 54 (i.e., retracted).

Distal translation of the plunger knob 1350, in some embodiments, is directly translated to distal movement of the plunger shaft 1352 and coupling tip 1354. Accordingly, the coupling tip 1354 displaces the implant plunger 3410 in the distal direction. Distal movement of implant plunger 3410 pushes on linkages 3422, 3424 via the linkage pin 3420. In some embodiments, linkage pin 3420 allows for rotation of linkages 3422, 3424 therearound when the implant plunger 3410 is translated. In some embodiments, the distal ends of linkages 3422, 3424 are connected to wings 3430, 3432 via pins 3426, 3428, respectively. As such, distal translation of implant plunger 3410 causes linkages 3422, 3424 to move both distally and rotate outwards, thereby moving pins 3426, 3428 and thus wings 3430, 3432 outwards. Furthermore, in some embodiments, the distal ends of the wings 3430, 3432 are maintained in place via pivot pin 3434. As such, pivot pin 3434 provides an anchor point for wings 3430, 3432 to pivot therearound when displaced by linkages 3422, 3424. While illustrated as including one pivot pin 3434, in some embodiments, wings 3430, 3432 may be connected via two or more pivot pins.

Importantly, in some embodiments, when coupling tip 1354 is temporarily connected to the implant plunger 3410 via threaded bore 3414, the deployment of the wings 3430, 3432 is reversible. For example, the aforementioned steps may be reversed such that actuation of the plunger knob 1350 in the proximal direction will cause wings 3430, 3432 to close.

The insertion instrument 3000 and wing actuation tool 1110 may similarly be used with implant 3200. The ability to close wings 3230, 3232 or wings 3430, 3432 may provide significant advantages to the surgeon, or other physician, inserting the implant 3200 or 3400. As an example, a surgeon or other physician may perform a step of the procedure, such as inserting the implant 3200/3400 into and through spinal processes 381a, 381b and deploying wings 3230, 3232 or 3430, 3432 within the target interspinous process space 382. Following deployment of the wings 3230, 3232 or 3430, 3432, the physician may, for one reason or another, realize that long term implantation of implant 3200/3400 may not be viable. Accordingly, in some embodiments, the physician may be capable of retracting wings 3230, 3232 or 3430, 3432 via actuation of plunger knob 1350 in the proximal direction, thereby allowing the physician to remove implant 3200/3400 safely and easily.

Assembly of the Insertion Instrument

Referring now to FIGS. 3, 24-25, and 42-46, the insertion instrument 3000 is designed for ease of assembly. The instrument 3000 is initially locked together, with similar steps to those described above. For example, a lock nut tool 2200 may be slid over the elongated main body 1020 and operatively engage the lock nut 2100. The lock nut 2100 may then be threadably rotated around the distal threaded portion 1012 of the hub 1010, with a proximal portion of the elongated main body 1020 being disposed within the bore 1016 of the hub 1010 (see FIGS. 37-38). Once fully threaded therein, elongated main body 1020 is secured to the handle 1060. The insertion instrument 3000 is now ready to receive the wing actuation tool 1110.

As best shown in FIGS. 42-45, the plunger knob 1350 is coupled to the plunger shaft 1352 via the extension 1358. In some embodiments, the extension 1358 is placed through the hole 1342 in proximal end cap 1340 prior to connection to plunger knob 1350. Accordingly, the proximal end cap 1340 is maintained at the portion of plunger shaft 1352 between the plunger knob 1350 and the concentric flange 1356. Once the proximal end cap 1340 is secured to the wing actuation tool 1110 (e.g., see FIG. 44), the distal portion of the plunger shaft 1352 (i.e., the portion of plunger shaft 1352 distal to the concentric flange 1356) is inserted through the proximal ring 1950 and proximal housing 1900 and into the handle 1060. The plunger shaft 1352 continues through the hub 1010, the medial housing 1800, and into the elongated main body 1020.

As the plunger shaft 1352 is slid within the elongated main body 1020, the proximal end cap 1340 eventually abuts the proximal ring 1950. The proximal end cap 1340 is rotated to threadably engage the proximal threaded feature 1170 of the proximal housing 1900 and secure the wing actuation tool 1110 within the handle 1060.

The distal portion 108 of the elongated main body 1020 is inserted through the proximal drive shaft 1600 and spring 1630 and into the axial passage 1440 of the distal hex nut driver 1400 (see FIG. 25), with the spring 1630 abutting a portion of the distal hex nut driver 1400 and the distal end of the proximal drive shaft 1600. The knob 148 of the proximal drive shaft 1600 and/or end cap 150 are rotated to couple the distal threaded feature 1190 of the medial housing 1800 with the end cap 150.

At this point, the wing actuation tool 1110 is secured within insertion instrument 3000. The insertion instrument 3000 is now in the "unlocked" position. "Unlocked" refers to the implant, such as 3200/3400, not being secured to the insertion instrument 3000. The implant 3200/3400 is locked to the insertion instrument 3000 by actuating the plunger shaft 1352 and coupling tip 1354 as described below.

Locking the Implant to the Insertion Instrument

To lock the implant 3200/3400 to the insertion instrument 3000, the plunger knob 1350 should be fully retracted in the proximal direction. This can be easily identified as the plunger knob 1350 will not move further proximally once the concentric flange 1356 abuts the distal end of the proximal end cap 1340 (see FIG. 43).

As seen in FIG. 27, to lock the implant 3200/3400, the distal portion 108 of the elongated main body 1020 is uncovered by sliding the distal hex nut driver 1400 proximally around the proximal drive shaft 1600. The distal hex nut driver 1400 is initially prevented from rotation because the pins 1650 are riding in the complementary slots 1610 (best seen in FIG. 26). However, once the pins 1650 bottom out in the complementary slots 1610, the user can hold the knob 148 and rotate the distal hex nut driver 1400 so the pins 1650 come to rest in the radial portion 1640 of the complementary slots 1610. As a result, the distal hex nut driver 1400 is locked and will stay retracted even when released by the user.

Either before or after distal hex nut driver 1400 is retracted, a matching adapter 170 (see FIG. 4) can be attached to distal opening 1580 and/or slid over the distal portion 108 of the elongated main body 1020. For example, legs 175, 176 can be inserted into the opening 1580 of distal hex nut driver 1400. Locking tabs 177 may provide an audible click when the legs 176 deflect outward into the transverse locking passage 157 to confirm positive engagement for the user.

After positioning the adapter 170 on the hex nut driver 1400, the implant 3200/3400 can be partially engaged to the tip 1130 of the elongated main body 1020 by a snap friction fit. The tip 1130 is slightly compressed, by virtue of the flexible arms 109, and passed into the proximal internal recess 3250, 3450 of the implant 3200, 3400 with the wings 3230, 3232 of the implant 3200, or wings 3430, 3432 of implant 3400, aligned with the flexible arms 109. The tip 1130 stops within the proximal internal recess 3250, 3450 when the flexible arms 109 fit within the detents 3253, 3453. At this point, the implant 3200, 3400 is coupled to the insertion instrument 3000 by the main body 1020 but not yet "locked."

To lock the implant 3200, 3400 to the insertion instrument 3000, the plunger shaft 1352, and thus the coupling tip 1354, are moved from the unlocked position to the locked position. To move the plunger shaft 1352 distally, the plunger knob 1350 is pushed distally, as shown by the arrow in FIG. 55. When translated longitudinally, the coupling tip 1354 will enter through the proximal internal recess 3250, 3450 and come into contact with the threaded bore 3214, 3414 of the implant plunger 3210, 3410. Additionally, the plunger shaft 1352 extends through the tip 1130 of the elongated main body 1020 and exerts an outward force on the flexible arms 109, thereby pressing ridges 111 into the detents 3253, 3453. Thus, the flexible arms 109 of the elongated main body 1020 can no longer flex out of the detents 3253, 3453. At this point, the coupling tip 1354 is merely abutting the distal end of the implant plunger 3210, 3410 but has not yet been threadably received by the threaded bore 3214, 3414. In some embodiments, a user may identify that the coupling tip 1354 is against the implant plunger 3210 by visually seeing the deployment of wings 3230, 3232 or 3430, 3432. However, such biasing of the coupling tip 1354 against the implant plunger 3210, 3410 will not dislodge the implant 3200, 3400 due to the connection of the ridges 111 to the detents 3253, 3453.

Once a user identifies that the coupling tip 1354 is properly against the implant plunger 3210, 3410 and the threaded bore 3214, 3414, the user may rotate the coupling tip 1354 by means of the plunger knob 1350 to cause the coupling tip 1354 to threadably insert into the threaded bore 3214, 3414 of the implant plunger 3210, 3410. For example, a user may rotate the plunger knob 1350 such that the coupling tip 1354 is threadably received by the threaded bore 3214, 3414. In some embodiments, rotation of implant 3200, 3400 is prevented due to the flexible arms 109 engagement with the detents 3253, 3453. Once the coupling tip 1354 is fully received by the threaded bore 3214, 3414, a user may no longer be able to rotate plunger knob 1350 and therefore determine that the coupling tip 1354 is fully coupled to the threaded bore 3214, 3414. Consequently, the implant 3200, 3400 is tightly coupled and locked to the coupling tip 1354 so that inadvertent detachment does not occur. The user may then pull the plunger knob 1350 proximally (i.e., as shown in FIG. 53) to retract the wings 3230, 3232 or 3430, 3432. In some embodiments, prior to retraction of wings 3230, 3232 or 3430, 3432, a user may insert, coat, or otherwise place bone graft material (e.g., any material having osteogenic properties) into the interior of the main body 3402 of implant 3200/3400. By placing the bone graft material in this location, the material will be well suited to aid in the recovery of the spinal processes 381*a*, 381*b* as this region of implant 3200/3400 will be directly against spinal processes 381*a*, 381*b* following the procedure (e.g., see FIG. 23). With wings 3230, 3232 or 3430, 3432 in the closed position, the insertion instrument 3000 is now ready to have the socket end 1560 of the distal hex nut driver 1400 engaged to the hex nut 3235, 3435 of the implant 3200, 3400.

To engage the distal hex nut driver 1400 to the hex nut 3235, 3435 of the implant 3200, 3400, the knob 148 is held to prevent rotation while the distal hex nut driver 1400 is rotated to bring the pins 1650 out of the radial portion 1640 of the complementary slots 1610. The spring 1630 will bias the distal hex nut driver 1400 distally so care should be taken to slowly extend the distal hex nut driver 1400 to have the hex socket 172 properly engage the hex nut 3235/3435 of the implant 3200/3400 (best seen in FIGS. 54 and 56). In order to have the hex socket 172 properly engage the hex nut 3235, 3435, a slight manual rotation or jiggle of the distal hex nut driver 1400 may be required. The implant 3200, 3400 is now locked to the insertion instrument 3000 and ready for implantation. The force provided by the spring 1630 is optimized to ensure proper, reliable engagement between the adapter 170 and hex nut 3235, 3435 while not providing excessive force to interfere with the operation of the insertion instrument 3000 or deployment of the implant 3200, 3400.

Deployment of the Implant in the Interspinous Space

FIGS. 20-23 illustrate various stages during insertion and placement of the implant 200/3200 into a target interspinous process space 382. Steps of deployment of the implant 200/3200/3400 are similar between insertion instrument 100, insertion instrument 1000, and insertion instrument 3000, with slight variations in the deployment of the wings, and therefore the below description is in reference to insertion instruments 100, 1000, and 3000 with distinct steps of the wing deployment identified for insertion instrument 3000. Additional details are set forth in U.S. patent application Ser. No. 12/011,905, filed Jan. 30, 2008 (U.S. Patent Pub. No. 2009/0054988), which is incorporated herein by reference in its entirety.

FIG. 20 is a dorsal (rear, with respect to the patient) view of the implant 200/3200/3400, still held by the insertion instrument 100/1000/3000, within a lumen of an introducer tube 387, during lateral insertion thereof. For direct lateral insertion of the implant 200/3200/3400 into the target interspinous process space 382, an incision is formed in the skin 388 of a patient, and ultimately an introducer tube 387 is advanced through the tissue to the target interspinous process space 382, through which the implant 200/3200/3400 is advanced, connected to the insertion instrument 100/1000/3000.

The implant 200/3200/3400 is axially rotated by way of the insertion instrument 100/1000/3000, thus threading the implant 200/3200/3400 into the target interspinous process space 382, distracting the adjacent spinous processes 381a, 381b, and advancing the implant 200/3200/3400, generally centered with respect to the spinous processes 381a, 381b.

To rotate the implant 200/3200/3400, the handle 1060 is rotated in a tightening or clockwise direction to self-thread the implant 200/3200/3400 through the interspinous space 382, as shown in FIG. 21. During the rotation of the implant 200/3200/3400, the implant 200/3200/3400 distracts the interspinous space. Relative rotation and axial translation between the implant 3200/3400 and the insertion instrument 3000 is inhibited because the implant 3200/3400 is locked onto the tip 1130 of main body 1020 as well as secured to the coupling tip 1354 of plunger shaft 1352. Distraction can also be performed in advance by a separate instrument, with insertion of the implant 200/3200/3400 following, and maintaining such distraction.

When wings 220a/3230/3430, 220b13232/3432 have passed through the interspinous space 382 as shown in FIG. 22, the wings 220a/3230/3430, 220b/3232/3432 can be deployed. To deploy the wings 3230, 3232 of implant 3200 or wings 3430,3432 of implant 3400, the plunger knob 1350 is pushed distally (best shown in FIG. 55). As mentioned above, as the plunger knob 1350 is moved distally, the coupling tip 1354 exerts distal pressure and subsequent movement of implant plunger 3210, 3410. Distal movement of the implant plunger 3210, 3410 causes radially outward movement of wings 3230, 3232 or 3430, 3432 via linkages 3222, 3224 or 3422, 3424. The physician can also verify proper deployment of the wings 3230, 3232 or 3430, 3432 by fluoroscopy. Once the wings 3230, 3232 or 3430, 3432 are deployed, the implant 3200/3400 can be set in final position.

Referring now to FIGS. 23 and 47-52, the hex nut 3235/3435 of the implant 3200/3400 is shown being driven by the distal hex nut driver 1400 to engage the spikes 3236, 3436 to the spinous processes 381a, 381b. In some embodiments, the distal hex nut driver 1400 rotates the hex nut 3235/3435 to move the grip plate 3238/3437 distally.

To rotationally drive the hex nut 235/3235/3435, the knob 148 is rotated clockwise relative to the elongated main body 1020. Turning the knob 148 turns the adapter 170 and thereby the hex nut 235/3235/3435. Once the spike cap/grip plate 230/3238/3437 engages the spinous processes 381a, 381b, the wings 220a/3230/3430, 220b/3232/3432 are drawn proximally into engagement with the bone 381a, 381b. While the distal hex nut driver 1400 is used to tighten the hex nut 235/3235/3435, the surgeon can feel the spike cap/grip plate 230/3238/3437, become fully seated and/or full seating is seen in an accompanying fluoroscopy display.

Once the implant 200/3200/3400 is properly deployed, the insertion instrument 100/1000/3000 is disengaged from the implant 200/3200/3400. To disengage the coupling tip 1354 of the wing actuation tool 1110, the plunger knob 1350 may be rotated in the counter-clockwise direction (viewed proximally). Such rotation of the plunger knob 1350 threadably decouples the coupling tip 1354 from the threaded bore 3214/3414. Once the coupling tip 1354 is fully removed from the threaded bore 3214/3414, the plunger shaft 1352 may be translated proximally until no longer pressing outwardly on the flexible arms 109. Accordingly, the flexible arms 109 are again allowed to flex so that the tip 1130 of main body 1020 is released from detents 3253, 3453 in proximal internal recess 3250/3450 of the implant 3200/3400. Proximal motion of the insertion instrument will disengage both the adapter 170 and the main body 1020 from the implant 3200/3400. Once removed, the insertion instrument 3000 can be removed from the patient for disassembly, cleaning, and re-use.

Disassembly of the Insertion Instrument

It is advantageous to disassemble the insertion instrument 3000 for cleaning or replacing parts. Referring to FIGS. 3-4, 7-8, and 43, the proximal end cap 1340 can be unscrewed from the proximal housing 1900, and the wing actuation tool 1110 removed from the elongated main body 1020, handle 1060, and proximal housing 1900. The distal hex nut driver 1400 and the proximal drive shaft 1600 can be removed from around the elongated main body 1020. The elongated main body 1020 can be removed from the handle 1060 by unlocking the locking system 2000 as described above. The adapter 170 can be unsnapped from the distal hex nut driver 1400. At this point, the components of the insertion instrument 3000 are ready to be cleaned and/or replaced.

As described in detail above, the wing actuation tool 1110 allows for a secure connection between the plunger shaft 1352 and the implant 3200/3400 so as to prevent unwanted release of the implant 3200/3400 during surgery. Additionally, wing actuation tool 1110 provides for easy deployment of the wings 3230, 3232 or 3430, 3432 of the implant 3200/3400 during surgery. For example, a user (e.g., physician) need only to press or pull on plunger knob 1350 to cause deployment of or retraction of the wings 3230, 3232 or 3430, 3432. Wing actuation tool 1110 further provides for the ability to close wings 3230, 3232 or 3430, 3432 following deployment. Such capabilities allow for a user to discontinue a surgery with ease, if, after deployment of the wings 3230, 3232 or 3430, 3432, the user determines that long term implantation of the implant 3200/3400 is not feasible for any reason.

Furthermore, the wing actuation tool 1110 and proximal end cap 1340 are configured to be interchangeable with any insertion instrument 100/1000/3000. As such, a user may easily switch between deployment methods (e.g., wing actuation tool 1110 or plunger 110) depending on the specific needs of the user. Or, in another example, a user may be able to easily exchange certain components of their current insertion instrument 100/1000 to incorporate the wing actuation tool 1110.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof. It is also to be appreciated that the following claims can be rearranged, combined, combined with other features disclosed herein, presented in multiple dependent form and the like.

What is claimed is:

1. An insertion instrument for inserting an interspinous implant into a patient, the insertion instrument comprising:
   an elongated main body extending distally from a handle,
      a distal end of the elongated main body configured to connect to the interspinous implant; and
   an actuation tool, comprising:
      a plunger knob disposed proximal to the handle;
      a plunger shaft extending distally from the plunger knob, the plunger shaft being received within a lumen of the handle and the elongated main body, the plunger shaft being longitudinally translatable within the lumen;
      a concentric flange disposed on a proximal portion of the plunger shaft, the concentric flange being received within the handle; and
      a coupling tip disposed at a distal end of the plunger shaft, the coupling tip configured to temporarily attach and lock to the interspinous implant;
         wherein distal longitudinal translation of the plunger knob actuates one or more components of the interspinous implant via the coupling tip,
         wherein proximal longitudinal translation of the plunger knob actuates one or more components of the interspinous implant via the coupling tip.

2. The insertion instrument of claim 1, further comprising a proximal end cap comprising a hole, said hole receiving a portion of the plunger shaft, wherein the plunger knob is disposed on a proximal side of the hole and the concentric flange is disposed on a distal side of the hole.

3. The insertion instrument of claim 2, further comprising:
   a proximal housing disposed between the proximal end cap and the handle, wherein the proximal housing is removably coupled to the proximal end cap to allow for replacement of the actuation tool.

4. The insertion instrument of claim 1, wherein the coupling tip comprises external threads configured to attach to an implant plunger of the interspinous implant.

5. The insertion instrument of claim 4, wherein distal longitudinal translation of the plunger knob distally displaces the implant plunger, thereby deploying one or more wings of the interspinous implant.

6. The insertion instrument of claim 4, wherein proximal longitudinal translation of the plunger knob proximally displaces the implant plunger, thereby retracting one or more wings of the interspinous implant.

7. A system for inserting a spinal implant into a patient comprising:
   an insertion instrument comprising:
      an actuation tool comprising:
         a plunger knob having a plunger shaft extending distally therefrom;
         a concentric flange disposed around a proximal portion of the plunger shaft;
         a proximal end cap receiving the plunger shaft, the proximal end cap disposed distal to the plunger knob and proximal to the concentric flange; and
         a coupling tip at a distal end of the plunger shaft, the coupling tip configured to receive the spinal implant thereon,
            wherein distal longitudinal translation of the plunger knob actuates one or more components of the spinal implant via the coupling tip,
            wherein proximal longitudinal translation of the plunger knob actuates one or more components of the spinal implant via the coupling tip;
      a handle disposed distal to the proximal end cap, the handle receiving the plunger shaft and the concentric flange therein;
      a proximal drive shaft extending distally from a drive shaft knob, the drive shaft knob rotatably attached to a distal end of the handle; and
      a distal hex nut drive concentrically disposed around a distal portion of the proximal drive shaft.

8. The system of claim 7, wherein the coupling tip of the actuation tool is configured to fixedly attach to an implant plunger disposed within the spinal implant to deploy and retract a plurality of wings of the spinal implant.

9. The system of claim 7, wherein the plunger knob abuts a proximal side of the proximal end cap when the actuation tool is in a distalmost position.

10. The system of claim 7, wherein the concentric flange abuts a distal side of the proximal end cap when the actuation tool is in a proximalmost position.

11. The system of claim 7, further comprising:
    a proximal housing disposed between the proximal end cap and the handle, wherein the proximal housing is removably coupled to the proximal end cap to allow for replacement of the actuation tool.

12. A method of using an insertion instrument to place a spinal implant into a patient, the method comprising:
    assembling the insertion instrument, comprising:
       inserting an extension of a plunger shaft through a hole disposed on a proximal end cap, movement of the extension in a proximal direction through the hole being limited by a concentric flange disposed on the plunger shaft and abutting a distal side of the proximal end cap;
       mechanically coupling the extension to a plunger knob;
       inserting a distal portion of the plunger shaft through a proximal housing, a handle, and an elongated main body;
       coupling the proximal end cap to the proximal housing;
       inserting a distal portion of the elongated main body through a proximal drive shaft;
       securing the proximal drive shaft to the handle; and
       operatively coupling a distal portion of the proximal drive shaft to a distal hex nut driver.

13. The method of claim 12, further comprising:
    attaching an adapter to a distal end of the distal hex nut driver; and
    locking the spinal implant to the insertion instrument, comprising:

securing the distal hex nut driver in a first retracted position, the first retracted position exposing a tip of the elongated main body; and inserting the tip of the elongated main body into a proximal internal recess of the spinal implant.

14. The method of claim 13, wherein locking the spinal implant to the insertion instrument further comprises:

distally translating the plunger knob, thereby translating the plunger shaft into the proximal internal recess of the spinal implant; and rotating the plunger knob in a first direction, thereby temporarily locking the plunger shaft to the spinal implant.

15. The method of claim 14, further comprising:

releasing the distal hex nut driver from the first retracted position, thereby placing the distal hex nut driver in a second extended position, wherein, in the second extended position, the adapter mechanically engages a proximal nut of the spinal implant.

16. The method of claim 15, wherein the plunger shaft comprises a coupling tip at the distal end thereof having an external threading, wherein temporarily locking the plunger shaft to the spinal implant comprises threadably attaching the coupling tip to a threaded bore of an implant plunger of the spinal implant, the implant plunger being longitudinally displaceable.

17. The method of claim 16, further comprising:

following attachment of the coupling tip of the plunger shaft to the implant plunger, proximally translating the plunger knob, thereby causing proximal displacement of the implant plunger.

18. The method of claim 17, further comprising:

inserting the spinal implant into an interspinous process space, comprising:

rotating the handle of the insertion instrument, thereby inserting the spinal implant into the interspinous process space; and deploying one or more wings of the spinal implant by translating the plunger knob distally, the one or more wings being substantially located on a contralateral side of one or more spinous processes defining the interspinous process space.

19. The method of claim 18, further comprising:

rotating the distal hex nut driver to rotate the proximal nut of the spinal implant, the proximal nut being seated on a side of the one or more spinous processes opposite the one or more wings.

20. The method of claim 19, further comprising:

unlocking the spinal implant from the insertion instrument, comprising:

rotating the plunger knob in a second direction, the second direction being opposite the first direction to unscrew the plunger shaft from the threaded bore;

proximally translating the plunger knob, thereby removing the plunger shaft from the proximal internal recess of the spinal implant; and removing the tip of the elongated main body from the proximal internal recess of the spinal implant.

* * * * *